US010842861B2

(12) United States Patent
Van Immerseel et al.

(10) Patent No.: US 10,842,861 B2
(45) Date of Patent: Nov. 24, 2020

(54) METHOD OF REDUCING EGG CONTAMINATION

(71) Applicant: Universiteit Gent, Ghent (BE)

(72) Inventors: Filip Van Immerseel, Eke (BE); Ruth Raspoet, Erembodegem (BE); Richard Ducatelle, Wortegem-Petegem (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 16/304,484

(22) PCT Filed: May 23, 2017

(86) PCT No.: PCT/EP2017/062330
§ 371 (c)(1),
(2) Date: Nov. 26, 2018

(87) PCT Pub. No.: WO2017/202804
PCT Pub. Date: Nov. 30, 2017

(65) Prior Publication Data
US 2019/0192647 A1 Jun. 27, 2019

(30) Foreign Application Priority Data
May 26, 2016 (EP) ...................................... 6171540

(51) Int. Cl.
A61K 39/00 (2006.01)
A61K 39/112 (2006.01)
A61P 31/04 (2006.01)
A61K 9/00 (2006.01)

(52) U.S. Cl.
CPC ........ *A61K 39/0275* (2013.01); *A61K 9/0019* (2013.01); *A61K 9/0053* (2013.01); *A61K 9/0073* (2013.01); *A61P 31/04* (2018.01); *A61K 2039/522* (2013.01); *A61K 2039/54* (2013.01); *Y02A 50/482* (2018.01)

(58) Field of Classification Search
None
See application file for complete search history.

(56) References Cited

FOREIGN PATENT DOCUMENTS

WO WO-2006129090 A2 * 12/2006 ........... A61K 39/105
WO WO2006129090 A2 12/2006

OTHER PUBLICATIONS

Kilroy et al. 2016 (Prevention of egg contamination by *Salmonella enteritidis* after oral vaccination of laying hens with *Salmonella enteritidis* Dtoc and DacrABacrEFmdtABC mutants; 47:82) (Year: 2016).*
Baucheron et al. 2005 (ToIC but not AcrB is essential for multidrug-resistant *Salmonella enterica* serotype Typhimurium colonization of chicks; Journal of Antimicrobial Chemotherapy (2005) 55, 707-712) (Year: 2005).*

Barrow et al., "Inhibition of colonization of the chicken alimentary tract with *Salmonella typhimurium* gram-negative facultatively anaerobic bacteria", Epid. Inf., vol. 98, No. 3, 1987, pp. 311-322.
De Cort et al., A colonisation-inhibition culture consisting of *Salmonella enteritidis* and Typhimurium ΔhilAssrAfliG strains protects against infection by strains of both serotypes in broilers, Vaccine, vol. 32, 2014, pp. 4633-4638.
De Cort et al., "A *Salmonella enteritidis* hilAssrAfliG deletion mutant is a safe live vaccine strain that confers protection against Colonization by *Salmonella enteritidis* in broilers", Vaccine, vol. 31, 2013, pp. 5104-5110.
De Cort et al., "Administration of a *Salmonella enteritidis* ΔhilAssrAfliG strain by coarse spray to newly hatched broilers reduces colonization and shedding of a *Salmonella enteritidis* challenge strain", Poultry Science, vol. 94, 2015, pp. 131-135.
Desin et al.,, "*Salmonella* vaccines in poultry: past, present and future", Expert Rev. Vaccines, vol. 12, No. 1, 2013, pp. 87-96.
Gantois et al., "Oral immunisation of laying hens with the live vaccine strains of TAD *Salmonella* vac® E and TAD *Salmonella* vac® T reduces internal egg contamination with *Salmonella enteritidis*", Vaccine, vol. 24, Nos. 37-39, 2006, pp. 6250-6255.
Gantois et al., "Mechanisms of egg contamination by *Salmonella enteritidis*", FEMS Microbiol. Rev., vol. 33, 2009, pp. 718-738.
Gast et al., "Effect of Prior Serial In Vivo Passge on the Frequency of *Salmonella enteritidis* Contamination in Eggs from Experimentally Infected Laying Hens", Avian Diseases, vol. 47, 2003, pp. 633-639.
Gast et al., "Influence of the Level and Location of Contamination on the Multiplication of *Salmonella enteritidis* at Different Storage Temperatures in Experimentally Inculated Eggs", Poultry Science, vol. 79, 2000, pp. 559-563.
Hassan et al., "Efficacy of a Live Avirulent *Salmonella typhimurium* Vaccine in Preventing Colonization and Invasion of Laying Hens by *Salmonella typhimurium* and *Salmonella enteritidis*", Avian Diseases, vol. 41, No. 4, 1997, pp. 783-791.
Keller et al., *Salmonella enteritidis* Colonization of the Reproductive Tract and Forming and Freshly Laid Eggs of Chickens, Infection and Immunity, vol. 63, No. 7, 1995, pp. 2443-2449.
Lister, S.A., *Salmonella enteritidis* infection in broilers and broiler breeders, The Veterinary Record, vol. 123, 1988, p. 350.
Matsuda et al., "Comparison of the Safety and Efficacy of a New Live *Salmonella gallinarum* Vaccine Candidate, JOL916, with the SG9R Vaccine in Chickens", Avian Diseases, vol. 55, 2011, pp. 407-412.
Methner et al., "Experimental Oral Infection of Specific Pathogen-free Laying Hens and Cocks with *Salmonella enteritidis* Strains", J. Vet. Med. B vol. 42, No. 8, 1995, pp. 459-469.
Methner et al., "Infection Model for Hatching Chicks Infected with *Salmonella enteritidis* ", J. Vet. Med. B, vol. 42, No. 8, 1995, pp. 471-480.
Miyamoto et al., "Evaluation of the Efficacy of *Salmonella enteritidis* Oil-Emulsion Bacterin in an Intravaginal Challenge Model in Hens", Avian Diseases, vol. 43, No. 3, 1999, pp. 497-505.

(Continued)

Primary Examiner — Mary Maille Lyons
(74) Attorney, Agent, or Firm — Dinsmore & Shohl LLP

(57) ABSTRACT

The present invention relates to *Salmonella* mutant strains and their use as a vaccine for preventing *Salmonella* infection, in particular in eggs.

15 Claims, 16 Drawing Sheets
Specification includes a Sequence Listing.

(56) References Cited

OTHER PUBLICATIONS

Nandre et al., Efficacy for a New Live Attenuated *Salmonella enteritidis* Vaccine Candidate to Reduce Internal Egg Contamination, Zoonoses and Public Health, vol. 61, No. 1, 2014, pp. 55-83.
Nassar et al., Use of live and inactivated *Salmonella enteritidis* phage type 4 vaccines to immunise laying hens against experimental infection, Rev. sci. tech. Off. int. Epiz., vol. 13, No. 3, 1994, pp. 855-867.
Nishino et al., "Virulence and drug resistance roles of multidrug efflux systems of *Salmonella enterica* serovar Typhimurium" Molecular Microbiology, vol. 59, No. 1, 2006, pp. 126-141.
Tsukasa Horiyama et al., "ToIC dependency of multidrug eefflux systems in *Salmonella enterica* serovar Typhimurium", Journal of Antimicrobial Chemotherapy, vol. 65, 2010, pp. 1372-1376.
Van Immerseel et al., "The effect of vaccination with a *Salmonella enteritidis* aroA mutant on early cellular responses in caecal lamina propria of newly-hatched chickens", Vaccine, vol. 20, 2002, pp. 3034-3041.
Van Immerseel et al., "*Salmonella gallinarum* field isolates from laying hens are related to the vaccine strain SG9R", Vaccine, vol. 31, 2013, pp. 4940-4945.
Van Immerseel et al., "Clostridium perfringens in poultry: an emerging threat for animal and public health", Avian Pathology, vol. 33, No. 6, 2004, pp. 537-549.
Woodward et al., "Distribution, gene sequence and expression in vivo of the plasmid encoded fimbrial antigen of *Salmonella* serotype Enteritidis", Epidemiol. Infect., vol. 117, 1996, pp. 17-28.
Woodward et al., "The efficacy of Salenvac, a *Salmonella enterica* subsp. *enterica* serotype enteritidis iron-restricted bacterin vaccine, in laying chickens", Avian Pathology, vol. 31, 2002, pp. 383-392.
Allen-Vercoe et al., "The role of flagella, but not fimbriae, in the adherence of *Salmonella enterica* serotype Enteritidis to chick gut explant", J. Med Microbiol., vol. 48, 1999, pp. 771-780.
Bohez et al., "The Effect of Oral administration of a homologous hilA mutant strain on the long-term colonization and transmission of *Salmonella enteritidis* in broiler chickens", Vaccine, vol. 26, 2008, pp. 372-378.
Bohez et al., "*Salmonella enterica* serovar Enteritidis colonization of the chicken caecum require the HilA regulatory protein", Veterinary Microbiology, vol. 116, 2006, pp. 202-210.
Datsenko et al., "One-step inactivation of chromosomal genes in *Escherichia coli* K-12 using PCR products", Proc Natl Acad Sci USA, vol. 97, No. 12, 2000, pp. 6640-6645.
Davison et al.,, Field Observations with *Salmonella enteritidis* Bacterins, Avian Diseases, vol. 43, 1999, pp. 664-669.
DE Buck et al., "Protection of laying hens against *Salmonella enteritidis* by immunization with type 1 fimbriae", Veterinary Microbiology, vol. 105, No. 2, 2005, pp. 93-101.
Desmidt et al., "Role of the humoral immune system in *Salmonella enteritidis* phage type four infection in chickens", Veterinary Immunology and Immunopathology, vol. 63, 1998, pp. 355-367.
Desmidt et al., "Detection of antibodies to *Salmonella enteritidis* in sera and yolks from experimentally and naturally Infected chickens", the Veterinary Record, vol. 138, 1996, pp. 223-226.
"The European Union Summary Report on Trends and Sources of Zoonoses, Zoonotic Agents and Food-borne Outbreaks in 2011" EFSA Journal, vol. 11, No. 4, 2013, pp. 19-73.
Anonymous, Commission Regulation (EC) No. 1237/2007 of Oct. 23, 2007 amending regulation (EC) No. 2160/2003 of the European Parliament and of the Council and Decision 2006/696/EC as regards the placing on the market of eggs from *Salmonella* infected flocks of laying hens, Official Journal of the European Union, L280/5, pp. 5-9.
Majowicz et al., "The Global Burden of Nontyphoidal *Salmonella gastroenteritis*, International Collaboration on Enteric Disease 'Burden of Illness' Studies; Clinical Infectious Diseases", vol. 50, No. 6, 2010, pp. 882-889.
Webber et al., "The Global Consequence of Disruption of the AcrAB-ToIC Efflux Pump in *Salmonella enterica* Includes Reduced Expression of SPI-1 and Other Attributes Required to Infect the Host", Journal of Bacteriology, vol. 191, No. 13, 2009, pp. 4276-4285.
Buckley et al., "The AcrAb-ToIC efflux system of *Salmonella enterica* serovar Typhimurium plays a role in pathogenesis", Cellular Microbiology, vol. 8, No. 5, 2006, pp. 847-856.
Van Parys et al., "*Salmonella typhimurium* induces SPI-1 and SPI-2 regulated and strain dependent downregulation of MHC II expression on porcine alveolar macrophages", Veterinary Research, vol. 43, No. 52, 2012, pp. 1-14.
International Search Report and Written Opinion, completed Jul. 21, 2017, pertaining to PCT/EP2017/062330, filed May 23, 2017.
International Preliminary Report on Patentability, dated Nov. 27, 2018, pertaining to PCT/EP2017/062330, filed May 23, 2017.
Heyndrickx el al., "Recent changes in *Salmonella* nomenclature: The need for clarification", The Veterinary Journal 170 (2005), pp. 275-277.

\* cited by examiner

*tolC* gene

ATGAAGAAATTGCTCCCCATCCTTATCGGCCTGAGCCTGTCGGGGTTCAGCACACTAAGCCAGGCAGAGA
ACCTGATGCAAGTTTATCAGCAAGCACGCCTGAGCAACCCGGAATTGCGTAAATCCGCTGCCGATCGCGA
TGCTGCATTCGAAAAAATTAACGAAGCGCGTAGTCCTTTACTGCCGCAACTGGGTTTAGGTGCCGACTAC
ACCTACAGCAACGGTTATCGCGATGCGAACGGTATCAACTCCAATGAAACCAGCGCTTCTCTGCAATTAA
CGCAGACGCTATTTGATATGTCGAAATGGCGTGGGCTCACCCTGCAAGAAAAGCAGCAGGCATTCAGGA
TGTCACCTATCAGACCGATCAGCAGACGCTGATCCTCAATACCGCGAACGCGTATTTTAAGGTATTGAAC
GCTATTGATGTGCTTTCCTATACCCAGGCGCAAAAAGAGGCTATCTACCGTCAGTTAGATCAAACGACGC
AACGTTTTAACGTGGGTCTGGTCGCCATTACCGACGTGCAAAACGCCCGTGCGCAATATGATACCGTACT
GGCGAATGAAGTGACCGCCCGCAACAACCTGGATAACGCGGTAGAAGAGCTGCGCCAGGTAACCGGCAAT
TATTACCCGGAGCTGGCGTCGCTTAACGTCGAGCATTTTAAAACCGACAAACCCAAAGCTGTTAATGCGC
TGTTGAAGGAAGCGGAAAACCGTAACCTGTCGCTGTTGCAGGCGCGTTTAAGTCAGGATCGGCGCGCGA
GCAAATCCGTCAGGCGCAGGATGGTCACCTGCCGACGCTGAATTTAACGGCCTCAACCGGCATTTCTGAT
ACCTCTTATAGCGGTTCTAAAACCAACTCCACCCAGTACGACGATAGCAACATGGGGCAGAATAAAATCG
GCCTTAACTTCTCCCTGCCGCTGTATCAAGGTGGGATGGTTAACTCGCAGGTAAAACAGGCGCAGTATAA
CTTCGTCGGCGCAAGCGAACAGCTGGAAAGCGCGCACCGTAGCGTGGTGCAGACCGTACGTTCTTCCTTT
AACAATATTAACGCCTCCATCAGCAGCATCAACGCGTATAAACAGGCGGTCGTTTCCGCGCAAAGTTCTT
TGGATGCCATGGAAGCCGGTTACTCGGTCGGTACACGTACCATTGTTGACGTACTGGATGCCACCACCAC
TCTGTATGATGCCAAGCAGCAACTGGCCAACGCGCGTTATACCTATTTGATTAATCAGTTAAATATCAAA
TATGCGCTCGGTACGCTGAACGAGCAGGATCTGCTCGCGCTTAACAGTACGTTGGGTAAACCTATCCCGA
CGTCGCCGGAAAGCGTAGCGCCGGAAACGCCAGATCAGGATGCTGCCGCAGACGGTTATAATGCTCATAG
CGCCGCGCCAGCAGTACAGCCGACCGCCGCTCGCGCCAACAGCAATAACGGCAATCCATTCCGGCATTGA
(SEQ ID NO: 1)

*acrA* gene

ATGAACAAAAACAGAGGGTTAACGCCTCTGGCGGTCGTTCTGATGCTCTCAGGCAGCTTAGCGCTAACAG
GATGTGACGACAAACAGGACCAGCAAGGCGGCCAGCAGATGCCAGAAGTTGGGGTTGTCACACTAAAAAC
GGAACCACTGCAAATCACAACTGAACTTCCGGGTCGTACCGTTGCTTACCGTATCGCCGAAGTTCGCCCG
CAGGTAAGCGGCATTATCCTGAAGCGTAATTTCGTTGAGGGAAGTGATATCGAAGCGGGAGTCTCTCTCT
ATCAGATTGATCCTGCGACCTACCAGGCGACTTACGACAGCGCTAAGGGCGATCTGGCAAAAGCGCAGGC
CGCCGCGAATATCGCTGAACTGACGGTGAAGCGTTATCAAAAGCTGCTGGGTACGCAGTACATCAGTAAG
CAGGAATACGATCAGGCGCTGGCTGACGCACAACAAGCGACTGCCGCTGTTGTCGCAGCAAAAGCCGCCG
TTGAAACCGCACGTATCAACCTGGCGTATACCAAAGTCACCTCGCCGATTAGCGGTCGTATTGGTAAGTC
ATCCGTAACGGAAGGCGCACTGGTACAGAACGGTCAGGCGTCGGCGCTGGCGACAGTGCAGCAGCTGGAC
CCTATTTATGTCGATGTGACCCAGTCCAGCAATGACTTCCTGCGCCTGAAGCAGGAGCTGGCAAATGGTT
CGCTGAAACAGGAAAACGGCAAAGCGAAGGTCGACCTGGTGACCAGCGACGGTATCAAATTCCCGCAGTC
CGGTACGCTTGAGTTCTCCGACGTGACCGTTGACCAAACCACCGGGTCTATTACTTTGCGCGCCATCTTC
CCTAACCCGGATCACACCTTATTGCCAGGAATGTTCGTTCGCGCACGTCTGCAGGAAGGGACAAAACCGA
CGGCATTACTGGTTCCACAACAGGGCGTTACCCGTACTCCACGCGGCGATGCCACGGTGCTGGTGGTTGG
CGCTGATAACAAAGTGGAAACCCGCCAAATCGTCGCAAGCCAGGCGATCGGCGATAAGTGGCTGGTGACT
GACGGATTGAAAGCGGGCGACCGCGTAGTCGTCAGCGGGCTGCAAAAAGTACGTCCTGGCGCACAGGTTA
AAGTACAGGAAATTACCGCGGATAACAAACAGCAAGCCGCAAGCGGTGATCAACCTGCTCAGCCCAGGTC
TTAA (SEQ ID NO: 2)

FIGURE 6

*acrB* gene

```
ATGCCTAATTTCTTTATCGATCGCCCTATATTTGCGTGGGTGATCGCCATCATCATGTTGGCAGGGG
GGCTCGCGATCCTCAAATTGCCGGTAGCGCAATATCCGACGATTGCGCCACCAGCAGTGACGATCTCCGC
AACCTACCCTGGCGCTGATGCGAAAACGGTACAGGATACCGTCACGCAGGTTATCGAACAGAATATGAAC
GGTATCGATAACCTGATGTATATGTCCTCCAACAGTGACTCCACGGGGACCGTGCAGATCACGCTGACCT
TTGAATCCGGCACCGATGCGGATATCGCGCAGGTTCAGGTTCAGAACAAGTTGCAACTGGCAATGCCGTT
ACTTCCCCAGGAAGTACAGCAACAGGGCGTGAGCGTTGAGAAGTCCTCAAGTAGCTTCCTGATGGTAGTG
GGCGTCATTAACACCGACGGCACCATGACCCAGGAGGATATTTCGGATTACGTTGCCGCCAATATGAAAG
ATCCGATCAGCCGTACCTCTGGGGTGGGCGACGTCCAGCTGTTTGGTTCGCAATATGCGATGCGTATCTG
GATGAATCCGACAGAGCTGACCAAATACCAACTGACGCCGGTCGACGTGATTAACGCGATCAAAGCGCAG
AACGCCCAGGTCGCGGCAGGTCAGCTCGGTGGTACGCCGCCGGTTAAAGGCCAGCAGCTTAACGCATCGA
TTATTGCCCAAACGCGTCTGACCTCAACGGATGAGTTTGGCAAAATCCTGCTGAAAGTGAATCAGGATGG
CTCCCAGGTTCGTCTGCGGGATGTAGCGAAAATTGAGCTTGGCGGCGAGAACTACGACGTCATTGCGAAA
TTTAACGGTCAGCCAGCGTCAGGTCTTGGCATCAAACTGGCTACCGGCGCCAACGCGCTGGATACCGCTA
CCGCTATTCGTGCCGAACTGAAAAAATGGAACCGTTCTTCCCGCCAGGGATGAAAATCGTCTACCCGTA
TGACACCACGCCGTTCGTGAAGATCTCTATTCATGAAGTGGTAAAAACGCTGGTCGAAGCGATTATCCTC
GTGTTCCTGGTGATGTACCTGTTCCTGCAGAACTTCCGCGCGACGTTGATTCCGACTATTGCGGTTCCGG
TGGTGTTGTTGGGAACCTTTGCCGTGCTTGCGGCATTCGGTTTCTCGATAAACACGCTGACGATGTTCGG
GATGGTGCTCGCCATCGGCTTGCTGGTGGATGACGCCATCGTGGTGGTCGAGAACGTCGAACGTGTTATG
ACGGAAGAAGGCCTTCCGCCGAAGGAAGCGACGCGCAAATCCATGGGCCAGATTCAGGGCGCATTGGTGG
GTATCGCGATGGTACTGTCGGCGGTATTTATTCCGATGGCCTTCTTTGGCGGCTCAACCGGGGCAATTTA
TCGTCAGTTCTCTATCACCATCGTATCGGCGATGGCGCTGTCGGTGCTGGTCGCGCTGATCCTGACGCCT
GCGCTGTGCGCGACGATGCTCAAACCCGTCGCCAAAGGCGATCATGGCGAAGGGAAAAAAGGCTTTTCG
GCTGGTTTAACCGCCTGTTTGATAAGAGCACGCATCACTACACCGATAGCGTAGGCAATATTCTGCGCAG
CACCGGGCGTTATCTGCTGCTCTATCTCATTATCGTCGTCGGTATGGCTTATCTGTTCGTTCGTCTGCCA
AGCTCTTTCTTGCCGGATGAAGACCAGGGCGTATTCCTGACAATGGTCCAGCTCCCCGCGGGCGCAACGC
AAGAGCGCACGCAAAAAGTGCTGGATGAGGTCACGGATTACTATCTGAACAAAGAGAAAGCCAACGTTGA
ATCGGTATTCGCCGTCAACGGCTTCGGTTTTGCAGGGCGCGGTCAGAATACCGGTATTGCATTCGTGTCG
TTGAAAGACTGGGCCGATCGTCCAGGCGAAAAAAACAAGGTTGAAGCGATTACCCAGCGGGCAACCGCAG
CGTTTTCACAAATTAAAGATGCGATGGTCTTCGCCTTTAACCTGCCGGCGATCGTTGAGCTGGGCACCGC
AACCGGCTTTGACTTCGAGTTGATTGACCAGGCGGGACTTGGTCATGAAAAACTCACCCAGGCACGTAAT
CAGTTGTTCGGCGAGGTGGCGAAATATCCTGATCTGCTGGTCGGCGTTCGACCTAACGGTCTGGAAGATA
CGCCGCAGTTTAAAATCGATATCGACCAGGAAAAAGCTCAGGCGCTGGGCGTATCTATTAGCGACATTAA
TACCACGCTGGGCGCAGCATGGGGCGGCAGCTATGTAAACGACTTTATCGATCGCGGTCGTGTGAAGAAA
GTTTACGTGATGTCCGAAGCGAAATACCGCATGTTGCCGGATGATATTAACGACTGGTACGTTCGTGGTA
GCGATGGTCAGATGGTGCCATTCTCCGCATTCTCCTCTTCCCGCTGGGAATATGGTTCGCCGCGTCTGGA
ACGCTATAACGGTCTGCCTTCGATGGAAATTCTGGGGCAGGCGGCGCCAGGCAAGAGTACCGGTGAAGCG
ATGGCGATGATGGAAGAACTGGCCAGCAAGCTGCCGTCAGGCATTGGGTATGACTGGACCGGGATGTCCT
ACCAGGAGCGGTTGTCCGGCAACCAGGCCCCTGCCCTGTATGCTATATCGCTGATCGTCGTCTTCCTGTG
TCTGGCGGCATTGTATGAGAGCTGGTCTATCCCGTTCTCCGTAATGCTGGTTGTTCCGCTTGGGGTTATC
GGCGCGCTGCTGGCTGCGACCTTCCGCGGACTGACTAACGACGTTTACTTCCAGGTGGGCCTGCTCACAA
CCATTGGGTTGTCGGCGAAGAACGCGATACTTATCGTCGAATTCGCCAAAGACTTAATGGATAAAGAAGG
GAAAGGTCTGGTAGAAGCGACGCTGGAGGCCGTCCGGATGCGTTTGCGCCCGATTCTGATGACCTCGTTA
GCGTTCATGCTGGGGGTTATGCCGCTGGTTATCAGTTCCGGCGCGGGTTCCGGCGCGCAGAATGCGGTAG
GTACTGGCGTACTGGGCGGGATGGTAACGGCAACCGTACTGGCTATTTTCTTCGTACCGGTCTTCTTCGT
GGTGGTACGCCGCCGCTTTAGCCGTAAAAGCGAAGATATTGAGCATAGTCATTCGACAGAACATCGCTGA
(SEQ ID NO: 3)
```

*acrD* gene

```
ATGGCGAATTTTTTTATCGATCGCCCCATTTTTGCCTGGGTGCTGGCTATCCTGTTGTGTCTGACAGGGG
CGTTAGCCATTTTCTCTTTACCTGTTGAACAATATCCCGATCTGGCGCCGCCCAACGTACGTATTACCGC
GAATTATCCGGGAGCGTCGGCGCAAACGCTGGAAAATACCGTAACCCAGGTTATTGAGCAGAATATGACG
GGCCTCGATAATCTGATGTACATGTCATCACAAAGCAGCGGAACCGGACAGGCGACCATCACCCTGAGCT
TTATTGCGGGAACCGATCCTGATGAGGCGGTTCAGCAGGTGCAAAACCAGTTACAGTCCGCGATGCGTAA
ACTGCCGCAGGCGGTACAGGATCAAGGCGTCACGGTACGCAAAACGGGCGATACCAATATTTTGACCATC
GCTTTCGTCTCTACCGACGGTTCTATGGACAAGCAGGATATCGCCGACTACGTCGCCAGTAATATTCAGG
ACCCGCTCAGCCGCGTCAACGGCGTCGGCGATATTGACGCTTATGGTTCACAGTACTCTATGCGTATCTG
GCTCGATCCGGCCAAATTGAATAGTTTTCAGATGACCACGAAAGACGTGACCGATGCAATTGAGTCGCAG
AATGCGCAAATCGCCGTCGGGCAGCTTGGCGGTACGCCTTCGGTCGACAAACAGGCGCTGAACGCCACCA
TTAATGCGCAGTCATTGCTGCAAACGCCGCAACAATTTCGCGATATCACCCTGCGCGTTAATCAGGACGG
TTCCGAGGTCAAACTGGGCGATGTCGCCACCGTGGAGCTGGGGGCGGAAAAGTATGACTACCTCAGCCGT
TTTAACGGCAATCCGGCTTCCGGTCTTGGCGTTAAGCTGGCCTCCGGCGCGAACGAAATGGCGACCGCGA
AGCTGGTACTGGATCGCCTCAACGAGCTGGCGCAGTACTTCCCTCACGGCCTGGAATACAAGATCGCGTA
TGAAACCACCTCCTTTGTCAAAGCCTCGATTATCGATGTGGTCAAAACGTTGCTGGAAGCTATCGCGCTG
GTTTTCCTGGTGATGTATCTGTTCCTGCAAAACTTTCGCGCCACGCTCATTCCGACGATCGCCGTGCCGG
TAGTATTAATGGGCACCTTCTCCGTGCTTTACGCGTTTGGCTACAGTATTAACACATTAACCATGTTCGC
GATGGTGCTGGCGATCGGGCTCCTAGTCGACGATGCCATCGTGGTGGTGGAAAACGTCGAACGTATCATG
AGCGAAGAAGGGCTCACGCCGCGTGAAGCGACGCGCAAATCCATGGGACAAATCCAGGGGGCGCTGGTCG
GTATCGCGATGGTGCTGTCTGCGGTATTCGTGCCGATGGCGTTCTTTGGCGGTACCACCGGGGCGATTTA
TCGTCAGTTTTCTATTACCATTGTCTCGGCAATGGTGCTGTCGGTGCTGGTCGCCATGATCCTGACGCCG
GCGCTGTGCGCAACGTTATTAAAACCGCTGCACAAAGGCGAACAGCACGGGCAACGCGGATTTTTCGGCT
GGTTTAACCGTACCTTCAATCGTAATGCCGAACGTTATGAGAAAGGCGTAGCGAAAATTTTGCATCGCAG
CCTGCGCTGGATTCTGATTTATGTTCTGTTACTTGGCGGAATGGTGTTCCTGTTTTTGCGCCTCCCCACC
TCCTTTCTGCCGCAGGAAGATCGGGGCATGTTCACTACGTCTATCCAGCTACCGAGCGGTTCTACGCAAC
AGCAGACCCTGAAAGTCGTTGAAAAGGTTGAAAACTATTACTTCACCCATGAGAAAGACAACATTATGTC
GGTCTTCTCGACGGTAGGTTCCGGCCCTGGCGGGAATGGGCAAAACGTCGCGCGCATGTTTGTTCGCTTG
AAAGACTGGGACGCGCGCGATCCCACCACCGGCTCCTCGTTCGCCATTATTGAGCGGGCGACAAAAGCAT
TTAACCAGATTAAAGAAGCTCGCGTCTTCGCCAGCAGCCCGCCGGCAATTAGCGGTCTGGGCAGCTCCGC
CGGTTTTGATATGGAATTACAGGATCACGCCGGAGCAGGCCATGACGCGCTGATGGCCGCACGAGATCAA
CTCATTGAGCTGGCCGGGAAAAACAGTTCCTTGACCCGCGTGCGCCACAACGGCCTGGACGACAGCCCGC
AACTGCAAATTGATATTGACCAACGAAAGCGCAGGCGCTGGGCGTATCGATTGACGATATCAACGACAC
CCTGCAAACAGCCTGGGGATCGAGCTACGTCAACGACTTTATGGACCGGGGCCGCGTGAAGAAGGTCTAT
GTTCAGGCCGCAGCGAAATATCGTATGTTGCCGGATGATATTAATCTTTGGTATGTCCGTAACAAAGACG
GCGGCATGGTCCCCTTCTCCGCCTTCGCCACCTCGCGCTGGGAAACCGGATCGCCGCGTCTGGAACGCTA
TAACGGCTATTCGGCGGTAGAAATTGTCGGAGAGGCCGCGCCGGGGGTCAGTACCGGGACGGCAATGGAT
GTCATGGAGTCGTTGGTGCATCAGCTACCGGGCGGTTTTGGCCTGGAATGGACAGCCATGTCTTACCAGG
AACGGCTCTCCGGCGCGCAGGCGCCCGCGCTGTACGCTATTTCGCTATTAGTCGTCTTCCTGTGTCTGGC
GGCATTGTATGAAAGCTGGTCGGTGCCCTTCTCGGTGATGCTGGTTGTGCCGCTCGGGGTCATCGGCGCG
CTACTCGCTACCTGGATGCGCGGGCTGGAAAACGATGTTTACTTCCAGGTGGGGCTGTTGACCGTTATCG
GCCTCTCGGCGAAAAACGCGATTCTGATTGTGGAATTCGCCAACGAAATGAATCAGAAGGGACACGCGCT
GTTAGACGCCACGCTGTACGCCAGCCGCCAACGCCTGCGACCGATACTGATGACTTCGCTGGCGTTTATC
TTTGGCGTATTGCCGATGGCCACCAGCACCGGGGCAGGCTCGGGTAGCCAACATGCTGTCGGAACCGGCG
TGATGGGGGGAATGATCTCAGCAACCGTTCTGGCTATCTTCTTTGTACCCCTGTTTTTCGTGCTGATACG
TCGCCGCTTCCCGCTGAAGCCGCGCCCGAAATAA (SEQ ID NO: 4)
```

FIGURE 6 - continued

***acrF* gene**

ATGGCAAACTTTTTTATTAGACGTCCTATTTTCGCCTGGGTTCTGGCCATTATCCTGATGATGGCTGGCG
CACTGGCAATAATGCAACTTCCCGTTGCGCAGTATCCAACCATTGCGCCGCCAGCGGTTTCTATTTCTGC
AACCTATCCTGGCGCGGATGCGCAGACGGTACAGGATACGGTTACTCAGGTTATCGAACAAAATATGAAC
GGTATCGATAACCTGATGTATATGTCCTCTACCAGCGACTCTGCTGGTAGCGTGACCATCACCCTGACCT
TCCAGTCCGGAACCGATCCGGATATCGCGCAGGTTCAGGTGCAAAATAAATTGCAGCTCGCCACGCCTTT
ACTGCCGCAAGAAGTCCAGCAGCAGGGGATTAGCGTTGAAAAATCCAGCAGCAGCTTTTTGATGGTCGCC
GGGTTCGTCTCAGATAATCCGAACACTACCCAGGACGACATCTCTGACTATGTCGCCTCTAACATTAAGG
ATTCTATCAGCCGTCTGAATGGTGTGGGCGACGTTCAGCTATTTGGCGCACAGTACGCCATGCGTATCTG
GCTGGATGCGAATCTGCTAAATAAATACCAGCTCACGCCAGTTGACGTCATCAACCAGTTAAAAGTACAG
AACGACCAGATTGCGGCAGGCCAACTGGGCGGCACGCCAGCATTACCGGGCCAGCAGCTTAACGCCTCAA
TCATCGCCCAAACGCGTCTGAAAGATCCGGAAGAGTTCGGCAAAGTTACGTTGCGCGTCAATACCGACGG
CTCTGTCGTCCATCTCAAAGATGTCGCGCGTATTGAGCTTGGCGGTGAAAACTATAACGTTGTAGCGCGC
ATTAACGGTAAACCGGCCTCCGGTCTCGGTATTAAACTGGCGACCGGCGCTAACGCGCTGGATACCGCAA
CCGCAATCAAAGTGAAACTGGCGGAGCTGCAGCCTTTCTTCCCTCAGGGAATGAAGGTGGTTTATCCTTA
TGACACAACGCCCTTCGTAAAAATATCTATCCACGAAGTGGTAAAAACGCTGTTTGAAGCGATTATTCTG
GTGTTCCTGGTAATGTATCTGTTCTTACAGAATATCCGGGCAACCCTGATTCCTACCATCGCTGTTCCTG
TCGTGTTGCTAGGCACTTTTGCGGTACTCGCCGCCTTTGGCTATTCCATCAATACCCTGACGATGTTTGG
TATGGTACTGGCGATAGGGCTGTTGGTTGACGATGCGATAGTGGTCGTAGAAAACGTTGAACGTGTAATG
ATGGAGGATAACCTTTCTCCCCGAGAGGCGACGGAAAAATCCATGTCGCAGATTCAGGGAGCGCTGGTTG
GTATCGCGATGGTACTGTCTGCGGTATTTATCCCGATGGCCTTTTTGGCGGCTCGACCGGGGCAATTTA
TCGCCAGTTCTCTATTACTATTGTTTCAGCAATGGCGCTATCCGTTCTGGTTGCGTTGATTCTGACGCCA
GCACTGTGCGCTACGCTGCTTAAACCCGTATCTGCTGAACATCACGAGAAAAAAGCGGCTTCTTTGGCT
GGTTCAATACCAGGTTTGACCACAGCGTTAACCACTATACTAACAGCGTAAGCGGCATCGTGCGTAATAC
GGGTCGCTATCTCATTATCTATCTACTTATTGTAGTCGGAATGGCGGTTCTGTTTTACGCCTCCCGACC
TCCTTCCTGCCGGAAGAAGATCAGGGAGTATTCCTGACCATGATTCAGCTCCCCTCTGGCGCTACGCAAG
AACGTACGCAGAAAGTGCTGGATCAAGTCACTCATTACTACCTGAATAATGAAAAGCGAACGTCGAAAG
CGTGTTTACCGTAAACGGCTTTAGCTTTAGCGGTCAGGGACAAAACTCAGGGATGGCATTTGTCAGCCTT
AAACCCTGGGAAGAGCGTAACGGTGAAGAAAATAGCGTCGAAGCCGTTATCGCCAGAGCGACACGCGCCT
TTAGCCAGATTCGCGACGGGTTGGTGTTCCCCTTCAACATGCCGGCAATTGTCGAGTTAGGTACCGCAAC
AGGTTTCGACTTCGAACTGATTGATCAGGGAGGACTCGGTCACGATGCGTTAACAAAAGCGCGTAATCAA
CTCCTGGGTATGGTCGCGAAGCATCCTGATCTATTAGTGCGCGTACGCCCGAACGGGCTGGAAGACACGC
CACAGTTCAAGCTGGATGTCGATCAAGAAAAAGCGCAGGCGCTCGGCGTTTCGCTGTCTGATATCAACGA
AACCATCTCCGCGGCGTTGGGCGGCTATTACGTTAACGACTTTATCGATCGCGGACGAGTGAAAAAAGTA
TACGTTCAGGCTGACGCTCAGTTCCGTATGCTGCCGGGAGATATCAACAATCTTTATGTTCGCAGCGCTA
ATGGCGAGATGGTGCCCTTCTCTACCTTTAGCTCAGCACGGTGGATTTATGGTTCGCCACGCCTGGAACG
CTATAACGGGATGCCGTCAATGGAACTGCTCGGCGAAGCAGCACCCGGACGAAGCACCGGTGAAGCCATG
TCGTTAATGGAAAACCTGGCTTCACAGCTACCAAACGGTATTGGCTATGACTGGACAGGTATGTCGTATC
AGGAACGGTTGTCAGGTAACCAGGCGCCGGCGCTGTACGCAATCTCACTCATTGTCGTTTTCCTCTGCCT
TGCCGCTCTGTATGAAAGCTGGTCAATTCCGTTCTCGGTAATGCTGGTCGTACCGCTCGGCGTGGTTGGC
GCTCTGCTTGCAGCGTCATTGCGCGGTCTGAACAATGACGTTTACTTCCAGGTTGGCTTGTTAACCACTA
TTGGCCTTTCTGCTAAAAACGCCATCCTGATTGTCGAGTTCGCCAAAGATCTCATGGAAAAGAAGGACG
TGGATTGATTGAAGCGACGCTGGAAGCATCCCGTATGCGTTTACGTCCTATTCTAATGACCTCGCTGGCC
TTTATTCTCGGGGTAATGCCGTTAGTTATCAGTCGTGGCGCAGGTAGTGGTGCACAGAACGCAGTAGGCA
CAGGGGTTATGGGGGGAATGTTAACCGCAACCTTATTAGCTATCTTCTTCGTGCCGGTATTCTTCGTTGT
TGTAAAACGCCGATTTAATCGCCATCATGATTAA (SEQ ID NO: 5)

FIGURE 6 - continued

*acrE* gene

ATGACGAAACATGCCAGGTTTTCACTCCTGCCCTCATTCATCATATTCTCTGCTGCGCTGCTGGCCGGTT
GTAATGACCAGGGAGATACCCAGGCTCATGCCGGCGAGCCGCAAGTCACCGTCCATGTGGTCGAAACAGC
GCCGCTAGCCGTAACGACCGAACTTCCCGGACGTACGTCCGCATTTCGCATTGCGGAGGTTCGCCCCCAG
GTGAGCGGGATCGTGCTTAAAAGAAACTTCACCGAAGGTAGCGATGTAGAGGCCGGGCAGTCGCTCTATC
AGATCGATCCTGCCACTTATCAGGCTGATTATGACAGCGCTAAAGGCGAACTTGCTAAAAGCGAAGCGGC
TGCGGCTATCGCGCACCTGACGGTCAAACGCTATGTTCCACTGGTCGGCACAAAATATATCAGCCAACAG
GAATATGATCAGGCGATTGCCGACGCCCGCCAGGCCGATGCCGCCGTTGTGGCGGCAAAAGCCGCTGTTG
AAAGCGCGCGTATTAACCTTGCGTATACCAAAGTCACCTCACCCATCAGCGGGCGTATAGGAAAATCTAA
TGTGACTGAAGGCGCGCTGGTGACTAATGGTCAGTCAACTGAACTGGCTACCGTGCAACAACTCGATCCG
ATTTATGTCGACGTGACGCAATCAAGCAACGACTTTATGCGACTCAAGCAATCCGTCGAACAAGGTAACC
TGCATAAAGACAGCGCCAGTAGCACGGTTCAACTGGTAATGGAAAATGGTCAGGTCTACCCGATTAAAGG
CACGCTGCAATTTTCCGACGTTACCGTAGATGAAAGCACCGGCTCTATCACGCTCAGGGCGGTGTTCCCT
AACCCGCAACACAGTCTGCTTCCCGGTATGTTTGTTCGCGCCCGCATTGATGAAGGCGTCCAGCCCAATG
CCATCCTTGTCCCCAGCAGGGCGTAACCCGCACGCCGCGCGGCGACGCAATGGTGATGGTGGTTAACGA
TAAAAGCCAGGTCGAAGCCCGCAATGTCGTGGCGGCGCAGGCTATTGGCGATAAATGGCTCATCAGCGAA
GGGTTAAAACCGGGCGATAAGGTCATCGTCAGCGGCTTACAAAAAGCGCGACCGGGCGTCCAGGTGAAAG
CCACTACCGATGCTCCTGCAGCGAAAACGGCGCAATAA (SEQ ID NO: 6)

*mdtA* gene

ATGAAAGGCAGTAATACTTTCCGCTGGGCAATAGCGATTGGGGTTGTAGTGGCCGCCGCCGCATTCTGGT
TCTGGCATAGCCGTAGCGAAAGCCCGACCGCCGCGCCAGGCGTCGCCGCGCAAGCGCCGCATACCGCCTC
CGCAGGTCGCCGCGGTATGCGCGACGGCCCTCTGGCGCCGGTACAGGCCGCGACCGCGACCACGCAGGC
CGTACCGCGCTATCTGAGCGGGCTGGGTACCGTGACCGCCGCGAATACCGTTACGGTGCGTAGCCGCGTG
GATGGTCAACTCATCGCCCTGCACTTTCAGGAAGGTCAGCAGGTCAACGCAGGCGATCTGCTGGCGCAAAT
CGATCCCAGCCAGTTTAAGGTCGCCCTGGCGCAGGCTCAGGGACAGTTGGCGAAAGATAACGCTACGCTG
GCGAATGCGCGTCGTGATCTGGCGCGCTATCAGCAACTGGCAAAAACCAATCTGGTTTCCCGTCAGGAAC
TGGATGCGCAACAGGCGCTGGTCAACGAAACCCAGGGAACCATTAAAGCGGATGAAGCTAATGTCGCCAG
CGCGCAGTTACAGCTCGACTGGAGTCGTATCACGGCCCCGGTCTCGGGACGCGTGGGTCTGAAACAGGTG
GATGTCGGCAACCAGATTTCCAGCAGCGATACCGCAGGTATTGTCGTCATTACGCAAACGCACCCGATTG
ATCTCATTTTTACTCTGCCGGAAAGCGATATCGCGACCGTAGTTCAGGCACAGAAAGCGGGGAAAGCGCT
GGTCGTAGAAGCCTGGGATCGGACTAACTCGCACAAATTGAGCGAAGGTGTGTTGCTCAGTCTGGACAAC
CAGATTGATCCCACGACGGGAACGATCAAAATTAAAGCGCGCTTTACCAATCAGGACGATACGCTGTTCC
CCAATCAATTTGTGAACGCCCGGATGCTGGTCGATACCGAACAAAATGCCGTTGTGGTGCCTGCCGCGGC
GGTGCAAATGGGCAATGAGGGCACTTTGTGTGGGTGCTGAACGACGAAAATAACGTCAGCAAGAAGCGG
GTAAAAATCGGTATTCAGGATAACCGAAACGTGGTGATCAGCGCAGGCTTATCGGCAGGCGATCGCGTCG
TTACCGATGGTATTGATCGGCTGACGGAAGGCGCAAAAGTCGAGGTCGTTGAGCCGCAAACCACCGTGGC
GGATGAAAAATCCCCTTCCCGCCATGAAGGTCAAAAAGGAGCGCGCGCCTGA (SEQ ID NO: 7)

FIGURE 6 - continued mdtB gene

```
ATGCAGGTATTACCTCCGGGCAGCACGGGCGGCCCTTCGCGTCTGTTTATTCTGCGCCCCGTGGCCACCA
CTCTGCTGATGGCGGCGATTTTACTCGCCGGGATTATCGGCTATCGCTTCCTGCCCGTCGCCGCTTTGCC
GGAGGTCGACTACCCCACTATTCAGGTTGTTACGCTCTACCCTGGCGCCAGCCCGGATGTCATGACCTCC
GCCGTCACCGCGCCGCTTGAGCGCCAGTTCGGCCAGATGTCAGGACTGAAGCAGATGTCGTCGCAAAGCT
CCGGCGGCGCGTCAGTGGTAACGCTACAGTTTCAGTTGACGCTGCCGCTGGACGTTGCCGAGCAGGAAGT
ACAGGCGGCGATTAACGCAGCCACCAATTTATTGCCTTCCGACCTGCCGAATCCGCCGATTTACAGCAAA
GTCAATCCGGCGGACCCGCCGATTATGACGCTTGCCGTCACCTCAAACTCGATGCCGATGACCCAGGTAG
AGGACATGGTAGAAACCCGCGTGGCGCAGAAGATCTCACAGGTCTCCGGCGTCGGGCTGGTGACGCTTGC
CGGCGGGCAGCGCCCTGCGGTACGCGTAAAACTGAATGCTCAGGCTGTCGCCGCGCTCGGTCTGACCAGC
GAAACGGTCCGTACCGCAATTACCGGCGCCAACGTCAACTCGGCGAAAGGCAGTCTGGATGGCCCCGAAC
GGGCGGTGACGCTTTCTGCTAACGATCAGATGCAGTCTGCCGACGAATACCGCAGGCTTATCATCGCGTA
TCAAAACGGCGCGCCGGTACGGCTGGGCGATGTCGCCACCGTCGAACAGGGGGCGGAAAATAGCTGGCTC
GGCGCATGGGCGAATCAAGCGCCGGCTATCGTGATGAACGTTCAACGCCAGCCTGGCGCCAATATCATTG
CGACAGCGGACAGCATTCGCCAGATGCTGCCCCAGCTTACCGAAAGCCTGCCAAAATCGGTGAAGGTCAC
GGTCCTGTCCGATCGCACCACCAATATTCGCGCTTCCGTGCGCGATACCCAGTTTGAACTGATGCTGGCG
ATCGCGCTGGTCGTCATGATTATCTATCTGTTTTTACGTAATATTCCCGCCACAATTATTCCCGGCGTCG
CCGTACCGCTGTCGCTTATCGGCACCTTTGCGGTGATGGTGTTTTGGATTTTTCCATTAATAACCTGAC
GCTGATGGCGCTCACTATCGCCACGGGTTTCGTGGTGGACGATGCGATTGTGGTGATCGAGAACATCTCG
CGCTACATCGAAAAAGGAGAAAAACCGCTGGCGGCGGCGCTCAAAGGCGCGGGTGAAATCGGCTTTACCA
TTATTTCCCTCACCTTTTCACTGATTGCGGTGCTGATCCCGTTGCTCTTTATGGGCGATATTGTTGGTCG
ACTGTTCCGCGAATTTGCGGTGACGTTGGCGGTAGCGATTTTAATCTCCGCCGTCGTCTCTTTGACGCTC
ACGCCCATGATGTGCGCGCGTATGCTCAGCCAGCAGTCTCTGCGTAAACAAAACCGCTTTTCCCGCGCCT
GCGAGCGGATGTTTGACCGCGTGATCGCCAGCTACGGACGTGGATTAGCGAAAGTGCTCAACCATCCGTG
GCTTACATTGAGCGTGGCATTCGCCACGCTCCTGCTCAGCGTTATGCTGTGGATAGTCATTCCGAAAGGG
TTCTTTCCGGTACAGGATAACGGCATTATCCAGGGAACGCTGCAGGCGCCGCAATCGTCATCGTATGCCA
GTATGGCGCAACGTCAGCGCCAGGTGGCGGAGCGGATATTACAGGACCCGGCGGTGCAAAGCCTGACGAC
TTTTGTTGGCGTAGACGGCGCTAACCCCACGCTGAATAGCGCGCGCCTGCAAATTAACCTCAAGCCGCTG
GATGCGCGTGATGACCGCGTGCAGCAGGTGATCTCCCGGCTGCAAACCGCCGTGGCGACGATTCCGGCG
TGGAGCTGTATCTCCAGCCGACGCAGGATTTAACCATCGACACGCAGGTCAGCCGCACACAGTATCAGTT
TACCCTGCAGGCCACGACGCTCGATGCGCTCAGCCACTGGGTGCCAAAACTGCAGAACGCGCTACAGTCG
TTGCCACAGCTCTCTGAGGTAAGCAGCGACTGGCAAGATCGGGGATTAGCGGCCTGGGTGAATGTCGACC
GCGACAGCGCCAGCCGTCTGGGTATCAGCATGGCGGATGTGGATAACGCGCTCTACAACGCGTTCGGACA
ACGCCTGATTTCAACGATTTATACCCAGGCGAACCAGTACCGTGTCGTGCTGGAACATAATACCGCCAGC
ATGCCGGGCCTGGCGGCGCTGGAGACGATTCGCCTGACGAGCCGCGACGGCGGCACCGTACCGCTCAGC
GCGATTGCCCGCATTGAGCAGCGCTTCGCTCCGCTCTCCATCAATCATTTAGATCAGTTCCCGGTTACGAC
ATTTTCGTTTAACGTGCCGGAGAGCTATTCGCTCGGCGATGCGGTGCAGGCGATTCTCGATACGGAAAAA
ACGCTCGCCCTGCCAGCGGATATTACAACGCAGTTTCAGGGTAGTACGCTCGCCTTCCAGGCGGCGCTAG
GCAGCACCGTCTGGCTTATTGTCGCCGCCGTGGTGGCGATGTATATCGTGCTCGGCGTGCTGTATGAGAG
TTTTATCCATCCGATTACGATTCTCTCAACGCTGCCTACGGCGGGCGTCGGCGCGCTGCTGGCGCTGATC
ATCGCTGGTAGCGAGCTCGATATTATCGCCATTATCGGCATTATTTTGCTGATCGGCATCGTGAAGAAAA
ACGCCATCATGATGATTGACTTCGCCCTCGCCGCCGAACGCGAACAGGGGATGAGTCCGCGCGACGCTAT
CTTCCAGGCCTGTCTGCTGCGTTTTCGACCGATTCTGATGACCACGCTGGCGGCGTTGCTCGGGGCATTG
CCATTAATGTTGAGTACCGGCGTTGGCACGGAATTACGTCGCCCGTTGGGGATCGCGATGGTAGGCGGCT
TACTGGTCAGCCAGGTATTAACTCTGTTTACCACACCGGTGATTTATCTCCTGTTTGACCGCCTGTCGCT
GTACGTGAAAAGTCGCTTTCCGCGCCATAAAGAGGAGGCGTAG (SEQ ID NO: 8)
```

FIGURE 6 - continued mdtC gene

ATGCGCTTTTTCGCCCTTTTCATCTACCGCCCGGTCGCCACCATTTTGATTGCCGCCGCCATTACGCTGT
GCGGCATTCTGGGCTTTCGTCTGCTGCCGGTCGCCCCGCTGCCGCAGGTCGATTTCCCGGTGATTATGGT
TAGCGCCTCGCTGCCGGGCGCCTCGCCGGAAACCATGGCTTCGTCGGTGGCGACGCCGTTGGAACGCTCT
TTGGGACGCATTGCAGGCGTCAATGAAATGACCTCCAGCAGCTCGCTCGGCAGTACACGCATTATTCTCG
AATTTAATTTCGATCGTGATATTAACGGCGCGGCGCGCGACGTGCAGGCCGCCATTAACGCCGCGCAAAG
CTTGTTGCCAGGCGGAATGCCCAGCCGCCCGACTTATCGCAAGGCCAACCCGTCCGACGCGCCGATTATG
ATTTTAACGCTTACCTCGGAGAGCTGGTCACAGGGCAAACTGTATGATTTCGCCTCTACCCAACTGGCGC
AAACCATCGCGCAAATTGACGGCGTCGGCGATGTTGACGTCGGCGGCAGCTCCCTGCCCGCAGTACGTGT
AGGCTTAAACCCGCAGGCGCTCTTTAACCAGGGCGTCTCGCTGGATGAGGTCCGCGAAGCGATCGACAGC
GCCAACGTACGCCGACCGCAAGGCGCAATTGAAGATAGCGTCCACCGCTGGCAAATCCAGACCAACGACG
AACTGAAAACCGCCGCCGAATATCAGCCGCTGATTATTCACTATAACAACGGCGCGGCGGTACGCCTGGG
CGACGTCGCCAGCGTCACCGACTCGGTGCAGGATGTCCGTAACGCCGGGATGACGAACGCTAAACCCGCT
ATTTTGTTGATGATCCGCAAGCTGCCGGAGGCCAATATTATTCAGACGGTCGACGGCATCCGGGCAAAAC
TGCCGGAACTGCGGGCAATGATCCCCGCCGCTATCGATTTACAAATCGCCCAGGATCGTTCGCCGACGAT
TCGCGCATCGCTGCAAGAGGTAGAAGAGACACTGGCTATCTCTGTTGCGCTGGTGATCCTGGTGGTGTTT
TTATTCCTGCGCTCCGGGCGCGCCACGCTAATTCCCGCCGTCGCCGTTCCCGTTTCGCTCATCGGCACCT
TCGCCGCCATGTATCTGTGCGGCTTCAGCCTCAACAATCTGTCGCTGATGGCGCTGACTATCGCGACCGG
ATTTGTCGTTGATGATGCCATTGTGGTGCTGGAAAATATCGCCCGCCATCTGGAGGCGGGAATGAAACCT
TTGCAGGCGGCATTACAGGGTACGCGAGAAGTTGGGTTTACGGTCATCTCCATGAGTCTGTCGCTGGTGG
CGGTATTTCTGCCGCTGCTGTTAATGGGCGGCCTGCCAGGACGATTATTACGGGAATTCGCCGTTACCCT
CTCGGTGGCGATTGGCATTTCGCTGGTGGTCTCGCTCACGCTGACGCCGATGATGTGCGGCTGGATGCTT
AAATCAAGCAAACCGCGCACCCAACCGCGTAAACGGGGCGTTGGCCGTCTGCTGGTCGCCTTGCAACAGG
GTTACGGCACGTCATTAAAATGGGTGCTTAACCATACGCGTCTTGTCGGTGTGGTTTTTCTTGGCACCGT
TGCGCTGAACATCTGGCTTTATATCGCCATCCCTAAAACATTCTTTCCGGAGCAGGACACCGGCGTGTTG
ATGGGCGGTATTCAGGCTGACCAAAGCATCTCTTTCCAGGCCATGCGCGGCAAGCTGCAGGATTTTATGA
AAATTATTCGCGACGATCCGGCGGTGAATAATGTCACTGGTTTTACCGGCGGATCGAGGGTGAATAGCGG
CATGATGTTTATTACGCTGAAGCCGCGCGGCGAACGCAAAGAGACGGCGCAGCAAATCATTGATCGACTG
CGGGTCAAACTGGCAAAAGAACCTGGCGCCAGGCTGTTTCTGATGGCGGTACAGGATATTCGCGTCGGCG
GGCGGCAGGCTAACGCCAGTTACCAATATACGTTGCTGTCTGACTCTCTGGCGGCGCTGCGCGAATGGGA
GCCGAAAATACGCAAAGCGCTCTCGGCCCTGCCGCAACTGGCGGACGTAAACTCCGACCAGCAGGATAAC
GGCGCGGAGATGAACCTTATCTACGACCGCGACACCATGTCACGGCTGGGTATTGATGTTCAGGCCGCAA
ACAGTCTGTTAAATAATGCTTTCGGCCAGCGGCAAATTTCCACCATTTATCAGCCGATGAACCAGTATAA
AGTGGTGATGGAAGTCGATCCGCGCTATAGCCAGGATATCAGCGCGCTGGAGAAAATGTTCGTTATCAAC
CGTGACGGAAAAGCGATTCCCCTCTCTTATTTCGCCCAATGGCGGCCCGCCAATGCGCCGCTGTCGGTGA
ACCATCAGGGACTTTCCGCGGCGTCCACGATTGCCTTTAACCTGCCGACCGGCACATCGTTATCGCAGGC
GACAGAGGCCATTAATCGCACCATGACGCAGCTTGGCGTCCCCTCGACGGTACGCGGCAGTTTTCCGGA
ACGGCGCAAGTCTTCCAGCAGACCATGAATTCACAGCTTATTTTGATAGTGGCGGCGATCGCTACCGTCT
ACATTGTGCTGGGGATACTGTACGAAAGCTACGTCCATCCACTGACCATTCTCTCTACTCTGCCATCGGC
GGGCGTTGGGGCGCTTCTGGCGCTGGAACTCTTCAATGCCCCTTTCAGCCTAATCGCCCTGATAGGGATC
ATGCTATTAATTGGCATTGTGAAGAAAAACGCCATTATGATGGTCGATTTTGCGCTTGAAGCGCAACGAA
GCGGCGGCCTGACGCCGGAACAAGCCATTTTCCAGGCCTGCTTGTTACGCTTCCGTCCAATAATGATGAC
CACGCTGGCGGCGCTGTTCGGCGCACTGCCATTGGTGTTATCTGGCGGAGACGGTTCGGAATTACGGCAG
CCGCTGGGGATAACCATTGTCGGCGGTTTGGTCATGAGCCAGCTCCTGACGCTCTATACCACGCCGGTGG
TGTACCTCTTTTTCGATCGTCTGCGGCTACGTTTTCGCGTAAAAATAGCAAACCGGTAGTAGAGATATG
A (SEQ ID NO: 9)

FIGURE 6 - continued

*mdsA* gene

ATGTTGATAGCCGGCGTCATCGCCGCCATCGGGGGCGTGATTTACATGGCCGGCGAAGCACTATGGGATA
AAGACAACGCCGTCGGCCCCCGGCCAGCGCGCCGCCTCCACCGTCGGTACCGGTTGCTAAAGCCCTTAG
CCGTACACTCGCGCCTACGGCGGAATTCACCGGTTTTCTGGCCGCGCCGGAAACCGTGGAGCTGCGTTCG
CGCGTGGGAGGAACCCTTGACGCCATCAGCGTTCCGGAAGGACGTCTGGTAAGCCGCGGACAACTGCTGT
TCCAGATCGATCCGCGCCCGTTCGAGGTCGCCCTCGACACCGCCGTCGCGCAATTACGTCAGGCTGAAGT
ACTGGCCCGCCAGGCGCAGGCGGATTTCGATCGCATTCAACGACTGGTCGCCAGCGGCGCCGTATCACGT
AAAAACGCTGACGATGTCACCGCCACGCGTAATGCGCGACAGGCGCAGATGCAATCGGCCAAAGCCGCCG
TCGCCGCAGCGCGCCTTGAACTCTCCTGGACCCGTATTACCGCGCCCATTGCCGGACGCGTTGACCGCAT
ACTGGTGACCCGGGGCAATCTGGTCAGCGGCGGCGTAGCGGGTAACGCCACGCTTCTGACGACTATCGTG
TCTCACAATCCCATGTATGTGTATTTCGATATTGACGAAGCCACCTGGCTGAAGGCGTTACGGCATACCC
GCTCCGACAAAAATCCACCGGTAGTCAACATGGGGTTAACCACCGATAACGGGCTGCCTTATCAGGGCGT
ACTCGACTTTATGGGCAATCAGATGAACCGCAGCACCGGCACTATCCGGGCACGCGCCGTGATTCCTGAC
CCCGACGGAATGCTTTCTCCCGGCCTGTTTGCCCGAATCAGTTTGCCCATCGGCGAGCCGCGGGAAACCG
TGCTGATTGACGATCTGGCGGTGAGCGCCGATCAGGGCAAAAACTATGTGCTGATCGTCGGCAAGGAGAA
TCAGGTGGAGTATCGTCCGGTTGAGTTGGGACAAATGGTCGATGGATTCCGCGTCGTTACACAGGGAGTA
CTGCCGGGAGAAAAAATCATCCTCAAGGGGCTGGTGCGTCCTGGCATGACCGTTGCGCCACGTCTGGTGC
CGATGCGGCAGAATGTGACCGACAAACAGACCGCGACATTGACTAAAGCGGACGGCGACAGTGCGCCGAA
GGCGGTGCGCCAATGA (SEQ ID NO: 10)

*mdsB* gene

ATGAAATTCACCCACTTTTTCATTGCACGCCCCATCTTCGCCATCGTCCTGTCGCTGTTAATGCTGCTGG
CTGGCGCTATCGCCTTTTTAAAACTGCCGCTGAGTGAATATCCGGCCGTTACGCCGCCCACGGTACAGGT
TAGCGCCAGCTACCCCGGCGCTAACCCGCAAGTGATTGCCGATACGGTAGCCGCGCCGCTGGAACAGGTG
ATCAACGGCGTTGACGGCATGTTGTATATGAATACCCAGATGGCCATTGATGGTCGCATGGTTATCTCTA
TCGCCTTCGAACAGGGAACCGATCCTGATATGGCGCAAATTCAGGTGCAAAACCGGGTATCCCGCGCGCT
GCCTCGCCTGCCCGAAGAAGTCCAGCGAATTGGCGTTGTAACGGAGAAAACGTCCCCGATATGTTGATG
GTGGTTCATCTTGTCTCGCCGCAAAAACGCTATGACTCGCTTTACCTGTCTAACTTCGCCATCCGGCAGG
TTCGCGACGAACTGGCCCGTTTACCCGGCGTGCGCGATGTTCTCGTCTGGGGCGCGGGCGAGTACGCCAT
GCGCGTCTGGCTGGACCCGGCGAAAATCGCCAACCGCGGTCTTACCGCCAGTGATATCGTTACGGCGTTG
CGGGAACAAAACGTACAGGTCGCCGCCGGTTCCGTCGGGCAACAGCCGGAGGCCTCCGCCGCTTTTCAGA
TGACGGTAAACACGCTGGGCCGCCTGACCAGCGAAGAACAGTTCGGCGAGATTGTGGTAAAAATCGGCGC
TGACGGCGAGGTGACGCGTCTGCGTGATGTCGCCCGCGTCACGCTGGGCGCAGATGCCTATACGCTGCGC
AGTTTACTGAATGGCGAAGCGGCGCCAGCGTTACAGATTATTCAAAGTCCGGGCGCCAATGCGATTGACG
TTTCTAACGCGATTCGCGGCAAAATGGATGAGTTGCAGCAAAACTTCCCGCAGGATATCGAATACCGGAT
TGCCTATGATCCTACGGTCTTCGTGCGCGCATCGCTACAATCGGTGGCGATTACGTTGCTGGAAGCCCTC
GTGCTGGTCGTCCTTGTCGTGGTGATGTTCCTGCAAACCTGGCGGGCGTCCATTATTCCTCTGGTGGCGG
TTCCCGTTTCGCTGGTCGGCACCTTTGCCTTGATGCACCTGTTTGGCTTTTCGCTGAATACGCTTTCGCT
GTTTGGTTTGGTCCTGTCGATAGGTATCGTTGTCGATGACGCCATCGTTGTGGTCGAAAACGTGGAACGG
CATATCTCGCAGGGCAAAAGTCCCGGAGAGGCGGCAAAGAAGGCGATGGATGAAGTCACTGGTCCCATTC
TTTCTATTACCTCGGTGCTAACGGCGGTCTTTATCCCTTCCGCATTCCTGGCGGGCCTGCAGGGTGAGTT
TTATCGTCAGTTCGCGTTGACCATCGCTATTTCGACCATCCTTTCGGCCATTAACTCGCTGACGCTCTCC
CCTGCGCTGGCTGCCATTTTGCTAAGACCGCACCACGATACTGCGAAGGCTGACTGGCTAACGCGGTTGA
TGGGCACGGTCACTGGCGGTTTTTCCATCGCTTTAACCGTTTCTTCGACAGCGCGTCGAACCGCTATGT
TAGCGCCGTCCGTCGGGCCGTGCGCGGCAGCGTCATTGTGATGGTGCTCTATGCTGGCTTTGTGGGCTG
ACCTGGCTTGGCTTCCATCAGGTGCCGAACGGGTTTGTGCCTGCGCAGGATAAATACTATCTCGTCGGCA
TCGCCCAGCTCCCAAGCGGCGCATCGTTGGATCGCACAGAGGCGGTCGTGAAACAGATGTCCGCTATCGC
GCTGGCGGAACCCGGCGTTGAAAGCGTCGTCGTCTTCCCCGGTCTGTCGGTTAACGGCCCGGTAAATGTG
CCAAATTCGGCGCTGATGTTCGCCATGCTGAAACCCTTTGACGAGCGTGAAGATCCTTCGCTTTCCGCTA
ACGCTATCGCCGGAAAGCTAATGCACAAATTTAGCCACATTCCCGACGGATTTATTGGCATCTTCCCGCC
ACCGCCGGTTCCAGGGCTTGGCGCGACGGGCGGCTTTAAATTGCAGATTGAAGATCGTGCGGAACTGGGA
TTTGAAGCGATGACAAAGGTGCAAAGCGAGATTATGTCTAAGGCGATGCAGACGCCCGAACTGGCCAATA
TGCTGGCCAGTTTCCAGACAAACGCCCCGCAATTACAGGTGGATATCGACCGGGTAAAGGCGAAATCAAT
GGGGGTATCGCTCACCGACATCTTTGAAACGTTGCAAATTAACCTCGGCTCGCTTTACGTCAACGATTTC

AACCGATTTGGCCGTGCCTGGCGGGTGATGGCGCAGGCCGATGCGCCATTCCGTATGCAGCAAGAGGATA
TCGGCCTGCTTAAAGTCCGCAATGCGAAGGGCGAGATGATCCCGCTTAGCGCTTTCGTCACGATTATGCG
CCAGTCGGGGCCGGACAGAATCATCCATTACAACGGCTTCCCCTCGGTAGATATTAGCGGTGGACCGGCT
CCGGGCTTCTCCTCCGGACAGGCGACGGACGCGATTGAAAAGATCGTGCGTGAAACGTTACCGGAAGGGA
TGGTCTTCGAATGGACCGATCTGGTTTATCAGGAAAAACAGGCCGGCAACTCTGCGCTTGCTATCTTTGC
GCTGGCGGTGCTGCTGGCCTTCCTGATCCTGGCGGCGCAGTACAACAGTTGGTCGCTGCCCTTCGCCGTC
CTGCTTATTGCGCCTATGTCATTACTCTCAGCCATTGTCGGCGTGTGGGTATCTGGCGGAGATAACAATA
TCTTTACGCAGATTGGTTTCGTGGTGCTGGTCGGCCTGGCGGCCAAGAACGCCATTTTGATTGTCGAGTT
TGCCCGCGCCAAAGAACACGACGGCGCAGACCCGCTGACCGCCGTACTGGAAGCGTCCCGCCTGCGTCTG
CGTCCTATCCTGATGACCTCATTCGCCTTTATCGCAGGTGTAGTACCACTGGTACTCGCGACGGGTGCCG
GCGCGGAAATGCGACATGCGATGGGCATCGCCGTGTTTGCCGGCATGTTGGGCGTCACGCTCTTCGGCCT
GTTATTGACGCCTGTATTTTACGTGGTGGTTCGCAGGATGGCATTAAAGCGTGAGAACCGCGTTGATTCG
CATGATCAGCAAGCATAA (SEQ ID NO: 11)

FIGURE 6 – continued

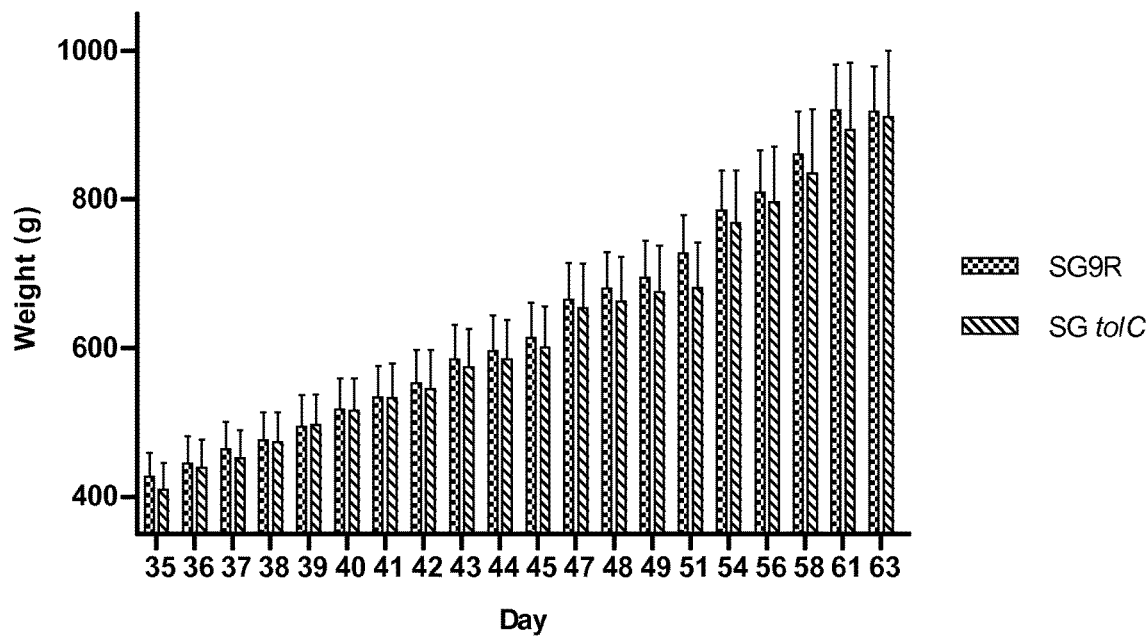

FIGURE 7

METHOD OF REDUCING EGG CONTAMINATION

FIELD OF THE INVENTION

The present invention relates to *Salmonella* mutant strains and their use as a vaccine for preventing *Salmonella* infection, in particular in eggs.

BACKGROUND OF THE INVENTION

*Salmonellosis* is a worldwide occurring disease caused by bacteria belonging to the genus *Salmonella*. *Salmonella enterica*, subspecies *enterica*, are Gram-negative bacterial pathogens that are comprised of more than 2500 different serovars, of which only a limited number are associated with poultry. *Salmonella enterica* serovar *Enteritidis* (S. *Enteritidis*; SE) and S. *Typhimurium* are generally accepted as the most important serovars in chickens, with respect to human public health significance. Chickens infected with the aforementioned serovars appear mainly asymptomatic and continue to shed the bacteria for long periods with rare cases of systemic disease, except in young chicks. However, these serovars are regularly associated with human infections, which mostly lead to a self-limiting gastrointestinal disease, and exposure to poultry or poultry products is one of the major risk factors for human infection. Majowicz et al. (2010) estimated in 2009 that 93.8 million cases of gastroenteritis due to *Salmonella* species occur globally each year, with 155,000 deaths. More than 80 million cases were supposed to be foodborne, and a considerable part of these infections were caused by the serotype *Enteritidis* and egg consumption. Infection with S. *Enteritidis* or S. *Typhimurium* can become severe, requiring antibiotic treatment or even hospitalization. Hence, a massive burden is still placed on both the poultry industry and the healthcare system. In addition, with the emergence of multidrug resistant *Salmonella* strains, antibiotic treatment for human patients is becoming increasingly difficult. Thus, there is definitely a need for effective measures to control the prevalence of non-host-adapted *Salmonella* species in poultry flocks.

Eggs are a main vehicle for the pathogen that causes spread to humans. *Salmonella* can be present on the shell surface due to the presence of *Salmonella* in the hen's environment or passage of the egg through the cloaca. In addition, the bacterium can also be contaminating internal eggs after reproductive tract colonization as a consequence of either shell penetration or colonization of the reproductive tract of laying hens and thus incorporation in the forming egg. In the latter case eggs are a 'box with *Salmonella* inside' that can't be eliminated using hygienic measures such as egg washing. Several lines of evidence however support the view that egg contamination with SE is more likely to take place during the formation of the egg in the reproductive organs than by eggshell penetration. The egg-associated pandemic reached a maximum in the mid 1990's to the early 2000's. In the European Union, legislation has been responsible for a serious reduction in *Salmonella* prevalence at laying hen farms, eggs and egg products and as a consequence human infections due to egg consumption. These legislations forced the member states to take action to monitor and control the pathogen, and reduction targets for prevalence have been produced. Over the past two decades, *Salmonella* control programs were implemented by the European Union, including that a) that antimicrobials cannot be used to control *Salmonella* b) that member states with a prevalence of *Salmonella Enteritidis* in commercial laying hens higher than 10% are mandatory to vaccinate and c) that live vaccines can only be used during rearing. Regulation No. 1237/2007 (Anonymous, 2007) laid down restrictions for the trade of table eggs from flocks infected with *Salmonella Enteritidis* or *Typhimurium*. The latter states that eggs from *Salmonella Enteritidis* or *Typhimurium* positive flocks must be banned from the market, unless they are treated in a manner that guarantees that all *Salmonella* bacteria are destroyed.

Despite the decline in human cases, *salmonellosis* still is the second most commonly reported zoonotic disease, following campylobacteriosis. Although eggs are no longer the primary food vehicle causing *salmonellosis*, it appears that when one considers the risk related to the different sources weighted according to the tonnage of food available for consumption, the risk of *Salmonella* infection still remains the highest when consuming table eggs (EFSA, 2013).

Vaccination of chickens, along with other control measures as part of a comprehensive *Salmonella* control program, is an important strategy in lowering the prevalence of *Salmonella*. Vaccination of chickens harnesses the immune system of the hosts to decrease the levels of *Salmonella* species that are associated with poultry flocks upon infection rather than control disease. The *Salmonella* vaccines that have been tested are divided into three categories: live attenuated, inactivated and subunit vaccines (Desin T et al., 2013). Although some commercially available vaccines are in the killed bacteria form, a few registered S. *Enteritidis* live vaccines are commercially available for poultry. These live vaccines are developed on the principle of either metabolic drift mutations or auxotrophic double-marker mutants obtained through chemical mutagenesis implicating a higher risk for reverting to virulence (Van Immerseel F et al., 2013). In addition, commercially available vaccines are developed with the focus on reducing shedding and colonization of host tissues such as spleen, liver and caeca, while it is known that *Salmonella* colonization in the reproductive tract is generally high and persistent. In several studies, SE was isolated from the reproductive tissue of infected birds, in the absence of intestinal colonization (Lister, 1988). It has been demonstrated that repeated in vivo passages through the reproductive tissues of chickens increase the ability of an SE strain to induce internal egg contamination, whereas serial passage through the liver and the spleen did not affect the ability of the strain to cause egg contamination (Gast et al., 2003). This is an indication that interaction of SE with the reproductive tissues may either induce or select for the expression of microbial properties important for egg contamination. SE is capable of persistence in reproductive tissues of naturally and experimentally infected hens, even though the animals generate an innate and adaptive immune response to the infection, indicating that the bacteria can reside intracellularly and escape the host defense mechanisms (Gantois et al., 2009). The deposition of *Salmonella* inside eggs is thus most likely a consequence of reproductive tissue colonization in infected laying hens (Keller et al., 1995; Methner et al., 1995; Gast & Holt, 2000a). WO2006129090 shows that vaccination of one-day old chicks with a S. *Typhimurium* tolC mutant strain results in a reduced shedding of the S. *Typhimurium* challenge strain together with a reduced colonization of liver and spleen tissues. However, WO2006129090 is completely silent on colonization of the reproductive tract and egg contamination. Studies documenting protection against egg contamination by vaccination of laying hens are limited (Gantois I et al., 2006). The efficacy of live vaccines in poultry has been tested in experimental and field studies but only a few studies have demonstrated a partial protective effect of immunization against egg contamination (Miyamoto T et al., 1999; Woodward M J et al., 2002; Nassar T J et al., 1994; Hassan J O et al., 1997; Gantois I et al., 2006).

Hence, although some *Salmonella* vaccines have been shown to be partially effective in reducing the rate of egg contamination, eggs from vaccinated hens cannot be guaranteed to be *Salmonella* free. Moreover, vaccine producers only claim a reduction in shedding of the bacteria in the faeces, not a protection against challenge infection or prevention of egg contamination.

The present invention provides a *Salmonella* vaccine that specifically counters the egg contamination and is not merely focused on the reduction of shedding. A further advantage of the present vaccine strain is that it is easy to administer and there is no risk of reversal to virulence, contrary to some commercial vaccine strains with undefined mutations.

SUMMARY OF THE INVENTION

It is an objective of the present invention to provide a *Salmonella* mutant strain, having at least one genetic modification within the tolC gene or within one or more of the resistance-nodulation-division (RND) genes of the efflux pump system. In particular, the *Salmonella* mutant strain comprises a genetic modification of the tolC gene or of one or all of the acrAB, acrEF and mdtABC genes. Preferably the genetic modification is an artificially introduced genetic modification, in particular resulting in an inactivation of the gene, and more in particular said modification is a deletion of at least a part of said gene(s), and more in particular of the complete gene(s).

With the objective to obtain *Salmonella* mutant strains, the tolC and RND gene modifications as defined herein, can be applied in wild type *Salmonella* serovars. The *Salmonella* mutant strain as defined and used herein, includes *Salmonella enterica* and any serotype of the *enterica* subspecies, and is typically selected from the group consisting of *Salmonella Enteritidis* (S. Enteritidis), S. Typhimurium, S. Hadar, S. Virchow, S. infantis, S. Kentucky, S. Bredeney, S. Agona, S. paratyphi B and S. Gallinarum. In a more particular embodiment said strain is *Salmonella* ser. *Typhimurium*, *Salmonella* ser. *Enteritidis*, *Salmonella* ser. *Infantis* or *Salmonella* ser. *Gallinarum*.

It is a further objective of the present invention to provide the use of a *Salmonella* mutant strain as described herein, in the manufacture of a vaccine and/or for preventing or reducing *Salmonella* infection in eggs.

In a further embodiment the present invention provides a composition, in particular a vaccine, comprising the *Salmonella* strain of the invention, and a pharmaceutically acceptable excipient, carrier and/or diluent, and optionally an adjuvant.

A further embodiment provides the *Salmonella* mutant strain, or the composition of the present invention for use as a medicament. More particular the invention provides the *Salmonella* mutant strain e.g. as part of a vaccine for use in the prevention or inhibition of *Salmonella* infection/colonization or a disease caused by such an infection in a subject and/or *salmonellosis* in humans, and in particular for prevention or (significant) reduction of *Salmonella* infection in eggs. Another embodiment provides the use of the mutant strain or composition of the present invention in the treatment or prevention of *Salmonella* infection, in particular for immunization of poultry, especially layer hens, against (disease or symptoms caused by) *Salmonella* infection.

It is also an object of the present invention to provide a method for treating, preventing, inhibiting and/or reducing the risk of (internal) *Salmonella* infection in eggs, as well as a method for immunising a subject against *Salmonella* disease, comprising administering a *Salmonella* mutant strain or a composition of the present invention, to a subject.

The invention further encompasses a method of producing *Salmonella* free eggs by immunising laying hens with the *Salmonella* mutant provided herein.

BRIEF DESCRIPTION OF THE DRAWINGS

FIG. 6: TolC, acrA, acrB, acrD, acrF, acrE, mdsB, mdsA, mdtA, mdtB, and mdtC coding sequences.

FIG. 7: Lohman Brown laying hen body weight after oral inoculation with $10^6$ CFU of a *Salmonella Gallinarum* 9R (SG9R) strain or $10^6$ CFU of a *Salmonella Gallinarum* tolC (SG tolC) deletion mutant strain on day 35 of life. Groups treated with either of the strains consisted of 20 animals, and the error bars shown in the figure represent the standard deviation of the mean.

Figure 1:
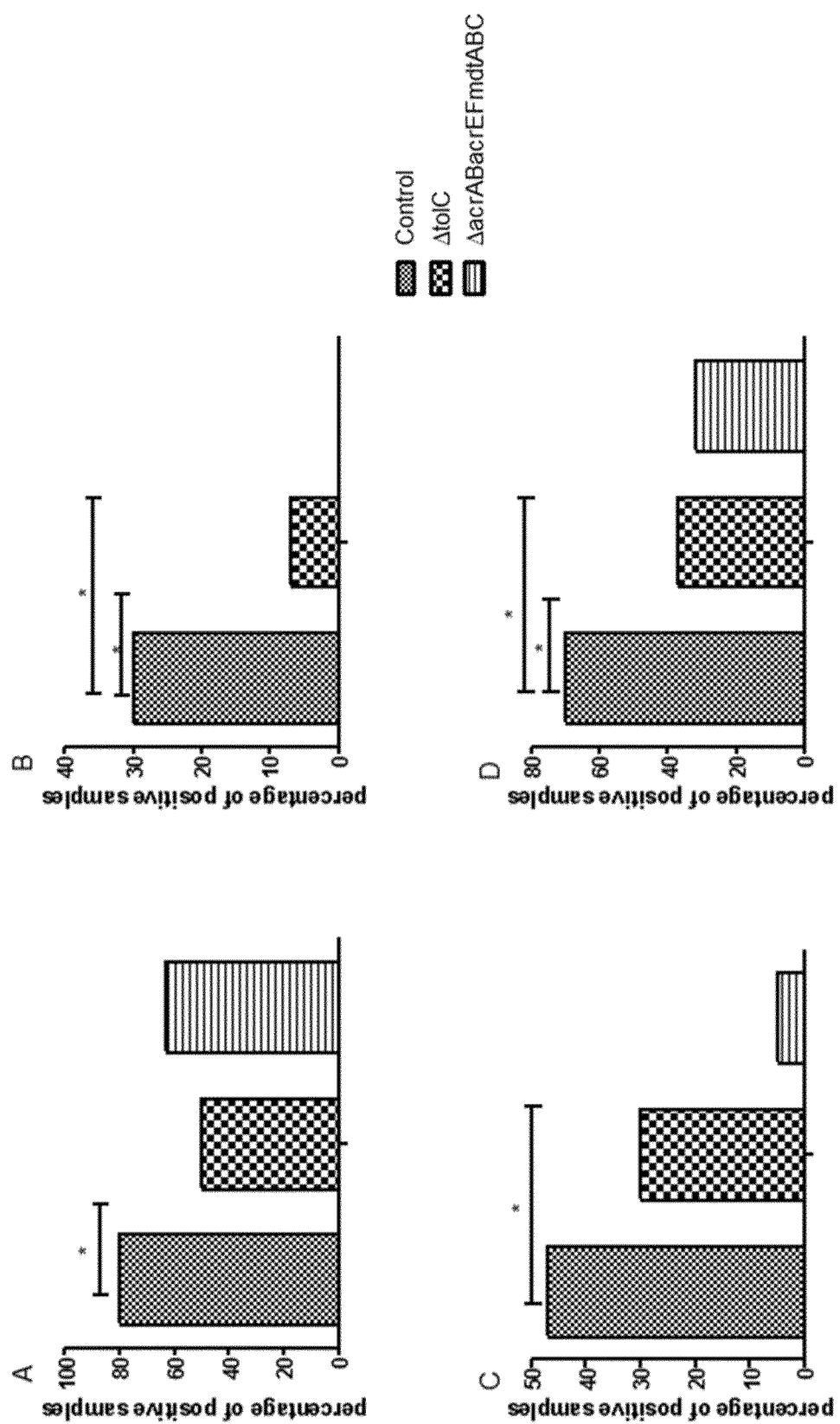
FIG. 1: The percentage of *Salmonella* positive samples in spleen (A), caeca (B), oviduct (C) and ovary (D) in non-vaccinated animals and animals vaccinated at day 1, week 6 and week 16 with *Salmonella Enteritidis* 147 $\Delta$tolC or *Salmonella Enteritidis* 147 $\Delta$acrABacrEFmdtABC strains, challenged at 3 weeks post-infection with *Salmonella Enteritidis* S1400/94, after enrichment. Statistical significant differences (p<0.05) in percentage of positive organ samples between vaccinated groups and the non-vaccinated control group are marked with an asterix.

Mutants with inactivated genes or deletion mutants (of the complete gene or (substantial) part thereof) are preferred. The genetic modifications or mutations may be introduced into the microorganism using any known technique. Preferably, the mutation is a deletion mutation, where disruption of the gene is caused by the excision of nucleic acids. Alternatively, mutations may be introduced by the insertion of nucleic acids or by point mutations. Methods for introducing the mutations into the specific regions will be apparent to the skilled person and are preferably created using the one step inactivation method described by Wanner and Datsenko (2000). Other methods can be applied to achieve a site directed mutagenesis (e.g. using suicide plasmids), however the one-step inactivation method is generally accepted as the best and fastest way to achieve a knock-out deletion mutant.

Preferably, the mutants of the present invention contain a deletion of (at least part of) the tolC gene or one or more of the RND genes of the efflux pump system, including the acrA, acrB, acrD, acrF, acrE, mdsB, mdsA, mdtA, mdtB, or mdtC gene. As used herein, the tolC, acrA, acrB, acrD, acrF, acrE, mdsB, mdsA, mdtA, mdtB, and mdtC gene is meant to include any homolog or artificial sequence that is substantially identical, i.e. at least 85%, 90%, 91%, 92%, 93%, 94%, 95%, 96%, 97%, 98%, 99%, and preferably 100% identical to the corresponding tolC, acrA, acrB, acrD, acrF, acrE, mdsB, mdsA, mdtA, mdtB, and mdtC gene as found in *Salmonella enterica* subsp. *enterica* serovar *Typhimurium* str. LT2 (NCBI: NC_003197.1 GI:16763390). In said reference sequence the tolC gene is characterized by Gene ID: 1254709 and encodes the TolC outer membrane channel protein. The acrA gene is characterized by Gene ID: 1251996 and encodes the AcrA acridine efflux pump. The acrB gene is characterized by Gene ID: 1251995 and encodes the AcrB RND family acridine efflux pump. The acrD gene is characterized by Gene ID: 1254003 and encodes the AcrD RND family aminoglycoside/multidrug efflux pump. The acrF gene is characterized by Gene ID: 1254914 and encodes the AcrF multidrug efflux protein. The acrE gene is characterized by Gene ID: 1254913 and encodes the AcrE multidrug efflux protein. The mdtA gene is characterized by Gene ID: 1253647 and encodes the MdtA multidrug resistance protein. The mdtB gene is characterized by Gene ID: 1253648 and encodes the MdtB multidrug resistance protein. The mdtC gene is characterized by Gene ID: 1253649 and encodes the MdtC multidrug resistance protein. The mdsA gene is characterized by Gene ID: 1251871 and encodes the MdsA cation efflux system protein. The mdsB gene is characterized by Gene ID: 1251870 and encodes the MdsB cation efflux system protein. The nucleic acid sequences of the tolC, acrA, acrB, acrD, acrF, acrE, mdsB, mdsA, mdtA, mdtB, and mdtC genes are given in FIG. 6 (SEQ ID NO: 1-11).

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI BLAST, which may be used with default parameters.

In one embodiment, the present invention encompasses a *Salmonella* mutant strain comprising a deletion of the tolC gene, as compared to the corresponding wild type sequence as found in *Salmonella enterica* subsp. *enterica* serovar *Typhimurium* str. LT2 (NCBI: NC_003197.1 GI:16763390). In a further embodiment, the present invention encompasses a *Salmonella* mutant strain comprising a deletion of all of the acrAB, acrEF and mdtABC genes, as compared to the corresponding wild type sequence as found in *Salmonella enterica* subsp. *enterica* serovar *Typhimurium* str. LT2 (NCBI: NC_003197.1 GI:16763390).

Although any serotype of *S. enterica* may be used to produce the mutant strain, in preferred embodiments, the modifications are inserted into *Salmonella* serovars most common in poultry, including serovars belonging to serogroup B such as *S. Agona, S. Bredeney, S. Paratyphi* B, *S. Typhimurium*, and monophasic strains of S. *Typhimurium*; serogroup D such as *S. Enteritidis* and *S. Gallinarum*; and serogroup C such as *S. Hadar, S. Virchow, S. Infantis*, and S. Kentucky. The combination of one or more of the mutant strains in one composition or vaccine is also envisaged by the present invention (e.g. mono-, bi-, tri or tetravaccine).

In a particular embodiment said modification(s) are inserted in a *Salmonella* spp. selected from the group comprising *Salmonella Salmonella enterica* subsp. *enterica* serovar *Enteritidis, Salmonella enterica* subsp. *enterica* serovar *Typhimurium* or *Salmonella enterica* subsp. *enterica* serovar *Infantis. Salmonella enterica* subsp. *enterica* serovar *Enteritidis* is a serovar of the D1 serogroup. S. *Enteritidis* is the most common serovar in the United States and Europe. *Salmonella enterica* subsp. *enterica* serovar *Typhimurium* is a serovar of the B serogroup. S. *Typhimurium* is a widely distributed serovar, which represent the second most common serovar isolated from humans in the United States and Europe. *Salmonella enterica* subsp. *enterica* serovar *Infantis* is a serovar of the Cl serogroup. S. *Infantis* is commonly found in chickens and broiler flocks.

A "subject" as used herein includes a human or an animal, in particular birds, more in particular poultry, and even more in particular chickens, especially laying hens (layers), breeders and/or broilers.

"Laying hen" or "egg-laying hen" is a common term for a female chicken that is kept primarily for laying eggs and includes young chickens that are reared for egg production. Some chickens are raised for meat (called "broiler" chickens), while others are primarily for eggs (used for human consumption). Raising laying hens is a different process than raising chickens for meat. Broiler chickens typically take less than six weeks to reach slaughter size while most laying hens are kept for one to three laying cycles (up to 200 weeks) before they are replaced with a new flock. Layers typically start laying eggs around 20 weeks of age. Layer feeds are formulated for chickens laying table eggs (those used for human consumption). Broiler feeds are formulated for those chickens producing hatching eggs ("breeders"). The diets are basically the same, but the breeder diets typically have slightly more protein and are fortified with extra vitamins for proper embryo development.

In a specific embodiment, the *Salmonella* mutant strains of the present invention are used as attenuated live vaccines. It is well established that live attenuated microorganisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed preparations, live vaccines are often more potent in inducing mucosal immune responses and cell-mediated responses, which may be connected with their ability to replicate in epithelial cells and antigen-presenting cells, such as macrophages, respectively. However, concerns remain over the safety of using live-attenuated vaccines. There may also be a risk of the attenuated strain reverting to virulence, thus having the potential to cause disease and abortion in the vaccinated animal. However, it was demonstrated that the mutant strains of the present invention are safe (no clinical symptoms and not persistently colonizing the host) and do not revert to virulence.

It is an object of the present invention to provide the use of the *Salmonella* mutant strains of the present invention for preparing a medicament which is employed for the prophylactic and/or therapeutic treatment of *Salmonella* infection in animals, in particular poultry, more particular chickens, and even more particular in layers. In a preferred embodiment the present invention provides the mutant strains of *Salmonella* as defined herein for use as a medicament. In particular, the present invention encompasses the (use of the) mutant strains of *Salmonella* as described herein for use in protecting against egg contamination. Hens' eggs produced by the immunized hens are substantially free from *Salmonella*. Remarkably, the present mutant strains have been shown to significantly reduce colonization of the reproductive organs. The oviduct can be subdivided into five functional regions. Starting from the ovary, there are the infundibulum, magnum, isthmus, uterus and vagina. The infundibulum captures the ovulatory follicles, the magnum produces the albumen, the isthmus deposits the eggshell membranes, the uterus forms the eggshell and the vagina is involved in oviposition. *Salmonella* colonizing the oviduct could be incorporated into the albumen, the eggshell membranes or the eggshell itself, depending on the site of colonization (magnum, isthmus and uterus, respectively). Although SE has been isolated from both the yolk and the albumen, according to several studies, the albumen is most frequently contaminated, pointing to the oviduct tissue as the colonization site. However, some studies found the yolk to be primarily contaminated, suggesting the ovary to be the primary colonization site (Gantois et al., 2009). It is thus an aim of the invention to provide *Salmonella* mutants strains for use in preventing or reducing colonization/infection of the oviduct tissues and/or the ovary.

In a further embodiment, the *Salmonella* mutant strains are used to manufacture a (pharmaceutical) composition, in particular a vaccine, which may be administered to the subject via the parenteral, mucosal or oral route. Live vaccines can be produced using art known procedures and typically include a (pharmaceutically) acceptable excipient, carrier or diluent, and optionally an adjuvant.

The present invention provides a pharmaceutical composition or a vaccine against *Salmonella* egg infection comprising:
 one or more of the mutant strains according to the invention; and
 a pharmaceutically acceptable carrier or diluent.

The particular pharmaceutically acceptable carriers or diluents employed are not critical to the present invention, and are conventional in the art. Examples of diluents include: buffer for buffering against gastric acid in the stomach, such as citrate buffer (pH 7.0) containing sucrose, bicarbonate buffer (pH 7.0) alone, or bicarbonate buffer (pH 7.0) containing ascorbic acid, lactose, and optionally aspartame. Examples of carriers include: proteins, e.g., as found in skimmed milk; sugars, e.g. sucrose; or polyvinylpyrrolidone.

The particular adjuvants employed are not critical to the present invention, and are conventional in the art. Examples of adjuvants include, but are not limited to, tensoactive compounds (such as Quil A), mineral salts (such as aluminium hydroxide), micro-organism derived adjuvants (such as muramyl dipeptide), oil-in-water and water-in-oil emulsions (such as Freund's incomplete adjuvant), particulate antigen delivery systems (such as liposomes, polymeric atmospheres, nanobeads, ISCOMs and ISCOMATRIX), polysaccharides (such as micro-particulate inulin), nucleic acid based adjuvants (such as CpG motivs), cytokines (such as interleukins and interferons), activators of Toll-like receptors and eurocine L3 en N3 adjuvantia.

As is known to the skilled person, the dose or amount varies according to the route of administration. Those skilled in the art may find that the effective (immunizing) dose for a vaccine administered parenterally may be smaller than a similar vaccine which is administered via drinking water, and the like. The number of microorganisms that are required to be present in the formulations can be determined and optimised by the skilled person. However, in general, a subject may be administered approximately $10^4$-$10^{10}$ colony-forming units (CFUs), preferably between $10^5$-$10^9$ CFUs in a single dosage unit, and more preferably between $10^7$-$10^9$ CFUs in a single dosage unit.

As already mentioned hereinbefore, the mutant strains and vaccine compositions of the present invention may be prepared by known techniques.

The choice of particular *Salmonella enterica* microorganism, can be made by the skilled person without undue experimentation. A preferred microorganism is selected from the group consisting of *Salmonella Enteritidis* (S. Enteritidis), *S. Typhimurium*, *S. Hadar*, *S. Virchow*, *S. Infantis*, *S. Kentucky*, *S. Bredeney*, *S. Agona*, *S. paratyphi* B and *S. Gallinarum*. In one embodiment the microorganism is *Salmonella Typhimurium*; more in particular the *Salmonella Typhimurium* strain 112910a (Van Parys et al., 2012; De Cort et al., 2014). In a further embodiment the microorganism is *Salmonella Enteritidis*; more particular the *Salmonella Enteritidis* strain 147 (Methner et al., 1995; Bohez et al., 2008; De Cort et al., 2013). In an even further embodiment, the microorganism is either *Salmonella Infantis* or *Salmonella Gallinarum*. In a particular embodiment of the present invention, the mutant strains are either tolC deletion mutants, or acrABacrEFmdtABC deletion mutants of *Salmonella Typhimurium* strain 112910a, or of *Salmonella Enteritidis* strain 147.

The *Salmonella* mutant strains as described herein are especially useful as vaccines, in particular (for use in a method in order) to prevent or (significantly) reduce *Salmonella* infection and/or colonization of the host tissue and/or whereby said mutant strain is capable of preventing or reducing (internal) egg contamination. A further embodiment provides the composition or vaccine of the present invention for use in the immunization of chickens, especially layers and broilers, against *Salmonella* infection. It is also an object of the present invention to provide a method for treating, reducing or preventing a *Salmonella* infection, comprising administering a *Salmonella* mutant strain as provided herein or a composition or vaccine of the present invention, to a subject in need thereof.

Furthermore, the invention is directed to reduce or prevent *salmonellosis* (e.g. gastroenteritis, vomiting, fever) in humans by the use of the *Salmonella* mutant strain and the methods as provided herein. In other words, the invention relates to the use of the *Salmonella* mutants strain for preventing or reducing egg contamination, e.g. by immunising or vaccinating hens in order to reduce colonization of the reproductive tissue. By such method, the contamination of the eggs is limited or absent and hence also the risk of *salmonellosis* and/or the number of food borne *Salmonella* infections in humans. Hence the method of the invention is especially useful to produce *Salmonella* free eggs.

In a particular embodiment, the *Salmonella Gallinarum* mutant strain is characterized in that it contains at least one genetic modification within the tolC gene or within one or more of the resistance-nodulation-division (RND) genes, i.e. acrAB, acrD, acrEF, mdtABC and mdsAB, and especially the acrAB, acrEF and mdtABC genes. Said S. *Gallinarum* mutant strain is especially useful in protecting layers or broilers against fowl typhoid, a severe septicaemic disease, in particular against clinical disease and internal organ colonization by S. *Gallinarum*. Clinical symptoms include anorexia, diarrhea, anemia, a decreased laying percentage but the major issue is the high mortality it can induce in both chicks and adult hens It is recognized that administration of an effective (immunizing) dose may be achieved by way of a single administration (i.e. administration of a single dose of a vaccine, said dose constituting an effective dose), or by way of multiple administration (i.e. administration of two or more doses of a vaccine, said two or more doses combining to constitute an effective dose). The use of multiple administrations of vaccines (for example a primary dose followed by one, two or more booster doses) is well known, particularly in the context of live vaccines, and is hence an embodiment of the present invention.

Oral administration of the strains or compositions of the invention may be achieved by inoculation (such as by oral gavage) or by application in drinking water. In one embodiment, the invention relates to (poultry) food comprising the *Salmonella* mutant(s) as described herein. As an alternative to their oral administration, suitably formulated strains or compositions may be administered to a subject by means of injection. In particular, strains or compositions in accordance with the present invention may be administered by intramuscular injection, intradermal injection subcutaneous injection, or intravenous injection. Formulations for use in the preparation of injectable vaccines are well known to those of skill in the art.

Strains or compositions in accordance with the present invention may also be administered by inhalation, for example via intranasal spray. It is well known to provide vaccines by nasal inhalation and such administration may be preferred since it lacks many of the undesirable effects associated with vaccination by injection (such as injection pain and the requirement for sterilizing equipment). Suitable nasal spray formulations which may be used in the preparation of vaccines in accordance with the present invention will be known to those skilled in the art.

It has also been shown that effective immunizing dosages of vaccines may be administered to poultry through the use of whole body sprays. Aerosol immunization in this manner has been found to be suitable for the generation of a systemic immune response, not just a response associated with the respiratory tract.

The mutant strains as provided herein can be part of a vaccination kit comprising a dispensing device and an (immunologically) effective amount of the vaccine strain. The dispensing device is preferably adapted for spray, aerosol delivery or ocular eye drops.

The invention will be described in further details in the following examples and embodiments by reference to the enclosed drawings. Particular embodiments and examples are not in any way intended to limit the scope of the invention as claimed. The rationale of the examples given here for the serotype S. Enteritids are equally well applicable to other *Salmonella enterica* serotypes infecting poultry, such as for example S. *Typhimurium*, S. *Hadar*, S. *Virchow*, S. *Infantis*, S. *Kentucky*, S. *Bredeney*, S. *Agona*, S. *Paratyphi* B and S. *Gallinarum*.

EXAMPLES

Example 1

Prevention of Egg Contamination by *Salmonella Enteritidis* after Oral Vaccination of Laying Hens with *Salmonella Enteritidis* ΔtolC and ΔacrABacrEFmdtABC Mutants Materials and Methods
Vaccine and Challenge Strains The vaccine strains ΔtolC and ΔacrABacrEFmdtABC are defined mutants of *Salmonella Enteritidis* 147 phage type 4. The wild type strain 147 was originally isolated from egg white and is resistant to streptomycin. The strain is known to colonize the gut and internal organs to a high level (Methner, al-Shabibi et al. 1995, Bohez, Dewulf et al. 2008). All mutations were constructed according to the one step inactivation method previously described by Datsenko and Wanner (Datsenko and Wanner, 2000).

The challenge and vaccine strains were incubated overnight with gentle agitation at 37° C. in Luria Bertani (LB) medium (Sigma, ST. Louis, Mo., USA). To determine bacterial titers, ten-fold dilutions were plated on brilliant green agar (BGA, Oxford, Basingstoke, Hampshire, UK) for the challenge strain. The vaccine strains were plated on LB supplemented with 1% lactose, 1% phenol red and 100 μg/ml streptomycin to determine the titer. The vaccine and challenge strains were diluted in HBSS (Hanks Balanced Salt Solution, Invitrogen, Paisley, England) to $10^8$ cfu/ml.

Experimental Birds

Ninety (90) day-old Lohmann Brown laying hens (De Biest, Kruishoutem, Belgium) were randomly divided into 3 groups and housed in separate units. The lighting program provided by the commercial supplier was implemented. Commercial feed and drinking water was provided ad libitum. The animal experiment in this study followed the institutional guidelines for the care and use of laboratory animals and was approved by the Ethical Committee of the Faculty of Veterinary Medicine, Ghent University, Belgium (EC2013/135). Euthanasia was performed with an overdose of sodium pentobarbital in the wing vein.

Experimental Setup

Two different groups (n=30) were orally immunized at day of birth, at 6 weeks of age and at 16 weeks of age through crop instillation of 0.5 ml containing $10^8$ cfu of *Salmonella Enteritidis* 147 ΔtolC (group 1) or *Salmonella Enteritidis* 147 ΔacrABacrEFmdtABC (group 2). A third group of birds (n=30) was kept as non-immunized but *Salmonella* challenged positive controls (group 4). At the age of 18 weeks, serum samples were taken for quantification of anti-*Salmonella Enteritidis* and anti-*Salmonella Typhimurium* antibodies in an LPS-ELISA (Desmidt, Ducatelle et al. 1996). At the same time, cloacal swabs were taken in each group and bacteriologically analyzed for the presence of the vaccine strains. At 21 weeks of age, all the hens were in lay and eggs were collected daily during 3 weeks for bacteriological detection of the vaccine strain in the egg content. At 24 weeks of age, all the animals were intravenously inoculated in the wing vein with 0.5 ml containing $5 \times 10^7$ cfu of the *Salmonella Enteritidis* strain S1400/94. This protocol was already used to produce high levels of internal egg contamination (De Buck, Van Immerseel et al. 2004, Gantois, Ducatelle et al. 2006). The eggs were collected daily during 3 weeks and analyzed for the presence of the challenge strain. Three weeks after challenge inoculation, all the animals were euthanized by an overdose of pentobarbital in the wing vein. Samples of the spleen, oviduct, ovary, uterus and caecum were aseptically removed for bacteriological quantification of challenge and vaccine strain bacteria.

ELISA to Quantify Anti-LPS Antibodies

Serum samples taken at week 18 were analyzed for the levels of anti-*Salmonella* LPS antibodies using a previously described indirect ELISA protocol (Desmidt et al., 1996). Four 96 well-plates (Sigma, St. Louis, Mo., USA) were coated with 100 µl of an LPS solution (10 µg/ml) in 0.05M carbonate-bicarbonate (pH 9.6; coating buffer) and incubated for 24 hours at 4° C. The LPS was purified from *Salmonella Enteritidis* PT4, strain 76Sa88 and *Salmonella Typhimurium*, strain 742Sa91. The plates were rinsed four times with phosphate buffered saline (PBS, Sigma, St. Louis, Mo., USA) supplemented with 0.1% Tween-20 (Sigma, St. Louis, Mo., USA; washing buffer) between each step. In the first step, 100 µl PBS (Sigma, St. Louis, Mo., USA) supplemented with 1% bovine serum albumin (BSA, Sigma, St. Louis, Mo., USA; blocking buffer) was added to the wells for one hour at 37° C. The blocking buffer was then removed. Secondly, serum samples of animals from the different groups were diluted in blocking buffer (1:200) and added to the plates (100 µl). As a negative control, serum from a *Salmonella* free chicken was used. Serum from a chicken that had been infected experimentally with *Salmonella Enteritidis* PT4, strain 76Sa88, was used as a positive control. The plates were allowed to shake for 2 hours at 37° C. Thirdly, peroxidase-labelled rabbit anti-chicken IgG (100 µl, Sigma, St. Louis, Mo., USA) was diluted (1:2000) in blocking buffer and added to the wells for 1 hour and 30 min while shaking at 37° C. Finally 50 µl of TMB substrate (Fisher Scientific, Erembodegem, Belgium) was added to the wells. When a blue color started to appear the reaction was blocked with 50 µl of sulfuric acid (0.5M). The absorbance was measured by the ELISA reader at 450 nm. Every sample was analyzed in duplicate The cut-off OD value was calculated as the mean obtained from the sera from the *Salmonella* free chicks (the non-vaccinated birds) plus five times the standard deviation (OD=0.55).

Bacteriological Examination of the Challenged Birds

The cloacal swabs taken at week 18 were incubated overnight at 37° C. in buffered peptone water (BPW, Oxoid, Basingstoke, Hampshire, UK). Afterwards a loopful was plated on LB plates supplemented with 1% lactose, 1% phenol red and either 100 µg/ml streptomycin (Sigma, St. Lous, Mo., USA) for the detection of the *Salmonella Enteritidis* 147 Δtol C and ΔacrABacrEFmdtABC vaccine strains. Samples of caecum, spleen, ovary, oviduct and uterus were homogenized in BPW (10% weight/volume suspensions) and 10-fold dilutions were made in HBSS (Invitrogen, Paisley, England). Six droplets of 20 µl of each dilution were plated on BGA (for quantification of the challenge strain) or on LB supplemented with 1% lactose, 1% phenol red and the appropriate antibiotics (for quantification of the vaccines). After overnight incubation at 37° C., the number of cfu/g tissue was determined by counting the number of bacterial colonies for the appropriate dilution. Samples that tested negative after direct plating for the challenge strain were pre-enriched in tetrathionate brilliant green broth (Oxoid, Basingstoke, UK) by overnight incubation at 37° C. After incubation, a loopful of the tetrathionate brilliant green broth was plated on BGA.

Egg Production and Bacteriological Examination of Eggs

Eggs were collected daily for 6 weeks from week 18 onwards and the egg production was determined. Each day, eggs of six chicks per group were pooled in one batch, yielding an egg per batch number that varied between one and six. Upon collection, lugol solution and 95% ethanol were subsequently used to decontaminate the surface of the eggshell. After decontamination of the eggshell, the eggs were broken aseptically and the total content of the eggs was pooled and homogenized per batch. A volume of 40 ml of BPW was added for each egg to the pooled egg content and incubated for 48 h at 37° C. To detect the vaccine strains, a loopful of the BPW broth was plated on LB plates supplemented with 1% lactose, 1% phenol red and 100 µg/ml streptomycin. To detect the challenge strain, a loopful of the BPW broth was plated on BGA. Additionally, further enrichment was done overnight at 37° C. in tetrathionate brilliant green broth and after incubation, a loopful of broth culture was streaked onto BGA.

Statistical Analysis

GraphPad Prism 5 software was used for statistical analysis. Data of cfu *Salmonella*/gram tissue of the caecum, spleen, ovary, oviduct and uterus were log-transformed and analyzed by an anova test followed by a Dunnet post hoc test to determine differences between the groups. After enrichment samples were classified as either positive or negative. A Fisher's exact test was used to determine significant differences. Cloacal swabs and batches of eggs were categorized as either positive or negative. As such a Fisher's exact test was also done to determine significant differences. For all tests, differences with p-values below 0.05 were considered to be statistically significant.

Results

Detection of Anti-*Salmonella* LPS Antibodies in Serum

Figure 2:
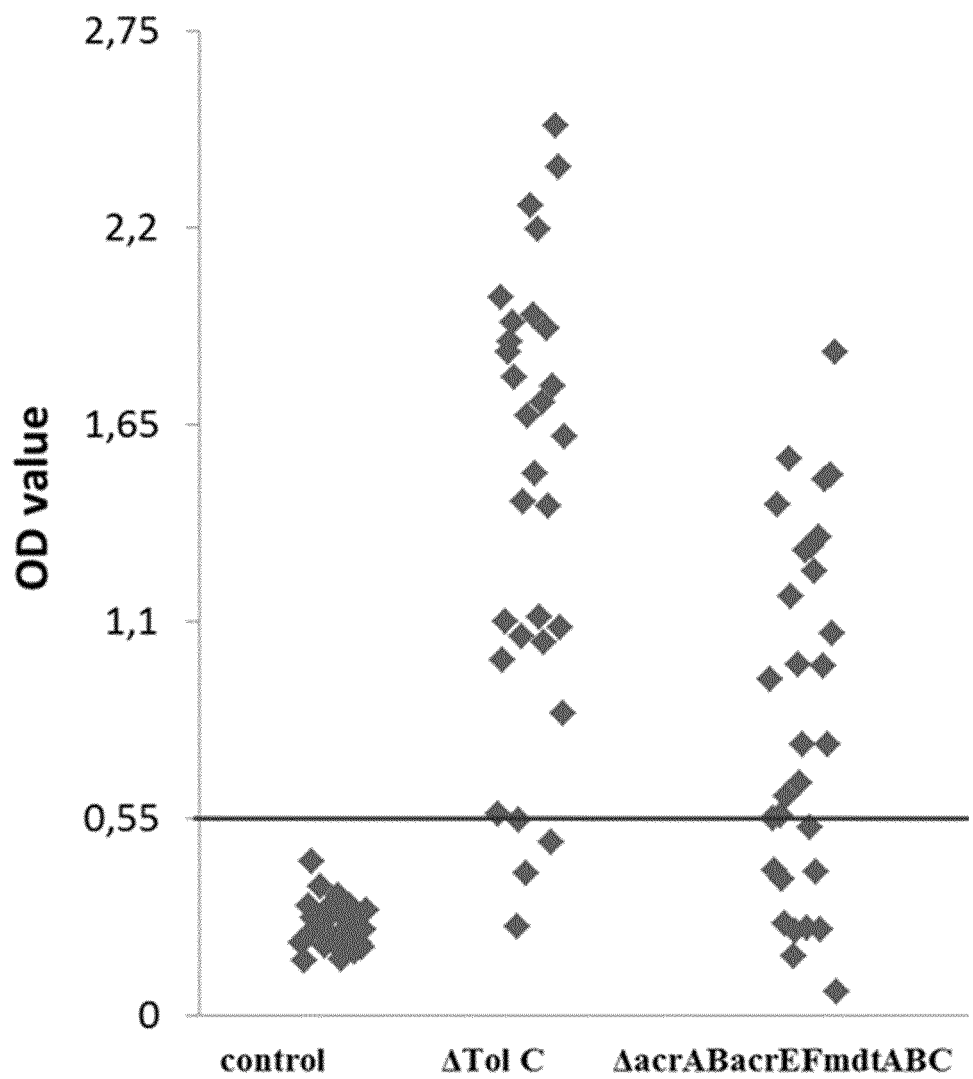
FIG. 2: OD values of the ELISA detecting anti-*Salmonella* LPS antibodies in the sera of 18 week old laying hens, vaccinated at day 1, week 4 and week 16 with *Salmonella Enteritidis* 147 $\Delta$tolC or *Salmonella Enteritidis* 147 $\Delta$acrABacrEFmdtABC. The cut-off OD value is 0.55 and is calculated as the mean obtained from the sera from the *Salmonella* free chicks (control group) plus five times the standard deviation.

Data derived from the LPS-ELISA show that 26/30 and 19/30 chicks contained anti-*Salmonella* LPS antibodies in the group of animals vaccinated with the *Salmonella Enteritidis* 147 ΔtolC and *Salmonella Enteritidis* 147 ΔacrABacrEFmdtABC strain, respectively (FIG. 2).

Analysis of Cloacal Swabs and Eggs for the Presence of Vaccine Strains

No cloacal swabs were found positive in the groups vaccinated with the *Salmonella Enteritidis* 147 ΔtolC and *Salmonella Enteritidis* 147 ΔacrABacrEFmdtABC strains. No swabs were positive in the non-vaccinated control group. None of the vaccine strain was isolated from the egg content samples.

Clinical Signs and Egg Production after Challenge

Over the whole experiment, there was no reduction in feed and water intake in either of the groups. The egg production rate after infection in the unvaccinated control group dropped to 59% in the first week post-infection (pi) and raised to 75% and 86% in the second and third week pi. The egg production rate also decreased in the vaccinated groups. No significant differences were detected. The egg production percentages in the group vaccinated with the ΔtolC strain was 60%, 100% and 90%, and 56%, 70%, 68% for the ΔacrABacrEFmdtABC strain in the first, second and third week pi respectively. Some eggs were thin-shelled and malformed during the first week of infection. At the end of the experiment 11 chicks died in the group of animals vaccinated with the *Salmonella Enteritidis* 147 ΔacrABacrEFmdtABC strain because of cannibalism.

Isolation of the Challenge Strain from Egg Contents

The non-vaccinated hens laid significantly more *Salmonella* positive eggs compared to the vaccinated animals during the whole 3-week follow-up period. Three egg batches were *Salmonella* positive in the control group while the batches from the vaccine strains were negative after direct plating. Not a single positive egg batch was detected for animals vaccinated with the *Salmonella Enteritidis* 147 ΔtolC and *Salmonella Enteritidis* 147 ΔacrABacrEFmdtABC strains. No positive egg batches were found in the third week pi.

TABLE 1

The percentage of egg content batches positive for the challenge strain *Salmonella Enteritidis* S1400/94 in non-vaccinated animals and animals vaccinated at day 1, week 6 and week 16 with *Salmonella Enteritidis* 147 ΔtolC or *Salmonella Enteritidis* 147 ΔacrABacrEFmdtABC strains, during the two weeks following infection. Results are shown after incubation of the egg content in BPW (48 h, 37° C.). Results between brackets show the percentage of batches positive after enrichment in tetrathionate brilliant green broth (37° C., overnight). Different superscripts indicate significant differences between the groups ($p < 0.05$).

| Group | Week 1 | Week 2 |
|---|---|---|
| Non-vaccinated | $70^a(74^a)$ | $0(17)^a$ |
| ΔtolC | $0^c(0)^c$ | $0(0)^c$ |
| ΔacrABacrEFmdtABC | $0^c(0)^c$ | $0(0)^c$ |

Isolation of the Challenge Strain from the Organs at 3 Weeks Post-Infection

No samples were positive at direct plating. No significant differences in *Salmonella* colonization were seen for the uterus (data not shown). FIG. 1 presents the percentage of *Salmonella* positive samples in the spleen, caeca, oviduct and ovary in non-vaccinated animals and animals vaccinated at day 1, week 6 and week 16 with either the *Salmonella Enteritidis* 147 ΔtolC or the *Salmonella Enteritidis* 147 ΔacrABacrEFmdtABC strains, at 3 weeks pi with *Salmonella Enteritidis* S1400/94 after enrichment. Vaccination with the *Salmonella Enteritidis* 147 ΔtolC and ΔacrABacrEFmdtABC strain both significantly decreased the number of *Salmonella* positive samples in the spleen, caeca, oviduct and ovary against the control group. Additionally in the ΔacrABacrEFmdtABC vaccinated group, the number of *Salmonella* positive samples in the oviduct was significantly lower than the group vaccinated with ΔtolC.

Example 2

A *Salmonella Enteritidis* and *Salmonella Typhimurium* tolC and acrABacrEFmdtABC Deletion Mutant are Safe for Use as Live Vaccine Strains in Broilers Material & Methods
Chickens One-day-old Ross broiler chickens were obtained from a local hatchery and housed in isolation. Experimental groups were housed in separate rooms in containers on wood shavings. Commercial feed and drinking water were provided ad libitum. Experiments were performed with the permission of the Ethical Committee of the Faculty of Veterinary Medicine, Ghent University, Belgium.

Vaccine Strains

*Salmonella Enteritidis* 147 Strep$^R$ (SE147) is a well-characterized strain originally isolated from egg white and was used for the production of the deletion mutants (Methner et al. 1995; Methner et al. 1995; Bohez et al. 2008). A spontaneous nalidixic acid-resistant mutant of *Salmonella Typhimurium* strain 112910a, originally isolated from a pig stool sample (Van Parys et al. 2012), was used for the production of the other deletion mutants. This antibiotic resistance has previously been shown to have no impact on the in vivo results (Barrow et al. 1987). Deletion of the tolC gene or the acrAB, acREF and mdtABC genes was done using the one-step inactivation method described by Datsenko and Wanner (Datsenko and Wanner 2000; Bohez et al. 2006). This yielded a *Salmonella Enteritidis* StrepR tolC deletion mutant, a *Salmonella Enteritidis* 147 Strep$^R$ acrAbacrEFmdtABC deletion mutant, a *Salmonella Typhimurium* Nal$^R$ tolC deletion mutant and a *Salmonella Typhimurium* Nal$^R$ acrAbacrEFmdtABC deletion mutant.

Experimental Design

Analysis of the Colonisation Pattern of *Salmonella Enteritidis* and *Salmonella Typhimurium* ΔtolC or ΔacrABacrEFmdtABC Mutant Strains in Broilers: Evaluation of Safety.

One hundred and twenty one-day-old chicks were divided into 2 groups of 60 and each housed in a container of 2.4 m². One group was given 0.5 ml of a mixture containing $2 \times 10^8$ CFU/ml of the *Salmonella Enteritidis* ΔtolC strain and $2 \times 10^8$ CFU/ml of the *Salmonella Typhimurium* ΔtolC strain by oral gavage. The other group was given 0.5 ml of a mixture containing $2 \times 10^8$ CFU/ml of the *Salmonella Enteritidis* ΔacrAbacrEFmdtABC strain and $2 \times 10^8$ CFU/ml of the *Salmonella Typhimurium* ΔacrAbacrEFmdtABC strain by oral gavage. To evaluate colonisation by the deletion mutant strains, their numbers in caecum and spleen were determined for 20 animals at days 7, 21 and 36. Shedding of the strains was evaluated during the experiment by bacteriological analysis of cloacal swabs taken on days 2, 9, 16, 23 and 30.

Bacteriological Analysis

Cloacal swabs were directly inoculated on Lysogeny Broth (LB) plates with 20 μg/ml nalidixic acid (Sigma-Aldrich, St. Louis, Mo., USA) or 100 μg/ml streptomycin (Sigma-Aldrich, St. Louis, Mo., USA). Samples negative after direct inoculation were pre-enriched in buffered peptone water (BPW, Oxoid, Basingstoke, England) and incubated overnight at 37° C. One ml of this suspension was further enriched by adding 9 ml tetrathionate-brilliant green broth (Merck, Darmstadt, Germany). After overnight incubation at 37° C., this suspension was plated on LB plates supplemented with the appropriate antibiotic. Samples of caecum and spleen were homogenized in BPW and 10-fold dilutions were made in HBSS. Six droplets of 20 μl of each dilution were plated on LB plates supplemented with 20 μg/ml nalidixic acid or 100 μg/ml streptomycin. After overnight incubation at 37° C., the number of CFU/g tissue was determined by counting the number of bacterial colonies on the plates. Negative samples were enriched as described above.

Results

Administration of the *Salmonella Enteritidis* and the *Salmonella Typhimurium* tolC deletion mutants and the *Salmonella Enteritidis* and the *Salmonella Typhimurium* acrABacrEFmdtABC deletion mutants to one day old broilers did not induce clinical symptoms in the animals. In the group treated with the *Salmonella Enteritidis* and the *Sal-* monella Typhimurium tolC deletion mutants 2 animals died, while in the group treated with the *Salmonella Enteritidis* and the *Salmonella Typhimurium* acrABacrEFmdtABC deletion mutants 5 animals died. This does not differ significantly from average mortality (5%) when rearing broilers. (GraphPad Prism 5 software was used for statistical analysis. A Fisher's exact test (one-sided) was used to analyse mortality rates within differently treated groups.)

Figure 3:
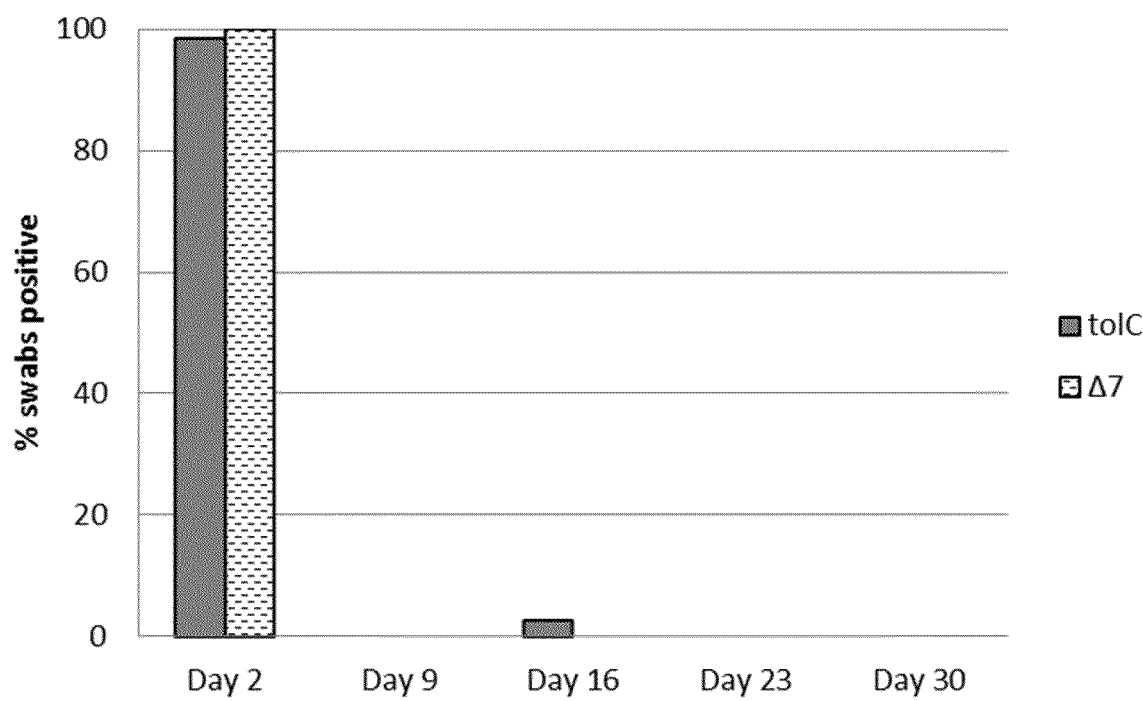
FIG. 3: Percentage of cloacal swabs positive for the *Salmonella Enteritidis* and *Salmonella Typhimurium* tolC or acrABacrEFmdtABC ($\Delta$7) deletion mutant strains after administration of these strains to one day old broilers. Broilers were inoculated with both *Salmonella Enteritidis* and *Salmonella Typhimurium* tolC deletion mutant strains or with *Salmonella Enteritidis* and *Salmonella Typhimurium* acrABacrEFmdtABC deletion mutant strains on the first day of life. Cloacal swabs were then weekly taken to monitor shedding of these strains.

As shown in FIG. 3, nearly all cloacal swabs taken one day after inoculation were positive. However, shedding declined quickly with only a limited number of animals shedding the tolC deletion strains on day 16, and no animals were shedding any of the deletion mutant strains from day 23 onwards.

Figure 4:
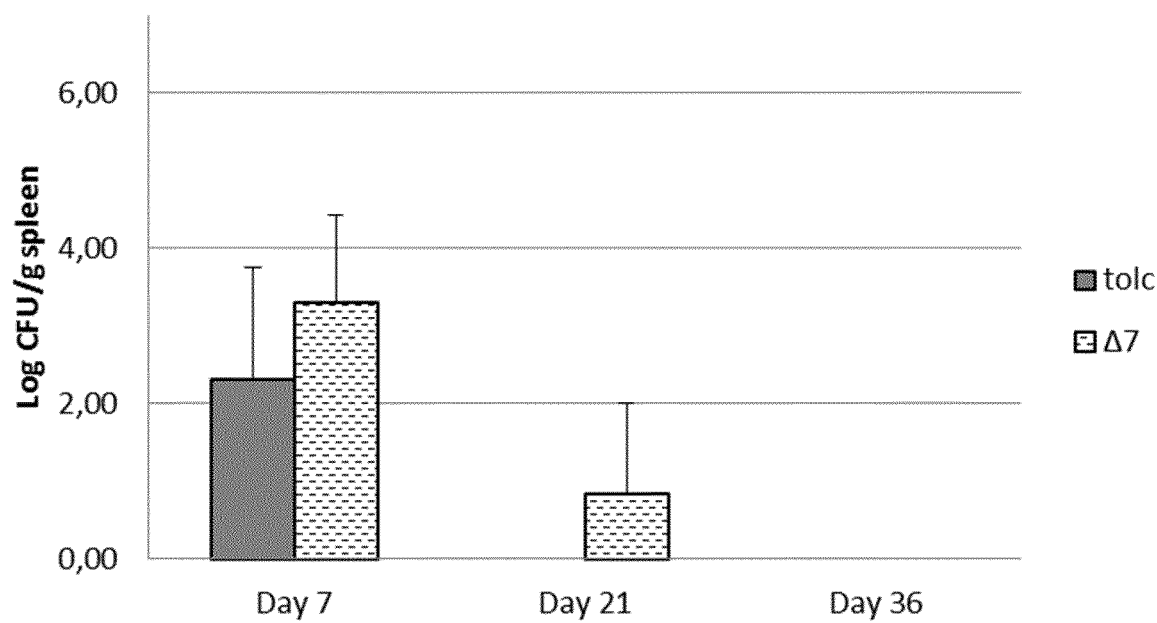
FIG. 4: Spleen colonization by *Salmonella Enteritidis* and *Salmonella Typhimurium* tolC or acrABacrEFmdtABC ($\Delta$7) deletion mutant strains after administration to one day old broilers. Broilers were inoculated with both *Salmonella Enteritidis* and *Salmonella Typhimurium* tolC deletion mutant strains or with *Salmonella Enteritidis* and *Salmonella Typhimurium* acrABacrEFmdtABC deletion mutant strains on the first day of life. Represented values are $\log_{10}$ CFU/g sample. Samples were taken on day 7, 21 and 36. The error bars represent the standard error of the means (SEM).

None of the strains could be detected in the caecum after direct plating on day 7, 21 or 35. In the spleen however, the tolC and the acrABacrEFmdtABC deletion mutant strains colonized the spleen on day 7, and the acrABacrEFmdtABC deletion mutant strains still colonized the spleen on day 21 (FIG. 4). However, by slaughter age (earliest at day 36), the *Salmonella Enteritidis* and *Salmonella Typhimurium* tolC and the *Salmonella Enteritidis* and *Salmonella Typhimurium* acrABacrEFmdtABC deletion mutant strains could no longer be found in the spleen or caecum.

Figure 5:
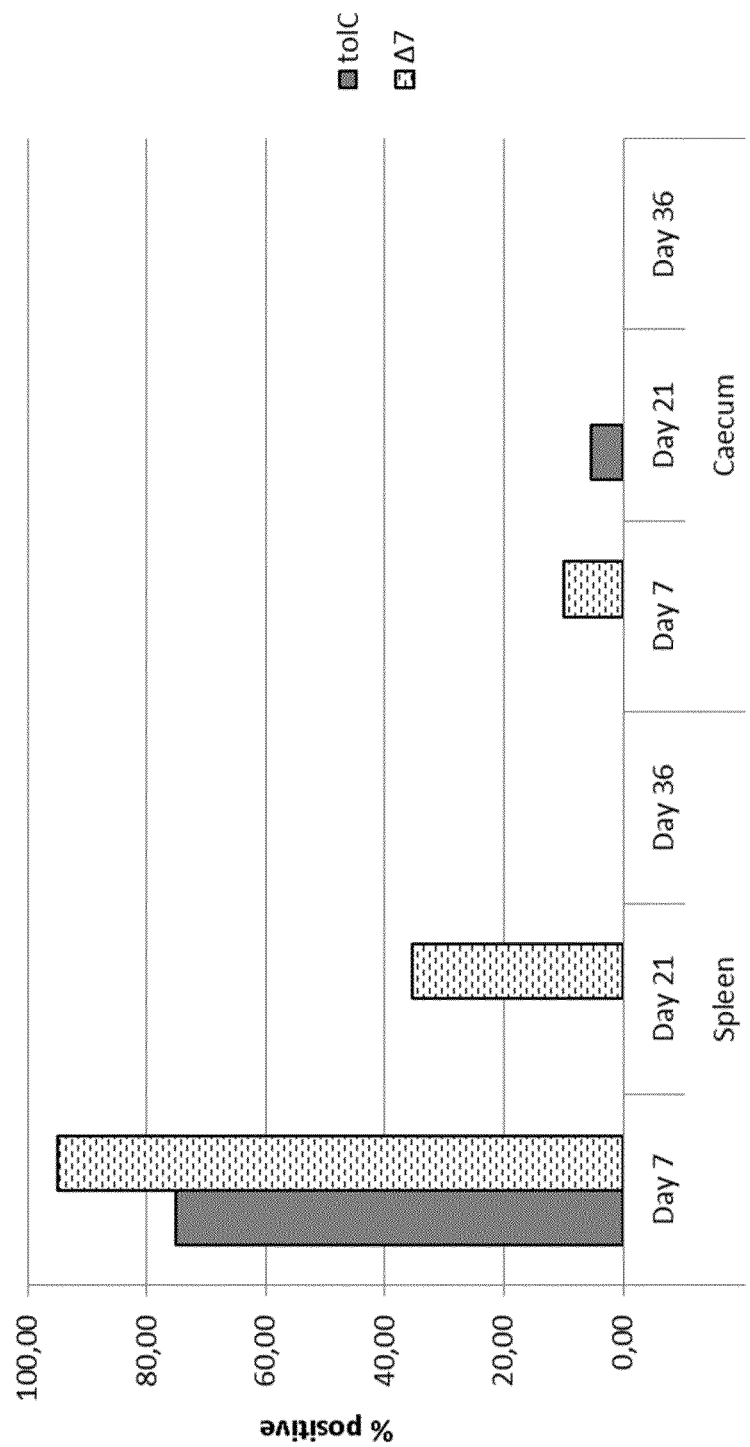
FIG. 5: Percentage of spleen and caecum samples positive for *Salmonella Enteritidis* and *Salmonella Typhimurium* tolC or acrABacrEFmdtABC ($\Delta$7) deletion mutant strains after enrichment. Broilers were inoculated with both *Salmonella Enteritidis* and *Salmonella Typhimurium* tolC deletion mutant strains or with *Salmonella Enteritidis* and *Salmonella Typhimurium* acrABacrEFmdtABC deletion mutant strains on the first day of life.

Enrichment of caecum and spleen samples confirmed these findings (FIG. 5), as both the tolC and acrABacrEFmdtABC deletion mutant strains could be found in the spleens of a high percentage of the animals on day 7, and the acrABacrEFmdtABC deletion mutant strains still colonized the spleen on day 21. However, by day 36, none of the strains could still be found in the spleens of any of the animals. In addition, the tolC and acrABacrEFmdtABC deletion mutant strains could only be found in a small number of the caeca after enrichment, and there were no caeca positive for any of the deletion mutant strains at slaughter age.

These results indicate that both the *Salmonella Enteritidis* and the *Salmonella Typhimurium* tolC deletion mutants and the *Salmonella Enteritidis* and the *Salmonella Typhimurium* acrABacrEFmdtABC deletion mutants are safe for use in broilers, and that they are cleared by slaughter age. As a consequence, these strains can thus be used as live vaccine strains in broilers.

Example 3

Evaluation of the Safety of a *Salmonella Gallinarum* tolC Deletion Mutant Strain for Use as a Vaccine Strain Offering Protection Against *Salmonella Gallinarum* Infections in Poultry Material & Methods Chickens One-day-old Lohmann Brown laying hens were obtained from a local hatchery and housed in isolation. Experimental groups were housed in separate rooms in containers of 2.4 $m^2$ on wood shavings. Commercial feed and drinking water were provided ad libitum. Experiments were performed with the permission of the Ethical Committee of the Faculty of Veterinary Medicine, Ghent University, Belgium.

Vaccine Strains

*Salmonella Gallinarum* strain 9 (SG9) was used for the production of the deletion mutants. This strain was originally isolated in the United Kingdom (Van Immerseel et al., 2013). Deletion of the tolC gene was done using the one-step inactivation method described by Datsenko and Wanner (Datsenko and Wanner, 2000; Bohez et al., 2006). This yielded a *Salmonella Gallinarum* tolC deletion mutant. In addition, *Salmonella Gallinarum* 9R (SG9R) was used in this study as well. This strain is frequently used in practice to control *Salmonella Gallinarum* infections in poultry (Van Immerseel et al., 2013), and was used as a control strain to compare the *Salmonella Gallinarum* tolC deletion mutant strain to.

Experimental Design

Forty one-day old laying hens were randomly divided into two groups of twenty chickens and housed in separate rooms. They were reared for 5 weeks, until the animals were 35 days old. On day 35 of life, all animals in the first group were orally inoculated with 1 ml of a mixture containing $10^6$ CFU/ml of a *Salmonella Gallinarum* to/C deletion mutant. The other group was orally inoculated with 1 ml of a mixture containing $10^6$ CFU/ml of the SG9R strain. The weight of the animals was monitored for four weeks, and when the animals were 63 days old (9 weeks) samples were taken from liver and spleen to evaluate colonisation by the *Salmonella Gallinarum* tolC deletion mutant strain and the SG9R strain through bacteriological analysis. Post-mortem examination of liver and spleen was performed as well, scoring enlargement and necrotic foci in liver and spleen as described by Matsuda et al. (Matsuda et al., 2011). In addition, the weight of livers and spleens was determined as well.

Bacteriological Analysis

Samples of liver and spleen were homogenized in buffered peptone water (BPW, Oxoid, Basingstoke, England) and 10-fold dilutions were made in Hank's Balanced Salt Solution (HBSS, Invitrogen, Paisley, England). Six droplets of 20 μl of each dilution were plated on Lysogeny Broth (LB) plates supplemented with 20 μg/ml nalidixic acid or 100 μg/ml streptomycin. After overnight incubation at 37° C., the number of CFU/g tissue was determined by counting the number of bacterial colonies on the plates. Negative samples were enriched by adding 9 ml tetrathionate-brilliant green broth (Merck, Darmstadt, Germany) to one ml of the samples homogenized in BPW. After overnight incubation at 37° C., this suspension was plated on LB plates supplemented with the appropriate antibiotic.

Statistical Analysis

GraphPad Prism software (Version 5.0, GraphPad Software Inc., La Jolla, Calif.) was used for statistical analysis of the obtained data. A Mann-Whitney test was used to analyse the difference in weight and the difference in enlargement scores and necrotic foci scores between the two groups.

Results

Administration of the *Salmonella Gallinarum* tolC deletion mutant or the *Salmonella Gallinarum* 9R strain to 5 week old laying hens did not induce clinical symptoms in the animals. No animals died during the experiment, indicating that both strains are severely attenuated when compared to wild-type *Salmonella Gallinarum* strains.

The average body weight of the laying hens before vaccination (on day 35) did not differ significantly between the groups (FIG. 7). After oral inoculation with either a SG9R strain or a *Salmonella Gallinarum* tolC deletion mutant, no statistical significant differences could be observed between both groups during the experiment, except on day 51 when there was a statistically significant difference between the two groups. However, this difference was most probably due to the animals being reared in separate rooms, as this was the only day a difference could be observed and the average weight of the animals in the group treated with the *Salmonella Gallinarum* ΔtolC strain tented to be lower throughout the entire experiment, even prior to treatment.

Figure 8:
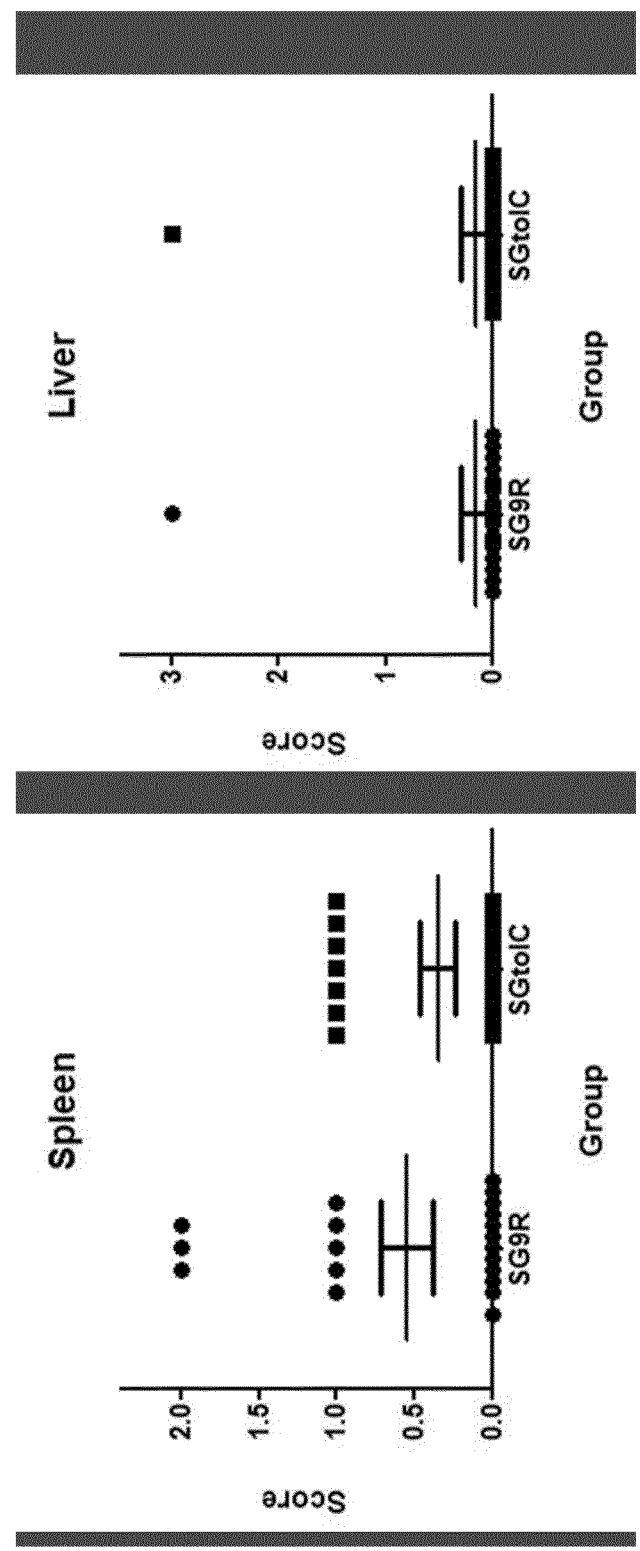
FIG. 8: Necrotic foci scores after post-mortem examination of spleen and liver of Lohmann Brown laying hens that were orally inoculated with a *Salmonella Gallinarum* 9R (SG9R) strain or a *Salmonella Gallinarum* ΔtolC (SGtolC) strain. Animals were treated on day 35 of life, liver and spleens were collected and examined on day 63 of life. Necrotic foci scores were determined as described by Matsuda et al. (2011). Necrotic foci scores for the spleen were determined according to the following macroscopic findings: score 0: no foci, score 1: fewer than 5 foci, score 2: fewer than 20 foci, score 3: greater than 20 foci. Scores for necrotic foci in the liver were determined according to macroscopic findings: score 0: no foci, score 1: fewer than three foci, score 2: f Such susceptibility may be analysed by minimum inhibitory concentration (MIC) testing of an antibiotic for test strains in the presence or absence of efflux pump inhibitor. Preferably a bacterium suitable for use in accordance with the invention may, for example, have at least 50% less efflux pump function than comparable wild type bacteria, preferably, at least 75% less efflux pump function, more preferably at least 90% less efflux pump function, and even more preferably 100% less efflux pump function.

When comparing the necrotic foci scores for the spleen between the differently treated groups, no statistically significant difference could be observed between both groups (FIG. 8). In both groups, only one liver had more than ten foci. For no other livers necrotic foci could be observed. As such, there was no statistically significant difference between the two groups for liver necrotic foci score (FIG. 8).

Figure 9:
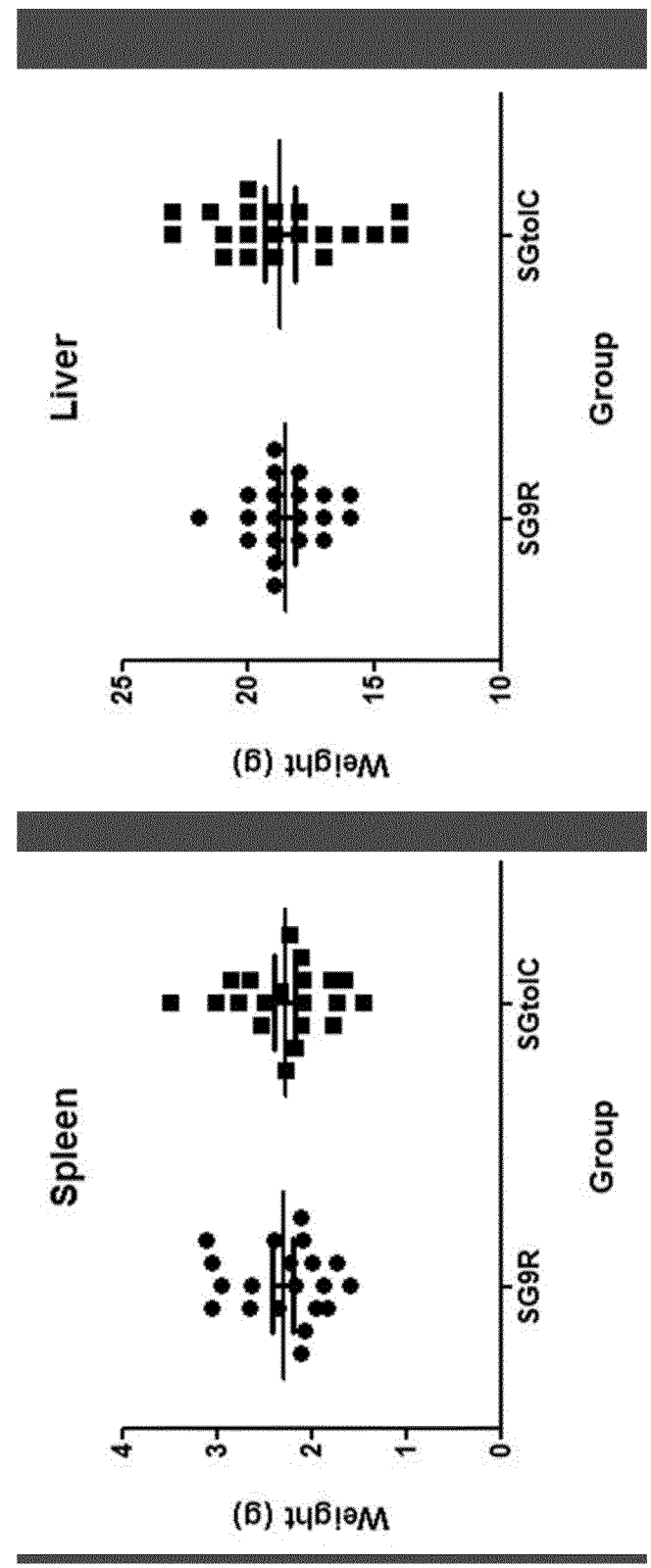

No statistically significant differences could be observed when comparing the average weight of livers and spleens of laying hens treated with a SG9R or a *Salmonella Gallinarum* ΔtolC strain (FIG. 9). In addition, no statistically significant differences could be observed when comparing the enlargement scores of liver and spleen. All spleens and livers in the group treated with the SG9R strain received a score equal to zero, while one spleen received a score equal to one, and one spleen a score of two in the *Salmonella Gallinarum* ΔtolC strain treated group. One liver in the group treated with the *Salmonella Gallinarum* ΔtolC strain received a score equal to two. However, when comparing the two groups, these differences were not statistically significant.

The SG9R and the *Salmonella Gallinarum* tolC deletion mutant strain could not be detected in liver or spleen after bacteriological analysis of the samples, even after enrichment, indicating that they are cleared from vaccinated laying hens within 4 weeks after administration if the strains are administered on day 35 of life.

These results indicate that the *Salmonella Gallinarum* tolC deletion mutant is an at least as safe vaccine strain as the commonly used SG9R strain, as there were no statistically significant differences in remaining virulence between both strains. As a consequence, the *Salmonella Gallinarum* ΔtolC strain can be used as a live vaccine strain in laying hens.

Example 4

Protection Offered by a Culture Consisting of *Salmonella Enteritidis and Salmonella Typhimurium* ΔacrABacrEFmdtABC Mutant Strains Against Experimental *Salmonella Enteritidis* and *Typhimurium* Infection in Broilers: Evaluation of Efficacy Material & Methods Chickens One-day-old Ross 308 broiler chickens were obtained from a local hatchery and housed in isolation. Experimental groups were housed in separate rooms in containers on wood shavings, while commercial feed and drinking water were provided ad libitum. The chickens were examined daily for clinical symptoms following inoculation with *Salmonella* strains. Experiments were performed with the permission of the Ethical Committee of the Faculty of Veterinary Medicine, Ghent University, Belgium.

*Salmonella* Strains

*Salmonella Enteritidis* 147 strepR (SE147) is a well-characterized strain originally isolated from egg white and was used for the production of the deletion mutants (Methner et al., 1995a; b; Bohez et al., 2008). A spontaneous nalidixic acid-resistant mutant of *Salmonella Typhimurium* strain 112910a, originally isolated from a pig stool sample (Van Parys et al., 2012), was used for the production of the *Salmonella Typhimurium* deletion mutants. This antibiotic resistance has previously been shown to have no impact on the in vivo results (Barrow et al., 1987). Deletion of the toIC gene or the acrAB, acREF and mdtABC genes was done using the one-step inactivation method described by Datsenko and Wanner (Datsenko and Wanner, 2000; Bohez et al., 2006). This yielded a *Salmonella Enteritidis* strepR tolC deletion mutant, a *Salmonella Enteritidis* 147 StrepR acrA-BacrEFmdtABC deletion mutant, a *Salmonella Typhimurium* nalR tolC deletion mutant and a *Salmonella Typhimurium* nalR acrABacrEFmdtABC deletion mutant. *Salmonella Enteritidis* strain 76Sa88 nalR is a well-characterized nalidixic acid resistant strain which was originally isolated from a poultry farm (Van Immerseel et al., 2002) and was used as a challenge strain in this study. *Salmonella Typhimurium* MB2136, a streptomycin resistant wild-type strain originally isolated from swine (De Cort et al., 2015), was also used as a challenge strain in this study.

Experimental Design

Forty one-day-old chicks were divided into 4 groups of 10 and each housed in a container of 1.2 m2. Two groups were given 0.5 ml of a mixture containing 2×108 CFU/ml of the *Salmonella Enteritidis* ΔacrABacrEFmdtABC strain and 2×108 CFU/ml of the *Salmonella Typhimurium* ΔacrABacrEFmdtABC strain by oral gavage on day 1 of the experiment. The two other groups were given 0.5 ml of Hank's Balanced Salt Solution (HBSS, 14175053, Invitrogen, Paisley, England) by oral gavage as a control on day one of the experiment. On day two of the experiment, one control group and one group treated with the Cl mixture were given 0.5 ml of a solution containing 2×105 CFU/ml of the *Salmonella Enteritidis* 76Sa88 nalR challenge strain by oral gavage, while the other two groups were challenged by administering 0.5 ml of a solution containing 2×105 CFU/ml of the *Salmonella Typhimurium* MB2136 streptR challenge strain by oral gavage. To evaluate colonization by the challenge strains, their numbers in caecum and spleen were determined at day 7 of the experiment. Shedding of the challenge strains was evaluated by bacteriological analysis of cloacal swabs taken on days 3 and 7.

Bacteriological Analysis

Cloacal swabs taken were directly inoculated on xylose lysine deoxycholate agar (XLD; Oxoid, Basingstoke, England) plates supplemented with 20 μg/ml nalidixic acid or 100 μg/ml streptomycin. Because the *Salmonella Enteritidis* ΔacrABacrEFmdtABC strain and the *Salmonella Typhimurium* ΔacrABacrEFmdtABC strain are unable to grow on XLD agar, XLD agar was used for the detection of the challenge strains. Samples negative after direct inoculation were pre-enriched in buffered peptone water (BPW; Oxoid, Basingstoke, England) and incubated overnight at 37° C. One ml of this suspension was further enriched by adding 9 ml tetrathionate-brilliant green broth (Merck, Darmstadt, Germany). After overnight incubation at 37° C., this suspension was plated XLD plates supplemented with the appropriate antibiotic. Samples of caecum and spleen were homogenized in BPW and 10-fold dilutions were made in HBSS. Six droplets of 20 μl of each dilution were plated on XLD plates, supplemented with 20 μg/ml nalidixic acid or 100 μg/ml streptomycin. After overnight incubation at 37° C., the number of CFU/g tissue was determined by counting the number of bacterial colonies on the plates. Negative samples were enriched as described above.

Statistical Analysis GraphPad Prism software (Version 5.0, GraphPad Software Inc., La Jolla, Calif.) was used for statistical analysis of the obtained data. A chi-square test was used to analyze differences in mortality between groups. A Fisher's test was used to analyze statistical differences between groups in the number of Salmonella-positive cloaca swabs and in the number of spleen and cecum samples positive for Salmonella. Bacterial counts in cecum and spleen were converted into logarithmic form for statistical analysis. Samples of cecum and spleen that were negative after direct plating were rated as log 10=0. Differences between groups were analyzed using a Mann-Whitney test. Differences with P-values lower than 0.05 were considered to be significant.

Results

No animals died after during the experiment and as such, there are no statistical differences in mortality between groups treated with the Cl culture and the control groups.

Faecal shedding of the *Salmonella Enteritidis* challenge strain after experimental infection was the same in the control group and the Cl culture treated group, with 5 out of 10 chickens shedding the strain in both groups on day 3 of the experiment. On day 7 of the experiment, only 6 out of 10 chickens in the Cl treated group were shedding the challenge strain, while 10 out of 10 chickens in the control group were shedding the *Salmonella Enteritidis* challenge strain. Faecal shedding of the *Salmonella Typhimurium* challenge strain was initially higher in the Cl treated group where 5 out of 10 animals were shedding the strain, while in the control group, only one chicken out of 10 was shedding the strain. However, on day 7 of the experiment, 10 out of 10 animals were shedding the *Salmonella Typhimurium* challenge strain in control group, and 9 out 10 chickens were shedding the challenge strain in the Cl treated group.

Figure 10:
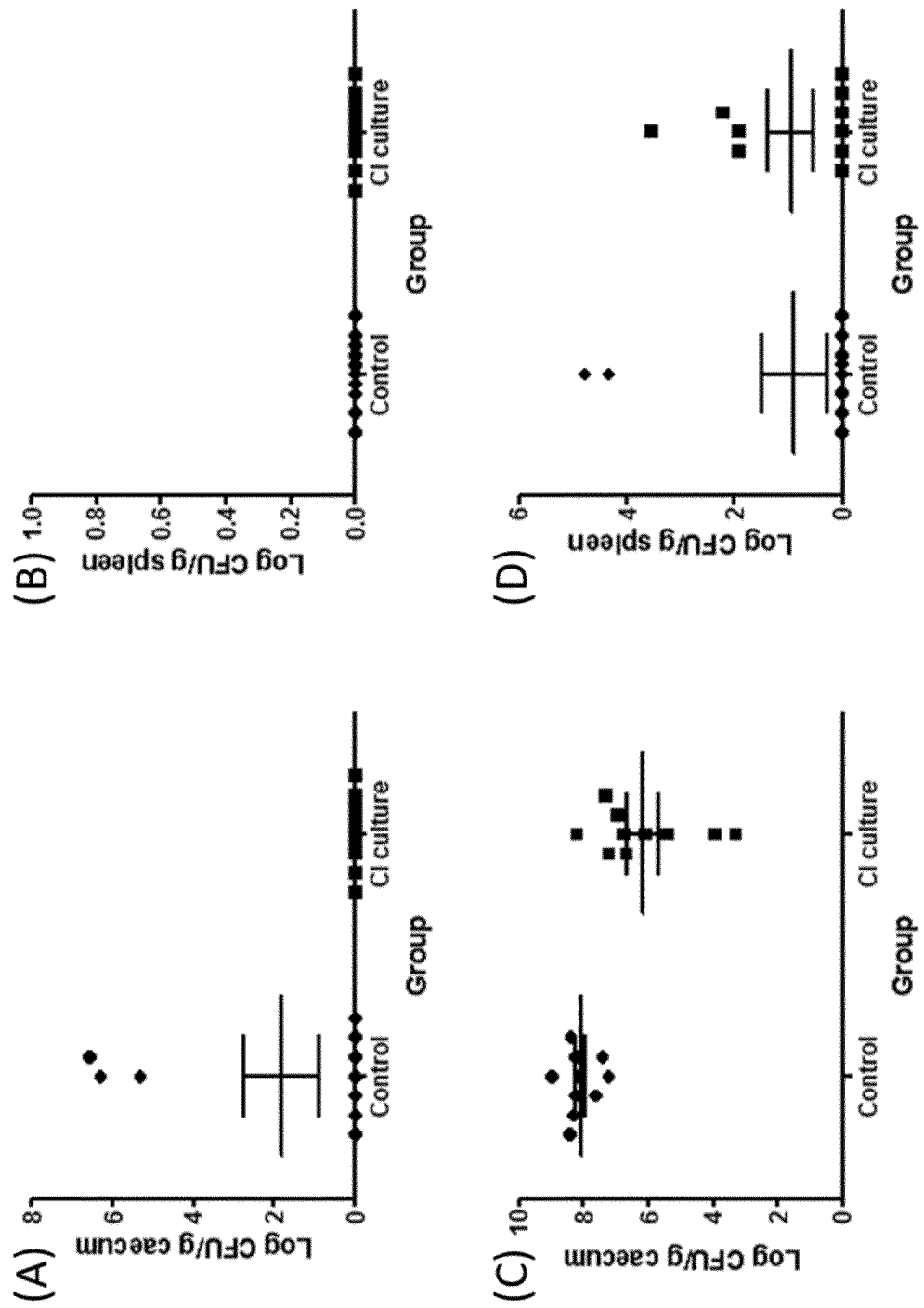

After direct plating of the caecal samples, the *Salmonella Enteritidis* challenge strain could not be detected in the group treated with the Cl culture (FIG. 10). However, in the control group, the *Salmonella Enteritidis* challenge strain could be detected in high numbers in several samples. The *Salmonella Enteritidis* challenge strain could not be detected in any of the spleen samples, in neither one of the groups. The *Salmonella Typhimurium* challenge strain could be found in significantly lower amounts in the group treated with the Cl culture when compared to the control group (FIG. 10). In the spleen however, there was no significant difference between the treated and the untreated group in colonization by the *Salmonella Typhimurium* challenge strain.

After enrichment of the caecal samples, the *Salmonella Enteritidis* challenge strain could be detected in all samples in both *Salmonella Enteritidis*-challenged groups. Similarly, the *Salmonella Typhimurium* challenge strain could be detected in all caecal samples from both the control and the Cl treated group (Table 2). After enrichment of the spleen samples, a significantly higher amount of spleens were positive for the *Salmonella Enteritidis* challenge strain in the control group when compared to the group treated with the Cl culture. There was no significant difference in number of spleen samples positive for the challenge strain between the groups that were experimentally infected with the *Salmonella Typhimurium* challenge strain (Table 2).

TABLE 2

The number of caecal and spleen samples positive for
Salmonella Enteritidis or Salmonella Typhimurium
wild-type strains on day 7 of age after experimental infection
of two days old broiler chickens treated with a CI culture.

| | Challenge serotype: | | | |
|---|---|---|---|---|
| | *Salmonella Enteritidis* | | *Salmonella Typhimurium* | |
| | Group: | | | |
| | Control | CI treated | Control | CI treated |
| Caecum | $10^a/10^b$ | 10/10 | 10/10 | 10/10 |
| Milt | 10*/10 | 2*/10 | 7/10 | 8/10 |

$^a$Number of positive samples after enrichment
$^b$Total number of samples
*Significant difference between control and CI treated groups (P-value < 0.05)

The Cl culture was administered on day one of life, and consisted of 108 CFU of a *Salmonella Enteritidis* ΔacrABacrEFmdtABC strain and 108 CFU of a *Salmonella Typhimurium* ΔacrABacrEFmdtABC strain administered simultaneously by oral gavage. The chickens were experimentally infected on day 2 of life by administering them 105 CFU of the respective challenge strain by oral gavage.

CONCLUSION

A Cl culture consisting of the ΔacrABacrEFmdtABC strains is able to offer protection against *Salmonella Enteritidis* and *Typhimurium* after experimental infection. As such, these strains can be used to help reduce *Salmonella* prevalence in broilers and eventually reduce the number of food borne *Salmonella* infections in humans.

REFERENCES

Allen-Vercoe, E. and M. J. Woodward, The role of flagella, but not fimbriae, in the adherence of *Salmonella enterica* serotype *Enteritidis* to chick gut explant. J Med Microbiol, 1999. 48(8): p. 771-80.

ANONYMOUS. 2007. Regulation (EC) No. 1237/2007 of 23 Oct. 2007 amending regulation (EC) No 2160/2003 of the Europian Parliament and of the Council and Decision 2006/696/EC as regards the placement of the market of eggs from *Salmonella* infected flocks of laying hens. off. J. Eur. Union, L280: 5-9.

Barrow, P. A., J. F. Tucker, et al. (1987). "Inhibition of colonization of the chicken alimentary tract with *Salmonella typhimurium* gram-negative facultatively anaerobic bacteria." Epidemiol Infect 98(3): 311-22.

Bohez, L., J. Dewulf, et al. (2008). "The effect of oral administration of a homologous hilA mutant strain on the long-term colonization and transmission of *Salmonella Enteritidis* in broiler chickens." Vaccine 26(3): 372-8.

Bohez, L., R. Ducatelle, et al. (2006). "*Salmonella enterica* serovar *Enteritidis* colonization of the chicken caecum requires the HilA regulatory protein." Vet Microbiol 116 (1-3): 202-10.

Bohez L, Dewulf J, Ducatelle R, Pasmans F, Haesebrouck F, Van Immerseel F. The effect of oral administration of a homologous hilA mutant strain on the long-term colonization and transmission of *Salmonella Enteritidis* in broiler chickens. Vaccine 2008; 26:372-8.

Datsenko, K. A. and B. L. Wanner (2000). "One-step inactivation of chromosomal genes in *Escherichia coli* K-12 using PCR products." Proc Natl Acad Sci USA 97(12): 6640-5.

Davison, C. E. Benson, D. J. Henzler, R. J. Eckroade, Field observations with *Salmonella Enteritidis* bacterins, Avian Dis., 43 (1999), pp. 664-669.

De Buck J, Van Immerseel F, Haesebrouck F, Ducatelle R. Protection of laying hens against *Salmonella Enteritidis* by immunization with type 1 fimbriae. Vet Microbiol. 2005 Jan. 31; 105(2):93-101.

De Cort W, Geeraerts S, Balan V, Elroy M, Haesebrouck F, Ducatelle R, et al. A *Salmonella Enteritidis* hilAssrAfliG deletion mutant is a safe live vaccine strain that confers protection against colonization by *Salmonella Enteritidis* in broilers. Vaccine 2013; 31:5104-10.

De Cort, W., S. Geeraerts, V. Balan, M. Elroy, F. Haesebrouck, R. Ducatelle, and F. Van Immerseel. A colonisation-inhibition culture consisting of *Salmonella Enteritidis* and *Typhimurium* ΔhilAssrAfliG strains protects against infection by strains of both serotypes in broilers. Vaccine 2014; 32; 4633-4638.

De Cort, W., Haesebrouck, F., Ducatelle, R., Van Immerseel, F. Administration of a *Salmonella Enteritidis* ΔhilAssrAfliG strain by coarse spray to newly hatched broilers reduces colonization and shedding of a *Salmonella Enteritidis* challenge strain. Poultry Science, 2015, 94(1):131-135.

Desin T S, Köster W, Potter AA. *Salmonella* vaccines in poultry: past, present and future. Expert Rev Vaccines. 2013 January; 12(1):87-96.

Desmidt, M., R. Ducatelle, J. Mast, B. M. Goddeeris, B. Kaspers, and F. Haesebrouck. 1998. Role of the humoral immune system in *Salmonella enteritidis* phage type four infection in chickens. Vet. Immunol. Immunopathol. 63:355-367.

EFSA 2013. EU summary report on zoonoses, zoonotic agents and food-borne outbreaks 2011. The EFSA Journal, 11, 19-73.

Gantois I, Ducatelle R, Pasmans F, Haesebrouck F, Gast R, Humphrey TJ and Van Immerseel F. FEMS Microbiology Reviews; Volume 33, Issue 4, pages 718-738, July 2009.

Gantois I, Ducatelle R, Timbermont L, Boyen F, Bohez L, Haesebrouck F, Pasmans F, van Immerseel F. Oral immunisation of laying hens with the live vaccine strains of TAD *Salmonella* vac E and TAD *Salmonella* vac T reduces internal egg contamination with *Salmonella Enteritidis*. Vaccine. 2006 Sep. 11; 24(37-39):6250-5.

Gast R K, Guard-Petter J & Holt P S (2003) Effect of prior serial in vivo passage on the frequency of *Salmonella Enteritidis* contamination in eggs from experimentally infected laying hens. Avian Dis 47: 633-639.

Hassan J O, Curtiss R 3rd. Efficacy of a live avirulent *Salmonella typhimurium* vaccine in preventing colonization and invasion of laying hens by *Salmonella typhimurium* and *Salmonella enteritidis*. Avian Dis. 1997 October-December; 41(4):783-91.

Lister S A (1988) *Salmonella Enteritidis* infection in broilers and broiler breeders. Vet Rec 123: 350.

Majowicz S E, Musto J, Scallan E, Angulo F J, Kirk M, O'Brien S J, Jones T F, Fazil A, Hoekstra R M; International Collaboration on Enteric Disease 'Burden of Illness' Studies. The global burden of nontyphoidal *Salmonella* gastroenteritis. Clin Infect Dis. 2010 Mar. 15; 50(6): 882-9.

Matsuda, K., Chaudhari, A. A. and Lee, J. H., 2011. Comparison of the safety and efficacy of a new live *Salmonella Gallinarum* vaccine candidate, JOL916, with the SG9R vaccine in chickens. Avian Dis 55, 407-12.

Methner, U., S. al-Shabibi, et al. (1995). "Experimental oral infection of specific pathogen-free laying hens and cocks with *Salmonella enteritidis* strains." Zentralbl Veterinarmed B 42(8): 459-69.

Methner, U., S. al-Shabibi, et al. (1995). "Infection model for hatching chicks infected with *Salmonella enteritidis*." Zentralbl Veterinarmed B 42(8): 471-80.

Miyamoto T, Kitaoka D, Withanage G S, Fukata T, Sasai K, Baba E. Evaluation of the efficacy of *Salmonella enteritidis* oil-emulsion bacterin in an intravaginal challenge model in hens. Avian Dis. 1999 July-September; 43(3): 497-505.

Nandre R, Matsuda K, Lee J H. Efficacy for a new live attenuated *Salmonella Enteritidis* vaccine candidate to reduce internal egg contamination. Zoonoses Public Health. 2014 February; 61(1):55-63.

Nishino K, Latifi T, Groisman E A. Virulence and drug resistance roles of multidrug efflux systems of *Salmonella enterica* serovar *Typhimurium*. Mol Microbiol 2006; 59: 126-41.

Tsukasa Horiyama, Akihito Yamaguchi and Kunihiko Nishino. TolC dependency of multidrug efflux systems in *Salmonella enterica* serovar TyphimuriumJ Antimicrob Chemother 2010; 65: 1372-1376.

Van Immerseel F, Studholme D J, Eeckhaut V, Heyndrickx M, Dewulf J, Dewaele I, Van Hoorebeke S, Haesebrouck F, Van Meirhaeghe H, Ducatelle R, Paszkiewicz K, Titball R W. *Salmonella Gallinarum* field isolates from laying hens are related to the vaccine strain SG9R. Vaccine. 2013 Oct. 9; 31(43):4940-5.

Van Immerseel, F., De Buck, J., De Smet, I., Haesebrouck, F. and Ducatelle, R. (2002). The effect of vaccination with a *Salmonella Enteritidis* aroA mutant on early cellular responses in caecal lamina propria of newly-hatched chickens, Vaccine, 20(23-24): 3034-3041.

Van Parys, A., F. Boyen, et al. (2012). "*Salmonella Typhimurium* induces SPI-1 and SPI-2 regulated and strain dependent downregulation of MHC II expression on porcine alveolar macrophages." Vet Res 43: 52.

Woodward M J, Gettinby G, Breslin M F, Corkish J D, Houghton S. The efficacy of Salenvac, a *Salmonella enterica* subsp. *Enterica* serotype *Enteritidis* iron-restricted bacterin vaccine, in laying chickens. Avian Pathol. 2002 August; 31(4):383-92.

Woodward, M. J., E. Allen-Vercoe, and J. S. Redstone, *Distribution, gene sequence and expression in vivo of the plasmid encoded fimbrial antigen of Salmonella serotype Enteritidis*. Epidemiol Infect, 1996. 117(1): p. 17-28.

The invention claimed is:

1. A *Salmonella* mutant strain comprising a deletion or inactivation of the acrAB genes, the acrEF genes, and the mdtABC genes, and wherein the *Salmonella* mutant strain is a serovar of *Salmonella enterica* subsp. *enterica*.

2. The *Salmonella* mutant strain of claim 1, wherein the acrD and mdsAB genes are unmodified.

3. The *Salmonella* mutant strain of claim 1, wherein the strain is selected from the group consisting of *Salmonella enterica* subsp. *enterica* serovar *Enteritidis, Salmonella enterica* subsp. *enterica* serovar *Typhimurium, Salmonella enterica* subsp. *enterica* serovar Hadar, *Salmonella enterica* subsp. *enterica* serovar Virchow, *Salmonella enterica* subsp. *enterica* serovar *Infantis, Salmonella enterica* subsp. *enterica* serovar Kentucky, *Salmonella enterica* subsp. *enterica* serovar Bredeney, *Salmonella enterica* subsp. *enterica* serovar Agona, *Salmonella enterica* subsp. *enterica* serovar Paratyphi B and *Salmonella enterica* subsp. *enterica* serovar *Gallinarum.*

4. A composition comprising the *Salmonella* mutant strain according to claim 1, a carrier and/or diluent, and optionally an adjuvant.

5. The composition of claim 4, wherein the composition is suitable for administration orally, by injection, or by inhalation.

6. The composition of claim 4, wherein the composition is a vaccine.

7. The composition of claim 6, wherein the vaccine is a live attenuated vaccine.

8. A method for protecting a subject against infection and/or colonization with *Salmonella*, the method comprising administering to the subject the mutant strain according to claim 1.

9. The method of claim 8, wherein the subject is a chicken.

10. The method of claim 8, wherein the subject is a broiler hen or a laying hen.

11. The method of claim 8, wherein the subject is a laying hen and the mutant strain reduces or prevents *Salmonella* infection of the reproductive organs in the laying hen.

12. The method of claim 8, wherein the mutant strain is administered to the subject orally.

13. The method of claim 8, wherein the mutant strain is administered in a prime-boost regimen.

14. A method of preventing or reducing *Salmonella* contamination of eggs, the method comprising administering to a laying hen a *Salmonella* mutant strain comprising a deletion or inactivation of the acrAB genes, the acrEF genes, and the mdtABC genes, and wherein the *Salmonella* mutant strain is a serovar of *Salmonella enterica* subsp. *enterica*.

15. The method of claim 14, wherein the laying hen produces eggs substantially free of *Salmonella* after the mutant strain is administered.

\* \* \* \* \*

UNITED STATES PATENT AND TRADEMARK OFFICE
CERTIFICATE OF CORRECTION

PATENT NO. : 10,842,861 B2
APPLICATION NO. : 16/304484
DATED : November 24, 2020
INVENTOR(S) : Filip Van Immerseel, Ruth Raspoet and Richard Ducatelle Page 1 of 1

It is certified that error appears in the above-identified patent and that said Letters Patent is hereby corrected as shown below:

On the Title Page

Item (56), foreign patent documents, cite no. 2, delete "WO WO2006129090 A2 12/2006".

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 11

<210> SEQ ID NO 1
<211> LENGTH: 1470
<212> TYPE: DNA
<213> ORGANISM: Salmonella

<400> SEQUENCE: 1

```
atgaagaaat tgctccccat ccttatcggc ctgagcctgt cggggttcag cacactaagc      60
caggcagaga acctgatgca agtttatcag caagcacgcc tgagcaaccc ggaattgcgt     120
aaatccgctg ccgatcgcga tgctgcattc gaaaaaatta cgaagcgcg tagtcctta      180
ctgccgcaac tgggtttagg tgccgactac acctacagca acggttatcg cgatgcgaac     240
ggtatcaact ccaatgaaac cagcgcttct ctgcaattaa cgcagacgct atttgatatg     300
tcgaaatggc gtgggctcac cctgcaagaa aaagcagcag gcattcagga tgtcacctat     360
cagaccgatc agcagacgct gatcctcaat accgcgaacg cgtatttaa ggtattgaac      420
gctattgatg tgcttttccta tacccaggcg caaaagagg ctatctaccg tcagttagat     480
caaacgacgc aacgttttaa cgtgggtctg gtcgccatta ccgacgtgca aaacgcccgt     540
gcgcaatatg ataccgtact ggcgaatgaa gtgaccgccc gcaacaacct ggataacgcg     600
gtagaagagc tgcgccaggt aaccggcaat tattacccgg agctggcgtc gcttaacgtc     660
gagcatttta aaaccgacaa acccaaagct gttaatgcgc tgttgaagga agcggaaaac     720
cgtaacctgt cgctgttgca ggcgcgttta agtcaggatc tggcgcgcga gcaaatccgt     780
caggcgcagg atggtcacct gccgacgctg aatttaacgg cctcaaccgg catttctgat     840
acctcttata gcggttctaa aaccaactcc acccagtacg acgatagcaa catggggcag     900
aataaaatcg gccttaactt ctccctgccg ctgtatcaag gtgggatggt taactcgcag     960
gtaaaacagg cgcagtataa cttcgtcggc gcaagcgaac agctggaaag cgcgcaccgt    1020
agcgtggtgc agaccgtacg ttcttccttt aacaatatta cgcctccat cagcagcatc    1080
aacgcgtata acaggcggt cgtttccgcg caaagttctt tggatgccat ggaagccggt    1140
tactcggtcg gtacacgtac cattgttgac gtactggatg ccaccaccac tctgtatgat    1200
gccaagcagc aactgccaa cgcgcgttat acctatttga ttaatcagtt aaatatcaaa    1260
tatgcgctcg gtacgctgaa cgagcaggat ctgctcgcgc ttaacagtac gttgggtaaa    1320
cctatcccga cgtcgccgga aagcgtagcc ccggaaacgc cagatcagga tgctgccgca    1380
gacggttata atgctcatag cgccgcgcca gcagtacagc cgaccgccgc tcgcgccaac    1440
agcaataacg gcaatccatt ccggcattga                                     1470
```

<210> SEQ ID NO 2
<211> LENGTH: 1194
<212> TYPE: DNA
<213> ORGANISM: Salmonella

<400> SEQUENCE: 2

```
atgaacaaaa acagagggtt aacgcctctg gcggtcgttc tgatgctctc aggcagctta      60
gcgctaacag gatgtgacga caaacaggac cagcaaggcg ccagcagat gccagaagtt      120
gggttgtca cactaaaaac ggaaccactg caaatcacaa ctgaacttcc gggtcgtacc      180
gttgcttacc gtatcgccga agttcgcccg caggtaagcg gcattatcct gaagcgtaat     240
ttcgttgagg gaagtgatat cgaagcggga gtctctctct atcagattga tcctgcgacc     300
taccaggcga cttacgacag cgctaagggc gatctggcaa aagcgcaggc cgccgcgaat     360
atcgctgaac tgacggtgaa gcgttatcaa aagctgctgg gtacgcagta catcagtaag     420
caggaatacg atcaggcgct ggctgacgca caacaagcga ctgccgctgt tgtcgcagca     480
aaagccgccg ttgaaaccgc acgtatcaac ctggcgtata ccaaagtcac ctcgccgatt     540
```

-continued

| | |
|---|---|
| agcggtcgta ttggtaagtc atccgtaacg gaaggcgcac tggtacagaa cggtcaggcg | 600 |
| tcggcgctgg cgacagtgca gcagctggac cctatttatg tcgatgtgac ccagtccagc | 660 |
| aatgacttcc tgcgcctgaa gcaggagctg gcaaatggtt cgctgaaaca ggaaaacggc | 720 |
| aaagcgaagg tcgacctggt gaccagcgac ggtatcaaat cccgcagtc cggtacgctt | 780 |
| gagttctccg acgtgaccgt tgaccaaacc accgggtcta ttactttgcg cgccatcttc | 840 |
| cctaacccgg atcacacctt attgccagga atgttcgttc gcgcacgtct gcaggaaggg | 900 |
| acaaaaccga cggcattact ggttccacaa cagggcgtta cccgtactcc acgcggcgat | 960 |
| gccacggtgc tggtggttgg cgctgataac aaagtggaaa cccgccaaat cgtcgcaagc | 1020 |
| caggcgatcg gcgataagtg gctggtgact gacggattga aagcgggcga ccgcgtagtc | 1080 |
| gtcagcgggc tgcaaaaagt acgtcctggc gcacaggtta agtacagga aattaccgcg | 1140 |
| gataacaaac agcaagccgc aagcggtgat caacctgctc agcccaggtc ttaa | 1194 |

<210> SEQ ID NO 3
<211> LENGTH: 3150
<212> TYPE: DNA
<213> ORGANISM: Salmonella

<400> SEQUENCE: 3

| | |
|---|---|
| atgcctaatt tctttatcga tcgccctata tttgcgtggg tgatcgccat catcatcatg | 60 |
| ttggcagggg ggctcgcgat cctcaaattg ccggtagcgc aatatccgac gattgcgcca | 120 |
| ccagcagtga cgatctccgc aacctaccct ggcgctgatg cgaaaacggt acaggatacc | 180 |
| gtcacgcagg ttatcgaaca gaatatgaac ggtatcgata acctgatgta tatgtcctcc | 240 |
| aacagtgact ccacggggac cgtgcagatc acgctgacct ttgaatccgg caccgatgcg | 300 |
| gatatcgcgc aggttcaggt tcagaacaag ttgcaactgg caatgccgtt acttccccag | 360 |
| gaagtacagc aacagggcgt gagcgttgag aagtcctcaa gtagcttcct gatggtagtg | 420 |
| ggcgtcatta acaccgacgg caccatgacc caggaggata tttcggatta cgttgccgcc | 480 |
| aatatgaaag atccgatcag ccgtacctct ggggtgggcg acgtccagct gtttggttcg | 540 |
| caatatgcga tgcgtatctg gatgaatccg acagagctga ccaaatacca actgacgccg | 600 |
| gtcgacgtga ttaacgcgat caaagcgcag aacgcccagg tcgcggcagg tcagctcggt | 660 |
| ggtacgccgc cggttaaagg ccagcagctt aacgcatcga ttattgccca aacgcgtctg | 720 |
| acctcaacgg atgagtttgg caaaatcctg ctgaaagtga atcaggatgg ctcccaggtt | 780 |
| cgtctgcggg atgtagcgaa aattgagctt ggcggcgaga actacgacgt cattgcgaaa | 840 |
| tttaacggtc agccagcgtc aggtcttggc atcaaactgg ctaccggcgc caacgcgctg | 900 |
| gataccgcta ccgctattcg tgccgaactg aaaaaaatgg aaccgttctt cccgccaggg | 960 |
| atgaaaatcg tctacccgta tgacaccacg ccgttcgtga agatctctat tcatgaagtg | 1020 |
| gtaaaaacgc tggtcgaagc gattatcctc gtgttcctgg tgatgtacct gttcctgcag | 1080 |
| aacttccgcg cgacgttgat tccgactatt gcggttccgg tggtgttgtt gggaaccttt | 1140 |
| gccgtgcttg cggcattcgg tttctcgata aacacgctga cgatgttcgg gatggtgctc | 1200 |
| gccatcggct tgctggtgga tgacgccatc gtggtggtcg agaacgtcga acgtgttatg | 1260 |
| acggaagaag gccttccgcc gaaggaagcg acgcgcaaat ccatgggcca gattcagggc | 1320 |
| gcattggtgg gtatcgcgat ggtactgtcg gcggtatta ttccgatggc cttcttttggc | 1380 |
| ggctcaaccg gggcaattta tcgtcagttc tctatcacca tcgtatcggc gatggcgctg | 1440 |
| tcggtgctgg tcgcgctgat cctgacgcct gcgctgtgcg cgacgatgct caaacccgtc | 1500 |

```
gccaaaggcg atcatggcga agggaaaaaa ggcttttcg gctggtttaa ccgcctgttt    1560
gataagagca cgcatcacta caccgatagc gtaggcaata ttctgcgcag caccgggcgt    1620
tatctgctgc tctatctcat tatcgtcgtc ggtatggctt atctgttcgt tcgtctgcca    1680
agctctttct tgccggatga agaccagggc gtattcctga caatggtcca gctccccgcg    1740
ggcgcaacgc aagagcgcac gcaaaaagtg ctggatgagg tcacggatta ctatctgaac    1800
aaagagaaag ccaacgttga atcggtattc gccgtcaacg gcttcggttt tgcagggcgc    1860
ggtcagaata ccggtattgc attcgtgtcg ttgaaagact gggccgatcg tccaggcgaa    1920
aaaaacaagg ttgaagcgat tacccagcgg gcaaccgcag cgttttcaca aattaaagat    1980
gcgatggtct tcgcctttaa cctgccggcg atcgttgagc tgggcaccgc aaccggcttt    2040
gacttcgagt tgattgacca ggcgggactt ggtcatgaaa aactcaccca ggcacgtaat    2100
cagttgttcg gcgaggtggc gaaatatcct gatctgctgg tcggcgttcg acctaacggt    2160
ctggaagata cgccgcagtt taaaatcgat atcgaccagg aaaaagctca ggcgctgggc    2220
gtatctatta gcgacattaa taccacgctg gcgcagcat ggggcggcag ctatgtaaac    2280
gactttatcg atcgcggtcg tgtgaagaaa gtttacgtga tgtccgaagc gaaataccgc    2340
atgttgccgg atgatattaa cgactggtac gttcgtggta gcgatggtca gatggtgcca    2400
ttctccgcat tctcctcttc ccgctgggaa tatggttcgc cgcgtctgga acgctataac    2460
ggtctgcctt cgatggaaat tctggggcag gcggcgccag gcaagagtac cggtgaagcg    2520
atggcgatga tggaagaact ggccagcaag ctgccgtcag gcattgggta tgactggacc    2580
gggatgtcct accaggagcg gttgtccggc aaccaggccc ctgccctgta tgctatatcg    2640
ctgatcgtcg tcttcctgtg tctggcggca ttgtatgaga gctggtctat cccgttctcc    2700
gtaatgctgg ttgttccgct tggggttatc ggcgcgctgc tggctgcgac cttccgcgga    2760
ctgactaacg acgtttactt ccaggtgggc ctgctcacaa ccattgggtt gtcggcgaag    2820
aacgcgatac ttatcgtcga attcgccaaa gacttaatgg ataaagaagg gaaaggtctg    2880
gtagaagcga cgctggaggc cgtccggatg cgtttgcgcc cgattctgat gacctcgtta    2940
gcgttcatgc tgggggttat gccgctggtt atcagttccg cgcgcgggttc cggcgcgcag    3000 aatgcggtag gtactggcgt actgggcggg atggtaacgg caaccgtact ggctattttc    3060
ttcgtaccgg tcttcttcgt ggtggtacgc cgccgcttta ccgtaaaaag cgaagatatt    3120
gagcatagtc attcgacaga acatcgctga                                     3150
```

<210> SEQ ID NO 4
<211> LENGTH: 3114
<212> TYPE: DNA
<213> ORGANISM: Salmonella

<400> SEQUENCE: 4

```
atggcgaatt ttttatcga tcgccccatt tttgcctggg tgctggctat cctgttgtgt      60
ctgacagggg cgttagccat tttctcttta cctgttgaac aatatcccga tctggcgccg    120
cccaacgtac gtattaccgc gaattatccg ggagcgtcgg cgcaaacgct ggaaaatacc    180
gtaacccagg ttattgagca gaatatgacg ggcctcgata tctgatgta catgtcatca    240 caaagcagcg gaaccggaca ggcgaccatc accctgagct ttattgcggg aaccgatcct    300
gatgaggcgt tcagcaggt gcaaaaccag ttacagtccg cgatgcgtaa actgccgcag    360
gcggtacagg atcaaggcgt cacggtacgc aaaacgggcg ataccaatat tttgaccatc    420
```

```
gctttcgtct ctaccgacgg ttctatggac aagcaggata tcgccgacta cgtcgccagt    480
aatattcagg acccgctcag ccgcgtcaac ggcgtcggcg atattgacgc ttatggttca    540
cagtactcta tgcgtatctg gctcgatccg gccaaattga atagttttca gatgaccacg    600
aaagacgtga ccgatgcaat tgagtcgcag aatgcgcaaa tcgccgtcgg gcagcttggc    660
ggtacgcctt cggtcgacaa acaggcgctg aacgccacca ttaatgcgca gtcattgctg    720
caaacgccgc aacaatttcg cgatatcacc ctgcgcgtta atcaggacgg ttccgaggtc    780
aaactgggcg atgtcgccac cgtggagctg ggggcggaaa gtatgactac cctcagccgt    840
tttaacggca atccggcttc cggtcttggc gttaagctgg cctccggcgc gaacgaaatg    900
gcgaccgcga agctggtact ggatcgcctc aacgagctgg cgcagtactt ccctcacggc    960
ctggaataca agatcgcgta tgaaaccacc tcctttgtca agcctcgat  tatcgatgtg   1020
gtcaaaacgt tgctggaagc tatcgcgctg gttttcctgg tgatgtatct gttcctgcaa   1080
aactttcgcg ccacgctcat tccgacgatc gccgtgccgg tagtattaat gggcaccttc   1140
tccgtgcttt acgcgtttgg ctacagtatt aacacattaa ccatgttcgc gatggtgctg   1200
gcgatcgggc tcctagtcga cgatgccatc gtggtggtgg aaaacgtcga acgtatcatg   1260
agcgaagaag ggctcacgcc gcgtgaagcg acgcgcaaat ccatgggaca aatccagggg   1320
gcgctggtcg gtatcgcgat ggtgctgtct gcggtattcg tgccgatggc gttctttggc   1380
ggtaccaccg gggcgattta tcgtcagttt tctattacca ttgtctcggc aatggtgctg   1440
tcggtgctgg tcgccatgat cctgacgccg gcgctgtgcg caacgttatt aaaaccgctg   1500
cacaaaggcg aacagcacgg gcaacgcgga ttttcggct ggtttaaccg taccttcaat   1560
cgtaatgccg aacgttatga gaaggcgta gcgaaaattt tgcatcgcag cctgcgctgg   1620
attctgattt atgttctgtt acttggcgga atggtgttcc tgttttttgcg cctccccacc   1680
tccttcctgc cgcaggaaga tcggggcatg ttcactacgt ctatccagct accgagcggt   1740
tctacgcaac agcagaccct gaaagtcgtt gaaaaggttg aaaactatta cttcacccat   1800
gagaaagaca acattatgtc ggtcttctcg acggtaggtt ccggccctgg cgggaatggg   1860
caaaacgtcg cgcgcatgtt tgttcgcttg aaagactggg acgcgcgcga tcccaccacc   1920
ggctcctcgt tcgccattat tgagcgggcg acaaaagcat ttaaccagat taaagaagct   1980
cgcgtcttcg ccagcagccc gccggcaatt agcggtctgg gcagctccgc cggttttgat   2040
atggaattac aggatcacgc cggagcaggc catgacgcgc tgatggccgc acgagatcaa   2100
ctcattgagc tggccgggaa aaacagttcc ttgacccgcg tgcgccacaa cggcctggac   2160
gacagcccgc aactgcaaat tgatattgac caacgaaaag cgcaggcgct gggcgtatcg   2220
attgacgata tcaacgacac cctgcaaaca gcctggggat cgagctacgt caacgacttt   2280
atggaccggg gccgcgtgaa gaaggtctat gttcaggccg cagcgaaata tcgtatgttg   2340
ccggatgata ttaatctttg gtatgtccgt aacaaagacg gcggcatggt ccccttctcc   2400
gccttcgcca cctcgcgctg ggaaaccgga tcgccgcgtc tggaacgcta taacggctat   2460
tcggcggtag aaattgtcgg agaggccgcg ccgggggtca gtaccgggac ggcaatggat   2520
gtcatggagt cgttggtgca tcagctaccg ggcggttttg gcctggaatg gacagccatg   2580
tcttaccagg aacggctctc cggcgcgcag cgccccgcgc tgtacgctat ttcgctatta   2640
gtcgtcttcc tgtgtctggc ggcattgtat gaaagctggt cggtgcccttt ctcggtgatg   2700
ctggttgtgc cgctcggggt catcggcgcg ctactcgcta cctggatgcg cgggctgaa    2760
aacgatgttt acttccaggt ggggctgttg accgttatcg gcctctcggc gaaaaacgcg   2820
```

| | |
|---|---|
| attctgattg tggaattcgc caacgaaatg aatcagaagg acacgcgct gttagacgcc | 2880 |
| acgctgtacg ccagccgcca acgcctgcga ccgatactga tgacttcgct ggcgtttatc | 2940 |
| tttggcgtat tgccgatggc caccagcacc ggggcaggct cgggtagcca acatgctgtc | 3000 |
| ggaaccggcg tgatggggggg aatgatctca gcaaccgttc tggctatctt ctttgtaccc | 3060 |
| ctgtttttcg tgctgatacg tcgccgcttc ccgctgaagc cgcgcccgaa ataa | 3114 |

<210> SEQ ID NO 5
<211> LENGTH: 3114
<212> TYPE: DNA
<213> ORGANISM: Salmonella

<400> SEQUENCE: 5

| | |
|---|---|
| atggcaaact tttttattag acgtcctatt ttcgcctggg ttctggccat tatcctgatg | 60 |
| atggctggcg cactggcaat aatgcaactt cccgttgcgc agtatccaac cattgcgccg | 120 |
| ccagcggttt ctatttctgc aacctatcct ggcgcggatg cgcagacggt acaggatacg | 180 |
| gttactcagg ttatcgaaca aaatatgaac ggtatcgata acctgatgta tatgtcctct | 240 |
| accagcgact ctgctggtag cgtgaccatc accctgacct tccagtccgg aaccgatccg | 300 |
| gatatcgcgc aggttcaggt gcaaaataaa ttgcagctcg ccacgccttt actgccgcaa | 360 |
| gaagtccagc agcaggggat tagcgttgaa aaatccagca gcagcttttt gatggtcgcc | 420 |
| gggttcgtct cagataatcc gaacactacc caggacgaca tctctgacta tgtcgcctct | 480 |
| aacattaagg attctatcag ccgtctgaat ggtgtgggcg acgttcagct atttggcgca | 540 |
| cagtacgcca tgcgtatctg gctggatgcg aatctgctaa ataaatacca gctcacgcca | 600 |
| gttgacgtca tcaaccagtt aaaagtacag aacgaccaga ttgcggcagg ccaactgggc | 660 |
| ggcacgccag cattaccggg ccagcagctt aacgcctcaa tcatcgccca acgcgtctg | 720 |
| aaagatccgg aagagttcgg caaagttacg ttgcgcgtca ataccgacgg ctctgtcgtc | 780 |
| catctcaaag atgtcgcgcg tattgagctt ggcggtgaaa actataacgt tgtagcgcgc | 840 |
| attaacggta aaccggcctc cggtctcggt attaaactgg cgaccggcgc taacgcgctg | 900 |
| gataccgcaa ccgcaatcaa agtgaaactg gcggagctgc agccttctt ccctcaggga | 960 |
| atgaaggtgg tttatcctta tgacacaacg cccttcgtaa aatatctat ccacgaagtg | 1020 |
| gtaaaaacgc tgtttgaagc gattattctg tgttcctgg taatgtatct gttcttacag | 1080 |
| aatatccggg caaccctgat tcctaccatc gctgttcctg tcgtgttgct aggcactttt | 1140 |
| gcggtactcg ccgcctttgg ctattccatc aatacctga cgatgtttgg tatggtactg | 1200 |
| gcgataggc tgttggttga cgatgcgata gtggtcgtag aaaacgttga acgtgtaatg | 1260 |
| atggaggata accttttctcc ccgagaggcg acggaaaaat ccatgtcgca gattcaggga | 1320 |
| gcgctggttg gtatcgcgat ggtactgtct gcggtattta tcccgatggc cttttttggc | 1380 |
| ggctcgaccg gggcaattta tgccagttc tctattacta ttgtttcagc aatggcgcta | 1440 |
| tccgttctgg ttgcgttgat tctgacgcca gcactgtgcg ctacgctgct aaacccgta | 1500 |
| tctgctgaac atcacgagaa aaaagcggc ttctttggct ggttcaatac caggtttgac | 1560 |
| cacagcgtta accactatac taacagcgta agcggcatcg tgcgtaatac gggtcgctat | 1620 |
| ctcattatct atctacttat tgtagtcgga atggcggttc tgtttttacg cctcccgacc | 1680 |
| tccttcctgc cggaagaaga tcagggagta ttcctgacca tgattcagct ccctctggc | 1740 |
| gctacgcaag aacgtacgca gaaagtgctg gatcaagtca ctcattacta cctgaataat | 1800 |

-continued

```
gaaaaagcga acgtcgaaag cgtgtttacc gtaaacgget ttagctttag cggtcaggga       1860
caaaactcag ggatggcatt tgtcagcctt aaaccctggg aagagcgtaa cggtgaagaa       1920
aatagcgtcg aagccgttat cgccagagcg acacgcgcct ttagccagat tcgcgacggg       1980
ttggtgttcc ccttcaacat gccggcaatt gtcgagttag gtaccgcaac aggtttcgac       2040
ttcgaactga ttgatcaggg aggactcggt cacgatgcgt taacaaaagc gcgtaatcaa       2100
ctcctgggta tggtcgcgaa gcatcctgat ctattagtgc gcgtacgccc gaacgggctg       2160
gaagacacgc cacagttcaa gctggatgtc gatcaagaaa aagcgcaggc gctcggcgtt       2220
tcgctgtctg atatcaacga aaccatctcc gcggcgttgg gcggctatta cgttaacgac       2280
tttatcgatc gcggacgagt gaaaaaagta tacgttcagg ctgacgctca gttccgtatg       2340
ctgccgggag atatcaacaa tctttatgtt cgcagcgcta atggcgagat ggtgcccttc       2400 tctacctta gctcagcacg gtggatttat ggttcgccac gcctggaacg ctataacggg        2460
atgccgtcaa tggaactgct cggcgaagca gcacccggac gaagcaccgg tgaagccatg       2520
tcgttaatgg aaaacctggc ttcacagcta ccaaacggta ttggctatga ctggacaggt      2580
atgtcgtatc aggaacggtt gtcaggtaac caggcgccgg cgctgtacgc aatctcactc       2640
attgtcgttt tcctctgcct tgccgctctg tatgaaagct ggtcaattcc gttctcggta       2700
atgctggtcg taccgctcgg cgtggttggc gctctgcttg cagcgtcatt gcgcggtctg       2760
aacaatgacg tttacttcca ggttggcttg ttaaccacta ttggcctttc tgctaaaaac       2820
gccatcctga ttgtcgagtt cgccaaagat ctcatggaaa agaaggacg tggattgatt        2880 gaagcgacgc tggaagcatc ccgtatgcgt ttacgtccta ttctaatgac ctcgctggcc       2940
tttattctcg gggtaatgcc gttagttatc agtcgtggcg caggtagtgg tgcacagaac       3000
gcagtaggca caggggttat gggggaaatg ttaaccgcaa ccttattagc tatcttcttc       3060
gtgccggtat tcttcgttgt tgtaaaacgc cgatttaatc gccatcatga ttaa            3114
```

<210> SEQ ID NO 6
<211> LENGTH: 1158
<212> TYPE: DNA
<213> ORGANISM: Salmonella

<400> SEQUENCE: 6

```
atgacgaaac atgccaggtt ttcactcctg ccctcattca tcatattctc tgctgcgctg        60
ctggccggtt gtaatgacca gggagatacc caggctcatg ccggcgagcc gcaagtcacc       120
gtccatgtgg tcgaaacagc gccgctagcc gtaacgaccg aacttcccgg acgtacgtcc       180
gcatttcgca ttgcggaggt tcgcccccag gtgagcggga tcgtgcttaa aagaaacttc       240
accgaaggta gcgatgtaga ggccgggcag tcgctctatc agatcgatcc tgccactat       300 caggctgatt atgacagcgc taaaggcgaa cttgctaaaa gcgaagcggc tgcggctatc       360
gcgcacctga cggtcaaacg ctatgttcca ctggtcggca caaatatat cagccaacag       420 gaatatgatc aggcgattgc cgacgcccgc caggccgatg ccgccgttgt ggcggcaaaa       480
gccgctgttg aaagcgcgcg tattaacctt gcgtatacca aagtcacctc acccatcagc       540
gggcgtatag gaaaatctaa tgtgactgaa ggcgcgctgg tgactaatgg tcagtcaact       600
gaactggcta ccgtgcaaca actcgatccg atttatgtcg acgtgacgca atcaagcaac       660
gactttatgc gactcaagca atccgtcgaa caaggtaacc tgcataaaga cagcgccagt       720
agcacggttc aactggtaat ggaaaatggt caggtctacc cgattaaagg cacgctgcaa       780
ttttccgacg ttaccgtaga tgaaagcacc ggctctatca cgctcagggc ggtgttccct       840
```

| | |
|---|---|
| aacccgcaac acagtctgct tcccggtatg tttgttcgcg cccgcattga tgaaggcgtc | 900 |
| cagcccaatg ccatccttgt cccccagcag ggcgtaaccc gcacgccgcg cggcgacgca | 960 |
| atggtgatgg tggttaacga taaaagccag gtcgaagccc gcaatgtcgt ggcggcgcag | 1020 |
| gctattggcg ataaatggct catcagcgaa gggttaaaac cgggcgataa ggtcatcgtc | 1080 |
| agcggcttac aaaaagcgcg accgggcgtc caggtgaaag ccactaccga tgctcctgca | 1140 |
| gcgaaaacgg cgcaataa | 1158 |

<210> SEQ ID NO 7
<211> LENGTH: 1242
<212> TYPE: DNA
<213> ORGANISM: Salmonella

<400> SEQUENCE: 7

| | |
|---|---|
| atgaaaggca gtaatacttt ccgctgggca atagcgattg gggttgtagt ggccgccgcc | 60 |
| gcattctggt tctggcatag ccgtagcgaa agcccgaccg ccgcgccagg cgtcgccgcg | 120 |
| caagcgccgc ataccgcctc cgcaggtcgc gcggtatgc gcgacggccc tctggcgccg | 180 |
| gtacaggccg cgaccgcgac cacgcaggcc gtaccgcgct atctgagcgg gctgggtacc | 240 |
| gtgaccgccg cgaataccgt tacggtgcgt agccgcgtgg atggtcaact catcgccctg | 300 |
| cactttcagg aaggtcagca ggtcaacgca ggcgatctgc tggcgcaaat cgatcccagc | 360 |
| cagtttaagg tcgccctggc gcaggctcag ggacagttgg cgaaagataa cgctacgctg | 420 |
| gcgaatgcgc gtcgtgatct ggcgcgctat cagcaactgg caaaaaccaa tctggttcc | 480 |
| cgtcaggaac tggatgcgca acaggcgctg gtcaacgaaa cccagggaac cattaaagcg | 540 |
| gatgaagcta atgtcgccag cgcgcagtta cagctcgact ggagtcgtat cacggccccg | 600 |
| gtctcgggac gcgtgggtct gaaacaggtg gatgtcggca accagatttc cagcagcgat | 660 |
| accgcaggta ttgtcgtcat tacgcaaacg caccccgattg atctcatttt tactctgccg | 720 |
| gaaagcgata tcgcgaccgt agttcaggca cagaaagcgg ggaaagcgct ggtcgtagaa | 780 |
| gcctgggatc ggactaactc gcacaaattg agcgaaggtg tgttgctcag tctggacaac | 840 |
| cagattgatc ccacgacggg aacgatcaaa attaaagcgc gctttaccaa tcaggacgat | 900 |
| acgctgttcc ccaatcaatt tgtgaacgcc cggatgctgg tcgataccga acaaaatgcc | 960 |
| gttgtggtgc ctgccgcggc ggtgcaaatg gcaatgagg ccactttgt gtgggtgctg | 1020 |
| aacgacgaaa ataacgtcag caagaagcgg gtaaaaatcg gtattcagga taaccgaaac | 1080 |
| gtggtgatca cgcagcgctt atcggcaggc gatcgcgtcg ttaccgatgg tattgatcgg | 1140 |
| ctgacggaag gcgcaaaagt cgaggtcgtt gagccgcaaa ccaccgtggc ggatgaaaaa | 1200 |
| tccccttccc gccatgaagg tcaaaaagga gcgcgcgcct ga | 1242 |

<210> SEQ ID NO 8
<211> LENGTH: 3123
<212> TYPE: DNA
<213> ORGANISM: Salmonella

<400> SEQUENCE: 8

| | |
|---|---|
| atgcaggtat acctccgggc agcacgggc ggcccttcgc gtctgtttat ctgcgcccc | 60 |
| gtggccacca ctctgctgat ggcggcgatt ttactcgccg ggattatcgg ctatcgcttc | 120 |
| ctgcccgtcg ccgcttttgcc ggaggtcgac taccccacta ttcaggttgt tacgctctac | 180 |
| cctggcgcca gcccgatgt catgacctcc gccgtcaccg cgccgcttga gcgccagttc | 240 |

```
ggccagatgt caggactgaa gcagatgtcg tcgcaaagct ccggcggcgc gtcagtggta    300
acgctacagt ttcagttgac gctgccgctg gacgttgccg agcaggaagt acaggcggcg    360
attaacgcag ccaccaattt attgccttcc gacctgccga atccgccgat ttacagcaaa    420
gtcaatccgg cggacccgcc gattatgacg cttgccgtca cctcaaactc gatgccgatg    480
acccaggtag aggacatggt agaaacccgc gtggcgcaga agatctcaca ggtctccggc    540
gtcgggctgg tgacgcttgc cggcgggcag cgccctgcgg tacgcgtaaa actgaatgct    600
caggctgtcg ccgcgctcgg tctgaccagc gaaacggtcc gtaccgcaat taccggcgcc    660
aacgtcaact cggcgaaagg cagtctggat ggccccgaac gggcggtgac gctttctgct    720
aacgatcaga tgcagtctgc cgacgaatac cgcaggctta tcatcgcgta tcaaaacggc    780
gcgccggtac ggctgggcga tgtcgccacc gtcgaacagg gggcggaaaa tagctggctc    840
ggcgcatggg cgaatcaagc gccggctatc gtgatgaacg ttcaacgcca gcctggcgcc    900
aatatcattg cgacagcgga cagcattcgc cagatgctgc cccagcttac cgaaagcctg    960
ccaaaatcgg tgaaggtcac ggtcctgtcc gatcgcacca ccaatattcg cgcttccgtg   1020
cgcgataccc agtttgaact gatgctggcg atcgcgctgg tcgtcatgat tatctatctg   1080
tttttacgta atattcccgc cacaattatt cccggcgtcg ccgtaccgct gtcgcttatc   1140
ggcacctttg cggtgatggt gttttttggat ttttccatta ataacctgac gctgatggcg   1200
ctcactatcg ccacgggttt cgtggtggac gatgcgattg tggtgatcga gaacatctcg   1260
cgctacatcg aaaaaggaga aaaaccgctg gcggcggcgc tcaaaggcgc gggtgaaatc   1320
ggctttacca ttatttccct cacctttca ctgattgcgg tgctgatccc gttgctcttt   1380
atgggcgata ttgttggtcg actgttccgc gaatttgcgg tgacgttggc ggtagcgatt   1440
ttaatctccg ccgtcgtctc tttgacgctc acgcccatga tgtgcgcgcg tatgctcagc   1500
cagcagtctc tgcgtaaaca aaaccgcttt tcccgcgcct gcgagcggat gtttgaccgc   1560
gtgatcgcca gctacggacg tggattagcg aaagtgctca accatccgtg gcttacattg   1620
agcgtggcat tcgccacgct cctgctcagc gttatgctgt ggatagtcat tccgaaaggg   1680
ttctttccgg tacaggataa cggcattatc caggaacgc tgcaggcgcc gcaatcgtca   1740
tcgtatgcca gtatggcgca acgtcagcgc caggtggcgg agcggatatt acaggacccg   1800
gcggtgcaaa gcctgacgac ttttgttggc gtagacggcg ctaaccccac gctgaatagc   1860
gcgcgcctgc aaattaacct caagccgctg gatgcgcgtg atgaccgcgt gcagcaggtg   1920
atctcccggc tgcaaaccgc cgtggcgacg attcccggcg tggagctgta tctccagccg   1980
acgcaggatt taaccatcga cacgcaggtc agccgcacac agtatcagtt taccctgcag   2040
gccacgacgc tcgatgcgct cagccactgg gtgccaaaac tgcagaacgc gctacagtcg   2100
ttgccacagc tctctgaggt aagcagcgac tggcaagatc ggggattagc ggcctgggtg   2160
aatgtcgacc gcgacagcgc cagccgtctg ggtatcagca tggcggatgt ggataacgcg   2220
ctctacaacg cgttcggaca acgcctgatt tcaacgattt atacccaggc gaaccagtac   2280
cgtgtcgtgc tggaacataa taccgccagc atgccgggcc tggcggcgct ggagacgatt   2340
cgcctgacga gccgcgacgg cggcaccgta ccgctcagcg cgattgcccg cattgagcag   2400
cgcttcgctc cgctctccat caatcattta gatcagttcc cggttacgac attttcgttt   2460
aacgtgccgg agagctattc gctcggcgat gcggtgcagg cgattctcga tacggaaaaa   2520
acgctcgccc tgccagcgga tattacaacg cagtttcagg gtagtacgct cgccttccag   2580
gcggcgctag gcagcaccgt ctggcttatt gtcgccgccg tggtggcgat gtatatcgtg   2640
```

```
ctcggcgtgc tgtatgagag ttttatccat ccgattacga ttctctcaac gctgcctacg    2700
gcgggcgtcg gcgcgctgct ggcgctgatc atcgctggta gcgagctcga tattatcgcc    2760
attatcggca ttattttgct gatcggcatc gtgaagaaaa acgccatcat gatgattgac    2820
ttcgccctcg ccgccgaacg cgaacagggg atgagtccgc gcgacgctat cttccaggcc    2880
tgtctgctgc gttttcgacc gattctgatg accacgctgg cggcgttgct cggggcattg    2940
ccattaatgt tgagtaccgg cgttggcacg gaattacgtc gcccgttggg gatcgcgatg    3000
gtaggcggct tactggtcag ccaggtatta actctgttta ccacaccggt gatttatctc    3060
ctgtttgacc gcctgtcgct gtacgtgaaa agtcgctttc gcgccataa agaggaggcg    3120 tag                                                                    3123
```

<210> SEQ ID NO 9
<211> LENGTH: 3081
<212> TYPE: DNA
<213> ORGANISM: Salmonella

<400> SEQUENCE: 9

```
atgcgctttt tcgccctttt catctaccgc ccggtcgcca ccattttgat tgccgccgcc      60
attacgctgt gcggcattct gggctttcgt ctgctgccgg tcgccccgct gccgcaggtc     120
gatttcccgg tgattatggt tagcgcctcg ctgccgggcg cctcgccgga aaccatggct     180
tcgtcggtgg cgacgccgtt ggaacgctct ttgggacgca ttgcaggcgt caatgaaatg     240
acctccagca gctcgctcgg cagtacacgc attattctcg aatttaattt cgatcgtgat     300
attaacggcg cggcgcgcga cgtgcaggcc gccattaacg ccgcgcaaag cttgttgcca     360
ggcggaatgc ccagccgccc gacttatcgc aaggccaacc cgtccgacgc gccgattatg     420 atttttaacgc ttacctcgga gagctggtca cagggcaaac tgtatgattt cgcctctacc     480
caactggcgc aaaccatcgc gcaaattgac ggcgtcggcg atgttgacgt cggcggcagc     540
tccctgcccg cagtacgtgt aggcttaaac ccgcaggcgc tctttaacca gggcgtctcg     600
ctggatgagg tccgcgaagc gatcgacagc gccaacgtac gccgaccgca aggcgcaatt     660
gaagatagcg tccaccgctg gcaaatccag accaacgacg aactgaaaac cgccgccgaa     720
tatcagccgc tgattattca ctataacaac ggcgcggcgg tacgcctggg cgacgtcgcc     780
agcgtcaccg actcggtgca ggatgtccgt aacgccggga tgacgaacgc taaacccgct     840
attttgttga tgatccgcaa gctgccggag gccaatatta ttcagacggt cgacggcatc     900
cgggcaaaac tgccggaact gcgggcaatg atccccgccg ctatcgattt acaaatcgcc     960
caggatcgtt cgccgacgat tcgcgcatcg ctgcaagagg tagaagagac actggctatc    1020
tctgttgcgc tggtgatcct ggtggtgttt ttattcctgc gctccgggcg cgccacgcta    1080
attcccgccg tcgccgttcc cgtttcgctc atcggcacct tcgccgccat gtatctgtgc    1140
ggcttcagcc tcaacaatct gtcgctgatg gcgctgacta tcgcgaccgg atttgtcgtt    1200
gatgatgcca ttgtggtgct ggaaaatatc gcccgccatc tggaggcggg aatgaaacct    1260
ttgcaggcgg cattacaggg tacgcgagaa gttgggttta cggtcatctc catgagtctg    1320
tcgctggtgg cggtatttct gccgctgctg ttaatgggcg gcctgccagg acgattatta    1380
cgggaattcg ccgttaccct tcggtggcg attggcattt cgctggtggt ctcgctcacg    1440
ctgacgccga tgatgcgg ctggatgctt aaatcaagca aaccgcgcac ccaaccgcgt    1500
aaacggggcg ttggccgtct gctggtcgcc ttgcaacagg ttacggcac gtcattaaaa    1560
```

```
tgggtgctta accatacgcg tcttgtcggt gtggttttc ttggcaccgt tgcgctgaac    1620
atctggcttt atatcgccat ccctaaaaca ttctttccgg agcaggacac cggcgtgttg    1680
atgggcggta ttcaggctga ccaaagcatc tctttccagg ccatgcgcgg caagctgcag    1740
gattttatga aaattattcg cgacgatccg gcggtgaata atgtcactgg ttttaccggc    1800
ggatcgaggg tgaatagcgg catgatgttt attacgctga agccgcgcgg cgaacgcaaa    1860
gagacggcgc agcaaatcat tgatcgactg cgggtcaaac tggcaaaaga acctggcgcc    1920
aggctgtttc tgatggcggt acaggatatt cgcgtcggcg ggcggcaggc taacgccagt    1980
taccaatata cgttgctgtc tgactctctg gcggcgctgc gcgaatggga gccgaaaata    2040
cgcaaagcgc tctcggccct gccgcaactg gcggacgtaa actccgacca gcaggataac    2100
ggcgcggaga tgaaccttat ctacgaccgc gacaccatgt cacggctggg tattgatgtt    2160
caggccgcaa acagtctgtt aaataatgct ttcggccagc ggcaaatttc caccatttat    2220
cagccgatga accagtataa agtggtgatg aagtcgatc cgcgctatag ccaggatatc    2280
agcgcgctgg agaaaatgtt cgttatcaac cgtgacggaa aagcgattcc cctctcttat    2340
ttcgcccaat ggcggcccgc caatgcgccg ctgtcggtga accatcaggg actttccgcg    2400
gcgtccacga ttgcctttaa cctgccgacc ggcacatcgt tatcgcaggc gacagaggcc    2460
attaatcgca ccatgacgca gcttggcgtc ccctcgacgg tacgcggcag ttttccgga    2520 acggcgcaag tcttccagca gaccatgaat tcacagctta ttttgatagt ggcggcgatc    2580
gctaccgtct acattgtgct ggggatactg tacgaaagct acgtccatcc actgaccatt    2640
ctctctactc tgccatcggc gggcgttggg gcgcttctgg cgctggaact cttcaatgcc    2700
cctttcagcc taatcgccct gatagggatc atgctattaa ttggcattgt gaagaaaaac    2760
gccattatga tggtcgattt tgcgcttgaa gcgcaacgaa gcggcggcct gacgccggaa    2820
caagccattt tccaggcctg cttgttacgc ttccgtccaa taatgatgac cacgctggcg    2880
gcgctgttcg gcgcactgcc attggtgtta tctggcggag acggttcgga attacggcag    2940
ccgctgggga taaccattgt cggcggtttg gtcatgagcc agctcctgac gctctatacc    3000
acgccggtgg tgtacctctt tttcgatcgt ctgcggctac gttttcgcg taaaaatagc    3060 aaaccggtag tagagatatg a                                              3081
```

<210> SEQ ID NO 10
<211> LENGTH: 1206
<212> TYPE: DNA
<213> ORGANISM: Salmonella

<400> SEQUENCE: 10

```
atgttgatag ccggcgtcat cgccgccatc gggggcgtga tttacatggc cggcgaagca     60
ctatgggata agacaacgc cgtcggcccc ccggccagcg cgccgcctcc accgtcggta    120
ccggttgcta agcccttag ccgtacactc gcgcctacgg cggaattcac cggttttctg    180
gccgcgccgg aaaccgtgga gctgcgttcg cgcgtgggag gaacccttga cgccatcagc    240
gttccggaag gacgtctggt aagccgcgga caactgctgt tccagatcga tccgcgcccg    300
ttcgaggtcg ccctcgacac cgccgtcgcg caattacgtc aggctgaagt actggcccgc    360
caggcgcagg cggatttcga tcgcattcaa cgactggtcg ccagcggcgc cgtatcacgt    420
aaaaacgctg acgatgtcac cgccacgcgt aatgcgcgac aggcgcagat gcaatcggcc    480
aaagccgccg tcgccgcagc gcgccttgaa ctctcctgga cccgtattac cgcgcccatt    540
gccggacgcg ttgaccgcat actggtgacc cggggcaatc tggtcagcgg cggcgtagcg    600
```

-continued

```
ggtaacgcca cgcttctgac gactatcgtg tctcacaatc ccatgtatgt gtatttcgat      660
attgacgaag ccacctggct gaaggcgtta cggcataccc gctccgacaa aaatccaccg      720
gtagtcaaca tggggttaac caccgataac gggctgcctt atcagggcgt actcgacttt      780
atgggcaatc agatgaaccg cagcaccggc actatccggg cacgcgccgt gattcctgac      840
cccgacggaa tgctttctcc cggcctgttt gcccgaatca gtttgcccat cggcgagccg      900
cgggaaaccg tgctgattga cgatctggcg gtgagcgccg atcagggcaa aaactatgtg      960
ctgatcgtcg gcaaggagaa tcaggtggag tatcgtccgg ttgagttggg acaaatggtc     1020
gatggattcc gcgtcgttac acagggagta ctgccgggga aaaaaatcat cctcaagggg     1080
ctggtgcgtc ctggcatgac cgttgcgcca cgtctggtgc cgatgcggca gaatgtgacc     1140
gacaaacaga ccgcgacatt gactaaagcg gacggcgaca gtgcgccgaa ggcggtgcgc     1200
caatga                                                                1206

<210> SEQ ID NO 11
<211> LENGTH: 3168
<212> TYPE: DNA
<213> ORGANISM: Salmonella

<400> SEQUENCE: 11
atgaaattca cccacttttt cattgcacgc cccatcttcg ccatcgtcct gtcgctgtta       60
atgctgctgg ctggcgctat cgccttttta aaactgccgc tgagtgaata tccggccgtt      120
acgccgccca cggtacaggt tagcgccagc taccccggcg ctaacccgca agtgattgcc      180
gatacggtag ccgcgccgct ggaacaggtg atcaacggcg ttgacggcat gttgtatatg      240
aatacccaga tggccattga tggtcgcatg gttatctcta tcgccttcga acagggaacc      300
gatcctgata tggcgcaaat tcaggtgcaa aaccgggtat cccgcgcgct gcctcgcctg      360
cccgaagaag tccagcgaat tggcgttgta acggagaaaa cgtcccccga tatgttgatg      420
gtggttcatc ttgtctcgcc gcaaaaacgc tatgactcgc tttacctgtc taacttcgcc      480
atccggcagg ttcgcgacga actggcccgt ttacccggcg tcggcgatgt tctcgtctgg      540
ggcgcgggcg agtacgccat gcgcgtctgg ctggacccgg cgaaaatcgc caaccgcggt      600
cttaccgcca gtgatatcgt tacggcgttg cgggaacaaa acgtacaggt cgccgccggt      660
tccgtcgggc aacagccgga ggcctccgcc gcttttcaga tgacggtaaa cacgctgggc      720
cgcctgacca gcgaagaaca gttcggcgag attgtggtaa aaatcggcgc tgacggcgag      780
gtgacgcgtc tgcgtgatgt cgcccgcgtc acgctgggcg cagatgccta tcgctgcgc       840 agtttactga atggcgaagc ggcgccagcg ttacagatta ttcaaagtcc gggcgccaat      900
gcgattgacg tttctaacgc gattcgcggc aaaatggatg agttgcagca aaacttcccg      960
caggatatcg aataccggat tgcctatgat cctacggtct tcgtgcgcgc atcgctacaa     1020
tcggtggcga ttacgttgct ggaagccctc gtgctggtcg tccttgtcgt ggtgatgttc     1080
ctgcaaacct ggcgggcgtc cattattcct ctggtggcgg ttcccgtttc gctggtcggc     1140
acctttgcct tgatgcacct gtttggcttt tcgctgaata cgctttcgct gtttggtttg     1200
gtcctgtcga taggtatcgt tgtcgatgac gccatcgttg tggtcgaaaa cgtggaacgg     1260
catatctcgc agggcaaaag tcccggagag gcggcaaaga aggcgatgga tgaagtcact     1320
ggtcccattc tttctattac ctcggtgcta acggcggtct ttatcccttc cgcattcctg     1380
gcgggcctgc agggtgagtt ttatcgtcag ttcgcgttga ccatcgctat ttcgaccatc     1440
```

```
ctttcggcca ttaactcgct gacgctctcc cctgcgctgg ctgccatttt gctaagaccg   1500
caccacgata ctgcgaaggc tgactggcta acgcggttga tgggcacggt cactggcggt   1560
tttttccatc gctttaaccg tttcttcgac agcgcgtcga accgctatgt tagcgccgtc   1620
cgtcgggccg tgcgcggcag cgtcattgtg atggtgctct atgctggctt tgtggggctg   1680
acctggcttg gcttccatca ggtgccgaac gggtttgtgc ctgcgcagga taaatactat   1740
ctcgtcggca tcgcccagct cccaagcggc gcatcgttgg atcgcacaga ggcggtcgtg   1800
aaacagatgt ccgctatcgc gctggcggaa cccggcgttg aaagcgtcgt cgtcttcccc   1860
ggtctgtcgg ttaacggccc ggtaaatgtg ccaaattcgg cgctgatgtt cgccatgctg   1920 aaacccttt g acgagcgtga agatccttcg ctttccgcta acgctatcgc cggaaagcta   1980
atgcacaaat ttagccacat tcccgacgga tttattggca tcttcccgcc accgccggtt   2040
ccagggcttg gcgcgacggg cggctttaaa ttgcagattg aagatcgtgc ggaactggga   2100
tttgaagcga tgacaaaggt gcaaagcgag attatgtcta aggcgatgca gacgcccgaa   2160
ctggccaata tgctggccag tttccagaca aacgccccgc aattacaggt ggatatcgac   2220
cgggtaaagg cgaaatcaat gggggtatcg ctcaccgaca tctttgaaac gttgcaaatt   2280
aacctcggct cgctttacgt caacgatttc aaccgatttg gccgtgcctg gcgggtgatg   2340
gcgcaggccg atgcgccatt ccgtatgcag caagaggata tcggcctgct taaagtccgc   2400
aatgcgaagg cgagatgat cccgcttagc gctttcgtca cgattatgcg ccagtcgggg   2460
ccggacagaa tcatccatta caacggcttc ccctcggtag atattagcgg tggaccggct   2520
ccgggcttct cctccggaca ggcgacggac gcgattgaaa agatcgtgcg tgaaacgtta   2580
ccggaaggga tggtcttcga atggaccgat ctggtttatc aggaaaaaca ggccggcaac   2640
tctgcgcttg ctatctttgc gctggcggtg ctgctggcct tcctgatcct ggcggcgcag   2700
tacaacagtt ggtcgctgcc cttcgccgtc ctgcttattg cgcctatgtc attactctca   2760
gccattgtcg gcgtgtgggt atctggcgga gataacaata tctttacgca gattggtttc   2820
gtggtgctgg tcggcctggc ggccaagaac gccattttga ttgtcgagtt tgcccgcgcc   2880
aaagaacacg acgcgcaga cccgctgacc gccgtactgg aagcgtcccg cctgcgtctg   2940
cgtcctatcc tgatgacctc attcgccttt atcgcaggtg tagtaccact ggtactcgcg   3000
acgggtgccg gcgcggaaat gcgacatgcg atgggcatcg ccgtgtttgc cggcatgttg   3060
ggcgtcacgc tcttcggcct gttattgacg cctgtatttt acgtggtggt tcgcaggatg   3120
gcattaaagc gtgagaaccg cgttgattcg catgatcagc aagcataa              3168
```